United States Patent
Fukushima et al.

(10) Patent No.: US 12,060,317 B2
(45) Date of Patent: Aug. 13, 2024

(54) ONIUM SALT, CHEMICALLY AMPLIFIED NEGATIVE RESIST COMPOSITION, AND PATTERN FORMING PROCESS

(71) Applicant: Shin-Etsu Chemical Co., Ltd., Tokyo (JP)

(72) Inventors: Masahiro Fukushima, Joetsu (JP); Satoshi Watanabe, Joetsu (JP); Ryosuke Taniguchi, Joetsu (JP); Naoya Inoue, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 219 days.

(21) Appl. No.: 17/331,869

(22) Filed: May 27, 2021

(65) Prior Publication Data
US 2021/0395195 A1 Dec. 23, 2021

(30) Foreign Application Priority Data
Jun. 4, 2020 (JP) .................................. 2020-097345

(51) Int. Cl.
| G03F 7/004 | (2006.01) |
| C07C 303/32 | (2006.01) |
| C07C 309/06 | (2006.01) |
| C07C 309/19 | (2006.01) |
| C07C 309/24 | (2006.01) |
| C07C 381/12 | (2006.01) |
| G03F 1/22 | (2012.01) |
| G03F 7/037 | (2006.01) |
| G03F 7/038 | (2006.01) |
| G03F 7/20 | (2006.01) |
| G03F 7/26 | (2006.01) |

(52) U.S. Cl.
CPC .......... *C07C 381/12* (2013.01); *C07C 303/32* (2013.01); *C07C 309/06* (2013.01); *C07C 309/19* (2013.01); *C07C 309/24* (2013.01); *G03F 1/22* (2013.01); *G03F 7/0045* (2013.01); *G03F 7/037* (2013.01); *G03F 7/0382* (2013.01); *G03F 7/2004* (2013.01); *G03F 7/26* (2013.01)

(58) Field of Classification Search
CPC ... G03F 7/0045; G03F 7/0382; C07C 303/32; C07C 381/12; C07C 309/19; C07C 309/23; C07C 309/24; C07C 309/39; C07C 309/44; C07C 309/58; C07C 309/60
See application file for complete search history.

(56) References Cited

U.S. PATENT DOCUMENTS

| 9,244,348 B2 | 1/2016 | Masunaga et al. |
| 2011/0269074 A1 | 11/2011 | Aqad et al. |
| 2012/0225385 A1* | 9/2012 | Ichikawa .............. C07C 381/12 |
| | | 549/511 |
| 2017/0131634 A1* | 5/2017 | Nakagawa .............. G03F 7/203 |
| 2018/0011401 A1 | 1/2018 | Utsumi et al. |
| 2018/0275516 A1 | 9/2018 | Fujiwara et al. |
| 2018/0335696 A1 | 11/2018 | Hatakeyama et al. |
| 2019/0064665 A1 | 2/2019 | Fujiwara et al. |
| 2019/0107778 A1* | 4/2019 | Komuro ................. G03F 7/2041 |
| 2019/0112265 A1* | 4/2019 | Masuyama .......... C07D 317/72 |
| 2019/0361348 A1* | 11/2019 | Kotake ................. G03F 7/0382 |

FOREIGN PATENT DOCUMENTS

| CN | 1991585 B * | 6/2011 | ............. C07C 25/18 |
| JP | 2006-162735 A | 6/2006 | |
| JP | 2011-121937 A | 6/2011 | |
| JP | 2011-215619 A | 10/2011 | |
| JP | 2013-164588 A | 8/2013 | |
| JP | 2018-197853 A | 12/2018 | |
| JP | 2019-019121 A | 2/2019 | |
| JP | 2019-204048 A | 11/2019 | |

(Continued)

OTHER PUBLICATIONS

Office Action dated May 31, 2022, issued in counterpart to TW Application No. 110119915. (7 pages).

(Continued)

*Primary Examiner* — John S Chu
(74) *Attorney, Agent, or Firm* — WHDA, LLP

(57) ABSTRACT

An onium salt having a partial structure of formula (A) is provided wherein $R^{a1}$ and $R^{a2}$ are hydrogen or a $C_1$-$C_{10}$ hydrocarbyl group in which hydrogen may be substituted by halogen and —$CH_2$— may be replaced by —O— or —C(=O)—, both $R^{a1}$ and $R^{a2}$ are not hydrogen at the same time, $R^{a1}$ and $R^{a2}$ may bond together to form an aliphatic ring. A chemically amplified negative resist composition comprising the onium salt as acid generator forms a pattern of good profile having a high sensitivity, improved dissolution contrast, reduced LWR and improved CDU.

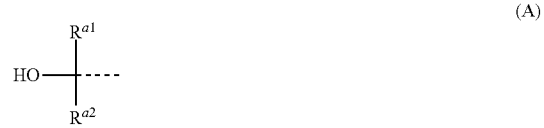

(A)

15 Claims, 2 Drawing Sheets

(56) References Cited

FOREIGN PATENT DOCUMENTS

| | | |
|---|---|---|
| TW | 201838973 A | 11/2018 |
| TW | 201920092 A | 6/2019 |
| WO | 2016/088648 A1 | 6/2016 |

OTHER PUBLICATIONS

Office Action dated Nov. 29, 2022, issued in counterpart JP application No. 2020-097345, with English translation. (8 pages).
Office Action dated Apr. 18, 2023, issued in counterpart JP application No. 2020-097345, with English Translation. (6 pages).

* cited by examiner

ONIUM SALT, CHEMICALLY AMPLIFIED NEGATIVE RESIST COMPOSITION, AND PATTERN FORMING PROCESS

CROSS-REFERENCE TO RELATED APPLICATION

This non-provisional application claims priority under 35 U.S.C. § 119(a) on Patent Application No. 2020-097345 filed in Japan on Jun. 4, 2020, the entire contents of which are hereby incorporated by reference.

TECHNICAL FIELD

This invention relates to an onium salt, a chemically amplified negative resist composition comprising the same, and a pattern forming process using the resist composition.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film. To form patterns of smaller feature size, research efforts have been made on the resist compositions for lithography using short wavelength radiation, typically electron beam (EB) and extreme ultraviolet (EUV).

With the advance of pattern miniaturization, more attention is paid on the edge roughness (LWR) of line patterns and the critical dimension uniformity (CDU) of hole and dot patterns. The influence of localization and agglomeration of a base polymer or acid generator and the influence of acid diffusion are pointed out. There is a tendency that LWR and CDU are aggravated as resist film becomes thinner. The thickness reduction of resist film to comply with the advance of pattern miniaturization causes degradation of LWR and CDU, which is a serious problem.

The EUV resist composition is required to meet high sensitivity, high resolution and low LWR at the same time. As the acid diffusion distance is reduced, LWR or CDU is improved, but sensitivity becomes lower. For example, as the PEB temperature becomes lower, LWR or CDU is improved, but sensitivity becomes lower. Also, when the amount of quencher added is increased, LWR or CDU is improved, but sensitivity becomes lower. It is necessary to overcome the tradeoff relationship between sensitivity and LWR or CDU (see Patent Document 1).

Resist compositions adapted for photolithography include positive tone compositions wherein exposed regions are dissolved to form patterns and negative tone compositions wherein exposed regions are retained to form patterns. A composition of either tone which is easier to use is selected depending on a particular mode of resist pattern needed. In forming a dot pattern, on use of a positive resist composition adapted for alkaline development, a bright mask must be combined therewith. Undesirably, the mask is readily degraded because a large area must be subjected to exposure to high-energy EB or EUV. The problem is avoided by using a dark mask requiring only a small exposure area. In this case, a negative resist composition of the type wherein exposed regions are insolubilized in alkaline developer is indispensable (see Patent Document 2).

On use of a negative resist composition adapted for alkaline developer, an acid is generated in the exposed region, and the base polymer is insolubilized under the action of the acid. Since the acid generated in the exposed region has high affinity to the alkaline developer, the exposed region is dissolved during development, giving rise to such problems as a pattern top loss and degradations of LWR or CDU. Also, the control of acid diffusion is not regarded sufficient, and the base polymer is insufficiently insolubilized due to diffusion of the acid from the exposed region to the unexposed region. This suggests insufficient resistance to alkaline development, similarly inviting top-loss profiles. The unexposed region to be dissolved in the original sense becomes less alkaline dissolvable, leaving scums.

CITATION LIST

Patent Document 1: JP-A 2018-197853 (US 20180335696)

Patent Document 2: JP-A 2013-164588 (U.S. Pat. No. 9,244,348)

SUMMARY OF INVENTION

There is a need for a negative tone resist composition which falls in the concept of acid-catalyzed chemically amplified resist compositions and which has a high sensitivity and forms a pattern of good profile having reduced values of LWR of line-and-space (LS) patterns or CDU of dot patterns and experiencing minimal top loss.

An object of the invention is to provide a chemically amplified negative resist composition which has a high sensitivity and dissolution contrast and forms a pattern of good profile having reduced LWR and improved CDU, an onium salt serving as an acid generator in the resist composition, and a resist pattern forming process using the resist composition.

The inventors have found that a chemically amplified negative resist composition comprising an acid generator in the form of an onium salt having a specific partial structure and a specific base polymer has a high sensitivity and dissolution contrast and forms a pattern of good profile having reduced LWR and improved CDU.

In one aspect, the invention provides an onium salt having a partial structure represented by the formula (A).

Herein $R^{a1}$ and $R^{a2}$ are each independently hydrogen or a $C_1$-$C_{10}$ hydrocarbyl group in which some or all hydrogen atoms may be substituted by halogen and a constituent —$CH_2$— may be replaced by —O— or —C(=O)—, both $R^{a1}$ and $R^{a2}$ are not hydrogen at the same time, $R^{a1}$ and $R^{a2}$ may bond together to form an aliphatic ring with the carbon atom to which they are attached, the broken line designates a valence bond.

Preferably, the onium salt contains an anion having the formula (A1) and a cation selected from the formulae (A1-a) to (A1-c).

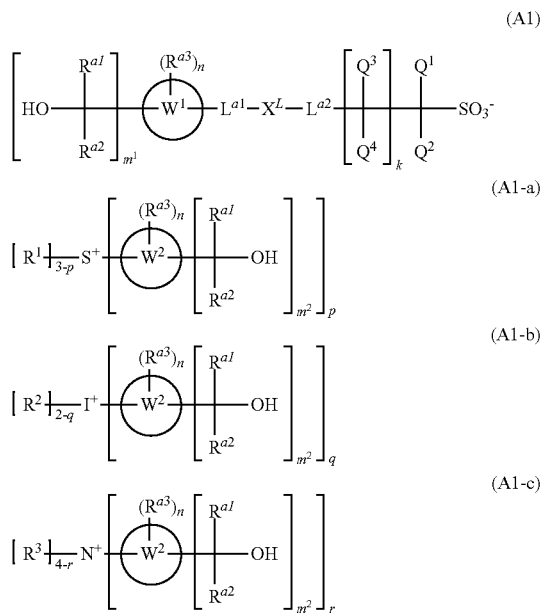

Herein $R^{a1}$ and $R^{a2}$ are as defined above, k is an integer of 0 to 4 $m^1$ is an integer of 1 to 4, $m^2$ is each independently an integer of 0 to 4, n is each independently an integer of 0 to 10, p is an integer of 0 to 3, q is an integer of 0 to 2, r is an integer of 0 to 4.

$R^{a3}$ is each independently a $C_1$-$C_{20}$ hydrocarbyl group which may contain a heteroatom, when n is 2 or more, $R^{a3}$ may be the same or different and two or more $R^{a3}$ may bond together to form a ring with the atom on $W^2$ to which they are attached.

$W^1$ is a $C_3$-$C_{20}$ (n+2)-valent group having a mono- or polycyclic structure, $W^2$ is each independently a $C_3$-$C_{20}$ ($m^2$+n+1)-valent group having a mono- or polycyclic structure, in which a constituent —$CH_2$— may be replaced by —O—, —S— or —C(=O)—.

$Q^1$ and $Q^2$ are each independently fluorine or a $C_1$-$C_6$ fluorinated saturated hydrocarbyl group.

$Q^3$ and $Q^4$ are each independently hydrogen, fluorine or a $C_1$-$C_6$ fluorinated saturated hydrocarbyl group.

$L^{a1}$ and $L^{a2}$ are each independently a single bond, ether bond, ester bond, sulfonate bond, carbonate bond or carbamate bond.

$X^L$ is a single bond or a $C_1$-$C_{40}$ hydrocarbylene group which may contain a heteroatom.

$R^1$, $R^2$ and $R^3$ are each independently a $C_1$-$C_{20}$ hydrocarbyl group which may contain a heteroatom, any two of two $R^1$ and $W^2$ may bond together to form a ring with the sulfur atom in the formula, any two of three $R^3$ and $W^2$ may bond together to form a ring with the nitrogen atom in the formula.

In a preferred embodiment, the anion having formula (A1) has the formula (A2):

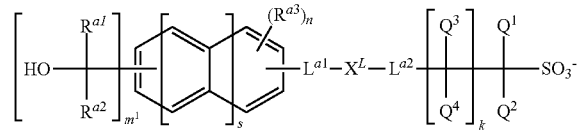

wherein $Q^1$ to $Q^4$, $L^{a1}$, $L^{a2}$, $X^L$, $R^{a1}$ to $R^{a3}$, k, $m^1$ and n are as defined above, s is an integer of 0 to 2.

In a preferred embodiment, the anion having formula (A2) has the formula (A3):

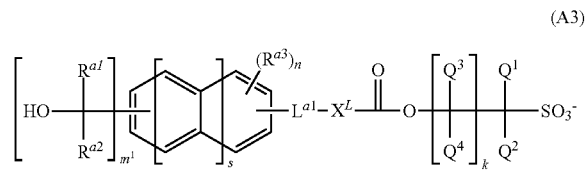

wherein $Q^1$ to $Q^4$, $L^a$, $X^L$, $R^{a1}$ to $R^{a3}$, k, $m^1$, n and s are as defined above.

In a preferred embodiment, the anion having formula (A3) has the formula (A4):

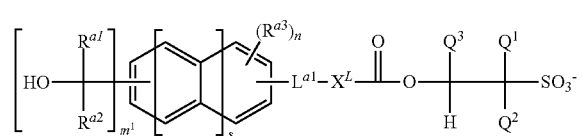

wherein $Q^1$ to $Q^3$, $L^{a1}$, $X^L$, $R^{a1}$ to $R^{a3}$, $m^1$, n and s are as defined above.

In another aspect, the invention provides a photoacid generator comprising the onium salt defined above.

In a further aspect, the invention provides a chemically amplified negative resist composition comprising the photoacid generator defined above.

In a preferred embodiment, the chemically amplified negative resist composition further comprises a base polymer comprising recurring units having the formula (B1) and recurring units having the formula (B2).

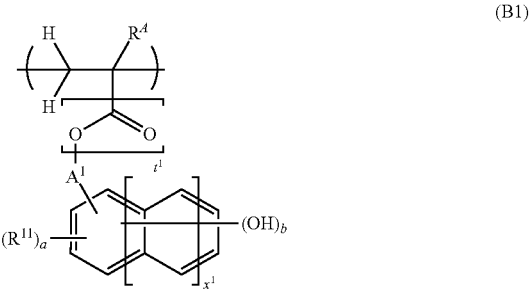

-continued (B2)

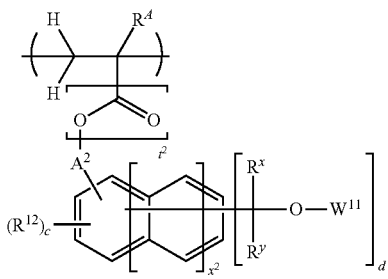

Herein $R^A$ is hydrogen, fluorine, methyl or trifluoromethyl. $R^{11}$ and $R^{12}$ are each independently halogen, an optionally halogenated $C_1$-$C_6$ saturated hydrocarbyl group, optionally halogenated $C_2$-$C_8$ saturated hydrocarbylcarbonyloxy group, or optionally halogenated $C_1$-$C_6$ saturated hydrocarbyloxy group. $A^1$ and $A^2$ are each independently a single bond or a $C_1$-$C_{10}$ saturated hydrocarbylene group in which a constituent —$CH_2$— may be replaced by —O—. $W^{11}$ is hydrogen, a $C_1$-$C_{10}$ aliphatic hydrocarbyl group, or an optionally substituted aryl group, a constituent —$CH_2$— in the aliphatic hydrocarbyl group may be replaced by —O—, —C(=O)—, —O—C(=O)— or —C(=O)—O—. $R^x$ and $R^y$ are each independently hydrogen, or a $C_1$-$C_{15}$ saturated hydrocarbyl group which may be substituted with a hydroxyl or saturated hydrocarbyloxy moiety, or an optionally substituted aryl group, both $R^x$ and $R^y$ are not hydrogen at the same time, $R^x$ and $R^y$ may bond together to form a ring with the carbon atom to which they are attached, $t^1$ and $t^2$ are each independently 0 or 1, $x^1$ and $x^2$ are each independently an integer of 0 to 2, a is an integer meeting $0 \le a \le 5+2x^1-b$, c is an integer meeting $0 \le c \le 5+2x^2-d$, b and d are each independently an integer of 1 to 3.

In a preferred embodiment, the recurring units of formula (B1) have the formula (B1-1) and the recurring units of formula (B2) have the formula (B2-1):

(B1-1)

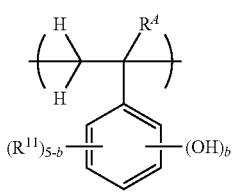

(B2-1)

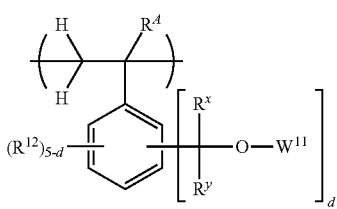

wherein $R^A$, $R^{11}$, $R^{12}$, $R^x$, $R^y$, $W^{11}$, b and d are as defined above.

In a preferred embodiment, the base polymer further comprises recurring units of at least one type selected from recurring units having the formula (B3), recurring units having the formula (B4), and recurring units having the formula (B5).

(B3)

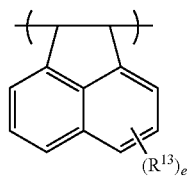

(B4)

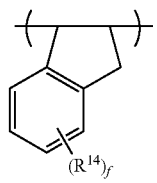

(B5)

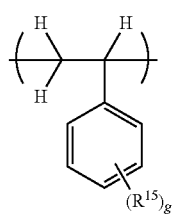

Herein $R^{13}$ and $R^{14}$ are each independently hydroxyl, halogen, acetoxy, an optionally halogenated $C_1$-$C_8$ alkyl group, optionally halogenated $C_1$-$C_8$ saturated hydrocarbyloxy group, optionally halogenated $C_2$-$C_8$ saturated hydrocarbylcarbonyl group, or optionally halogenated $C_2$-$C_8$ saturated hydrocarbylcarbonyloxy group, with the proviso that $R^{13}$ and are not acid labile groups. $R^{15}$ is halogen, acetoxy, an optionally halogenated $C_1$-$C_8$ alkyl group, optionally halogenated $C_1$-$C_8$ saturated hydrocarbyloxy group, optionally halogenated $C_2$-$C_8$ saturated hydrocarbylcarbonyl group, or optionally halogenated $C_2$-$C_8$ saturated hydrocarbylcarbonyloxy group, with the proviso that $R^{15}$ is not an acid labile group, e, f and g are each independently an integer of 0 to 4.

The chemically amplified negative resist composition may further comprise an organic solvent, a quencher, and/or a crosslinker.

In a still further aspect, the invention provides a process for forming a resist pattern comprising the steps of applying the chemically amplified negative resist composition defined above onto a substrate to form a resist film thereon, exposing patternwise the resist film to high-energy radiation, and developing the exposed resist film in an alkaline developer.

Typically, the high-energy radiation is EB or EUV of wavelength 3 to 15 nm.

Advantageous Effect of Invention

The onium salt of the invention is characterized by having a tertiary or secondary hydroxyl group in the cation and/or anion structure and functions as a photoacid generator. Although the unexposed region remains highly hydrophilic because of the hydroxyl-containing structure, the exposed region turns to a hydrophobic structure through the mechanism that once an acid is generated upon exposure, the tertiary or secondary hydroxyl group in the cation and/or anion structure undergoes dehydration reaction. Then the dissolution contrast between exposed and unexposed regions is improved. The base polymer has a high dissolution contrast and a high insolubilizing ability in the exposed region. By virtue of these advantages, a chemically amplified negative resist composition having a high sensitivity and improved LWR or CDU can be designed. Since a polarity switch takes place not only on the base polymer, but also on the photoacid generator, the dissolution of the composition in alkaline developer is reduced. The negative pattern formed from the inventive chemically amplified negative resist composition is restrained in the dissolution of exposed region in alkaline developer and forms a pattern of good profile with minimal top loss, as compared with negative patterns formed from conventional negative resist compositions.

DESCRIPTION OF PREFERRED EMBODIMENTS

Figure 1:
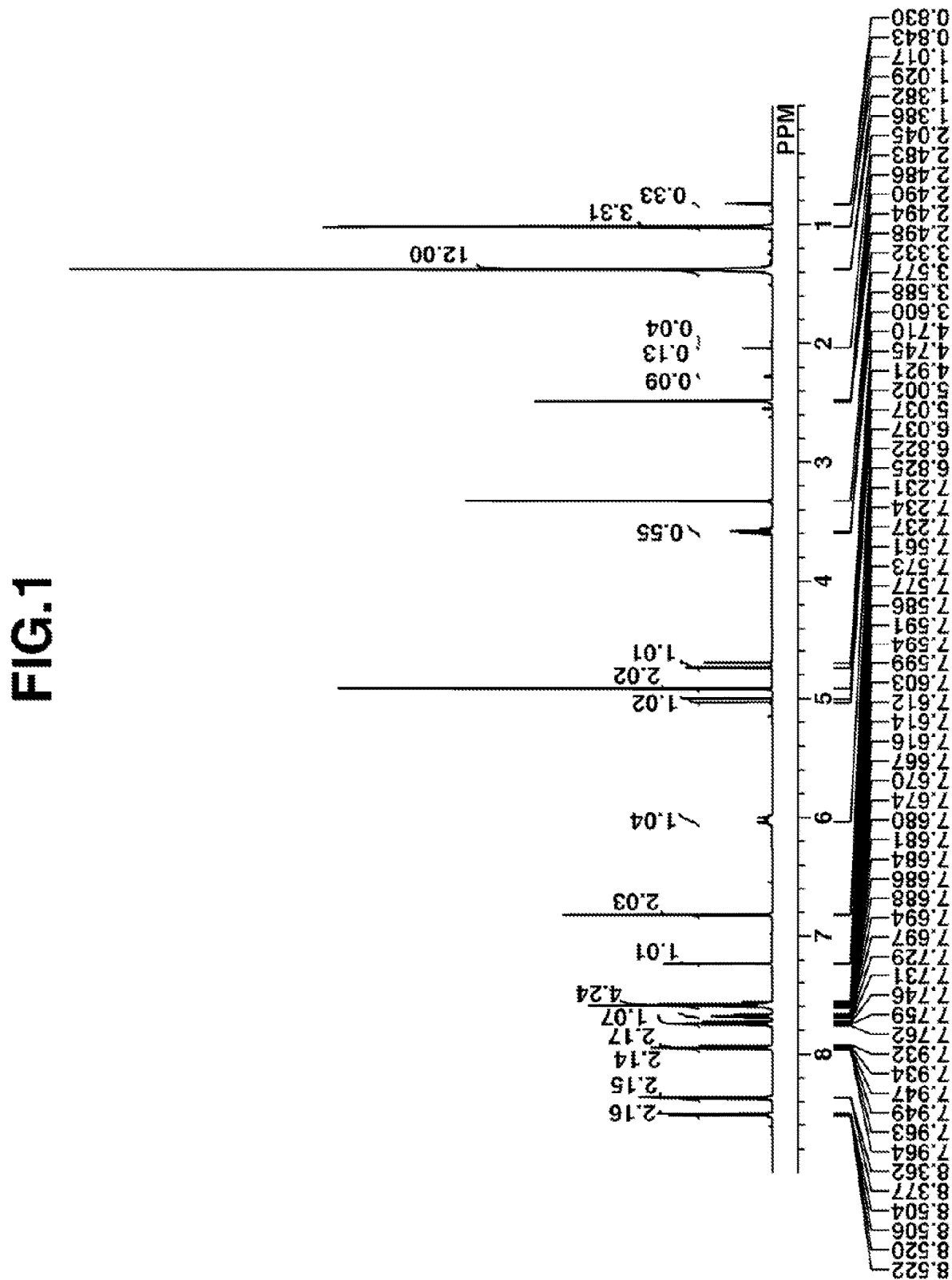
FIG. 1 is a diagram showing the $^1$H-NMR spectrum of PAG-1 prepared in Example 1-1.

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, Me stands for methyl, Ac for acetyl, and the broken line designates a valence bond.

The abbreviations and acronyms have the following meaning.
EB: electron beam
EUV: extreme ultraviolet
Mw: weight average molecular weight
Mn: number average molecular weight
Mw/Mn: molecular weight dispersity
GPC: gel permeation chromatography
PEB: post-exposure bake
PAG: photoacid generator
LWR: line width roughness
CDU: critical dimension uniformity
EL: exposure latitude Onium Salt One embodiment of the invention is an onium salt having a partial structure represented by the formula (A).

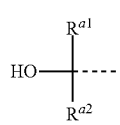
(A)

In formula (A), $R^{a1}$ and $R^{a2}$ are each independently hydrogen or a $C_1$-$C_{10}$ hydrocarbyl group in which some or all of the hydrogen atoms may be substituted by halogen atoms such as fluorine, chlorine, bromine or iodine and a constituent —CH$_2$— may be replaced by —O— or —C(=O)—. Both $R^{a1}$ and $R^{a2}$ are not hydrogen at the same time. $R^{a1}$ and $R^{a2}$ may bond together to form an aliphatic ring with the carbon atom to which they are attached.

The hydrocarbyl group may be saturated or unsaturated and straight, branched or cyclic. Examples include alkyl groups such as methyl, ethyl, propyl, isopropyl, n-butyl, sec-butyl, tert-butyl, n-pentyl, tert-pentyl, n-hexyl, 2-ethylhexyl, n-octyl, n-nonyl and n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbuyl, norbornyl and adamantyl; alkenyl groups such as vinyl; and aryl groups such as phenyl, tolyl and naphthyl. Examples of the substituted hydrocarbyl group include oxanorbornyl and fluorophenyl. $R^{a1}$ and $R^{a2}$ are preferably identical, most preferably both methyl.

Examples of the aliphatic ring that $R^{a1}$ and $R^{a2}$, taken together, form with the carbon atom to which they are attached include cyclopropane, cyclobutane, cyclopentane, and cyclohexane rings, but are not limited thereto.

The onium salt having a partial structure of formula (A) preferably contains an anion having the following formula (A1) and a cation selected from the following formulae (A1-a) to (A1-c).

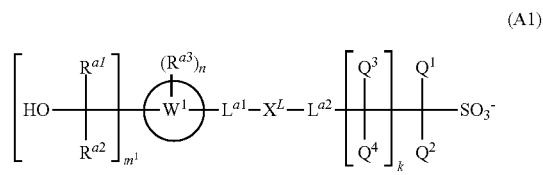
(A1)

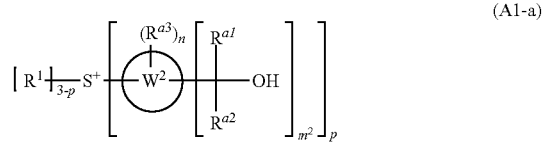
(A1-a)

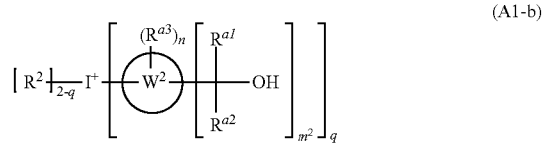
(A1-b)

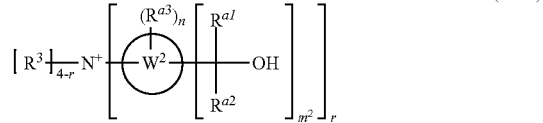
(A1-c)

In formulae (A1) and (A1-a) to (A1-c), $R^{a1}$ and $R^{a2}$ are as defined above; k is an integer of 0 to 4, $m^1$ is an integer of 1 to 4, $m^2$ is each independently an integer of 0 to 4, n is each independently an integer of 0 to 10, p is an integer of 0 to 3, q is an integer of 0 to 2, r is an integer of 0 to 4.

In formulae (A1) and (A1-a) to (A1-c), $R^{a3}$ is each independently a $C_1$-$C_{20}$ hydrocarbyl group which may contain a heteroatom. The hydrocarbyl group may be saturated or unsaturated and straight, branched or cyclic. Examples thereof include alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; and aryl groups such as phenyl, naphthyl and anthracenyl. In these hydrocarbyl groups, some or all of the hydrogen atoms may be substituted by a moiety containing a heteroatom such as oxygen, sulfur, nitrogen or halogen, or a moiety containing a heteroatom such as oxygen, sulfur or nitrogen may intervene in a carbon-carbon bond, so that the group may contain a hydroxyl moiety, cyano moiety, carbonyl moiety, ether bond, ester bond, sulfonic acid ester bond, carbonate bond, carbamate bond, amide bond, imide bond, lactone ring, sultone ring, thiolactone ring, lactam ring, sultam ring, carboxylic anhydride, or haloalkyl moiety.

When n is 2 or more, groups $R^{a3}$ may be the same or different and two or more groups $R^{a3}$ may bond together to form a ring with the atom on $W^2$ to which they are attached. Examples of the ring thus formed include cyclopropane, cyclobutane, cyclopentane, cyclohexane, norbornane, and adamantane rings. It is acceptable that two groups $R^3$ bond with a common carbon atom and bond together to form a spiro ring structure with $W^1$ or $W^2$.

In formulae (A1) and (A1-a) to (A1-c), $W^1$ is a $C_3$-$C_{20}$ (n+2)-valent group having a mono- or polycyclic structure, $W^2$ is each independently a $C_3$-$C_{20}$ ($m^2$+n+1)-valent group having a mono- or polycyclic structure. In these groups, a constituent —$CH_2$— may be replaced by —O—, —S— or —C(=O)—. Examples of the group having a mono- or polycyclic structure are shown below, but not limited thereto.

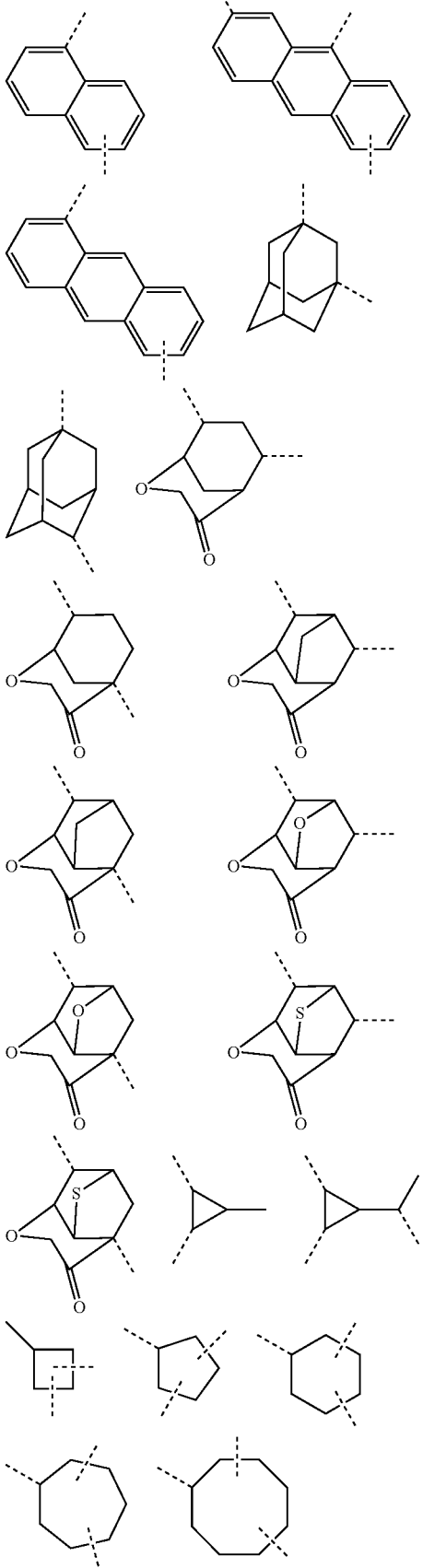

-continued

-continued

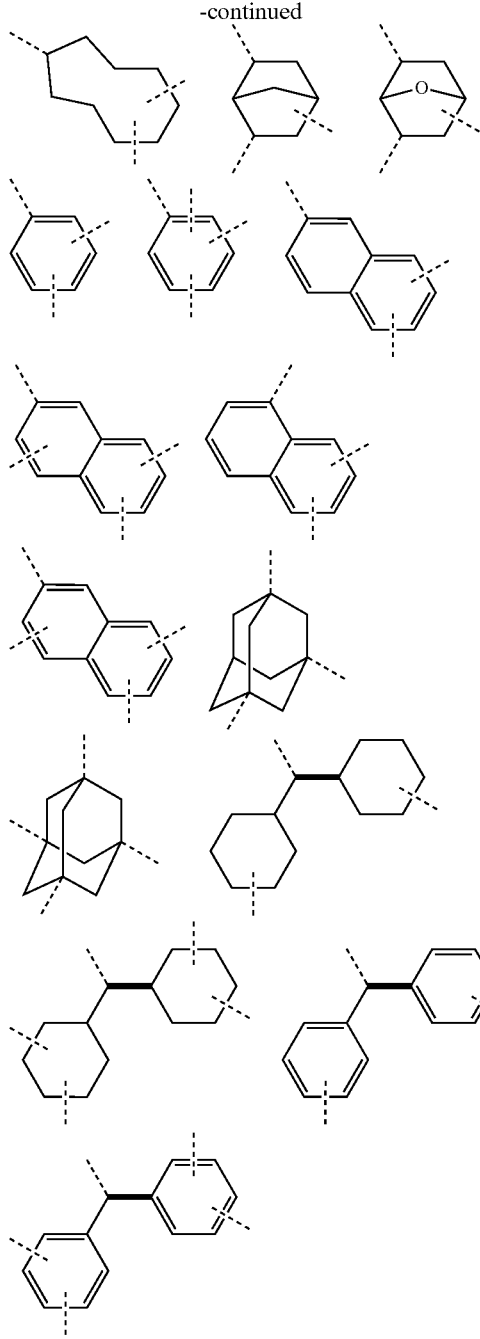

Of these, the groups having an aromatic ring are preferred for availability of starting reactants, with the groups having a benzene or naphthalene ring being more preferred.

In formulae (A1) and (A1-a) to (A1-c), $Q^1$ and $Q^2$ are each independently fluorine or a $C_1$-$C_6$ fluorinated saturated hydrocarbyl group, $Q^3$ and $Q^4$ are each independently hydrogen, fluorine or a $C_1$-$C_6$ fluorinated saturated hydrocarbyl group. The fluorinated saturated hydrocarbyl group may be straight, branched or cyclic and examples thereof include fluoromethyl, difluoromethyl and trifluoromethyl.

In formula (A1), $L^{a1}$ and $L^{a2}$ are each independently a single bond, ether bond, ester bond, sulfonate bond, carbonate bond or carbamate bond. Of these, an ether or ester bond is preferred, with the ester bond being most preferred.

In formula (A1), $X^L$ is a single bond or a $C_1$-$C_{40}$ hydrocarbylene group which may contain a heteroatom. Examples of the optionally heteroatom-containing $C_1$-$C_{40}$ hydrocarbylene group are shown below, but not limited thereto. Herein, * designates a point of attachment to $L^{a1}$ or $L^{a2}$.

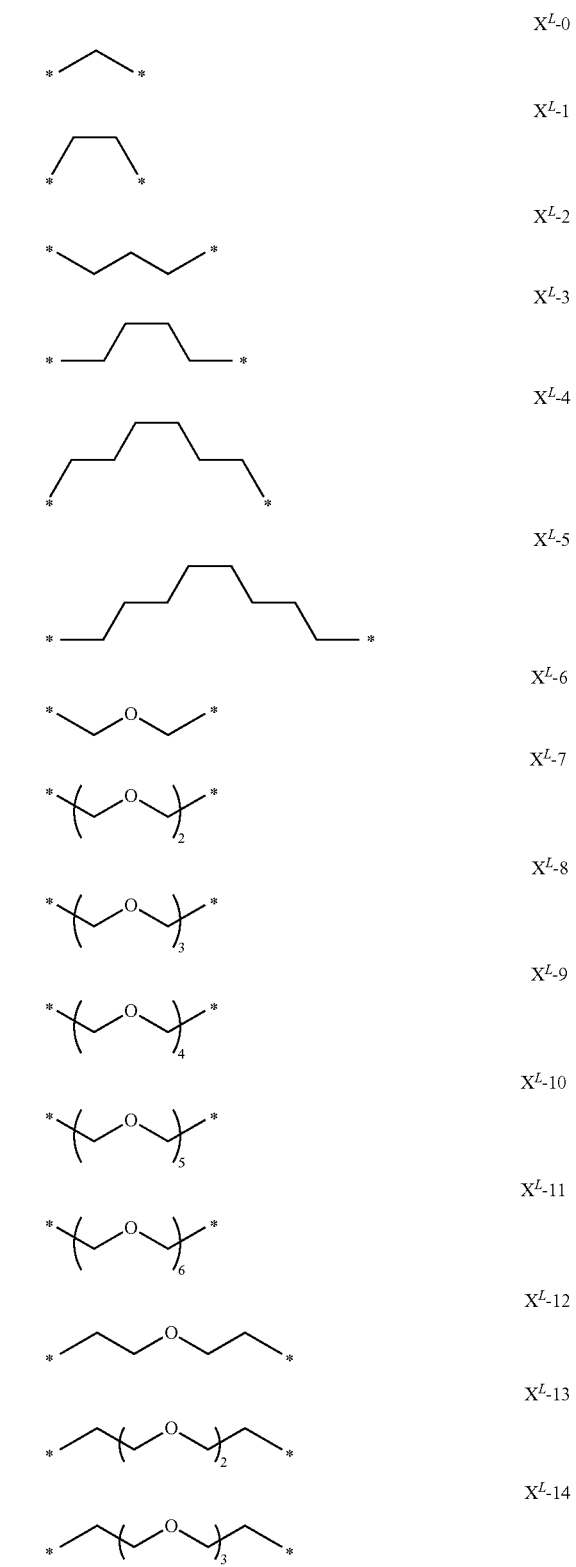

$X^L$-15
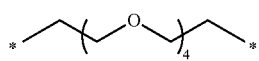
$X^L$-16
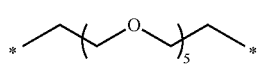
$X^L$-17
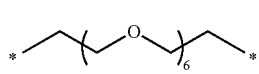
$X^L$-18
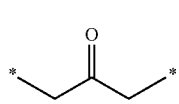
$X^L$-19
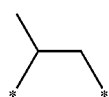
$X^L$-20
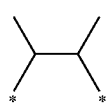
$X^L$-21
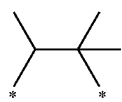
$X^L$-22
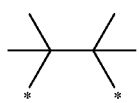
$X^L$-23
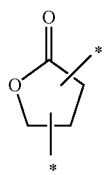
$X^L$-24
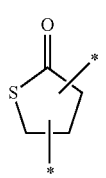
$X^L$-25
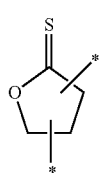
$X^L$-26
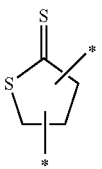
$X^L$-27
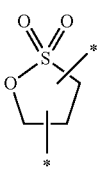
$X^L$-28
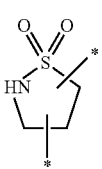
$X^L$-29
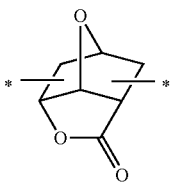
$X^L$-30
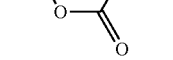
$X^L$-31
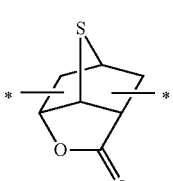
$X^L$-32
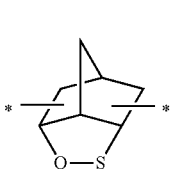

$X^L$-33

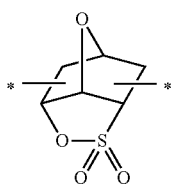

$X^L$-34

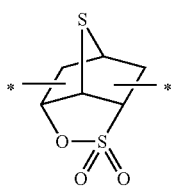

$X^L$-35

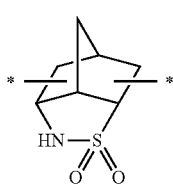

$X^L$-36

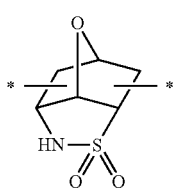

$X^L$-37

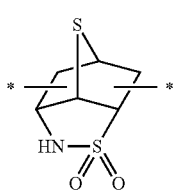

$X^L$-38

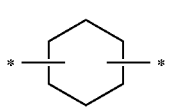

$X^L$-39

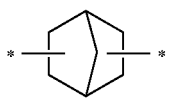

$X^L$-40

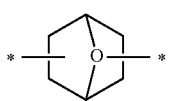

$X^L$-41

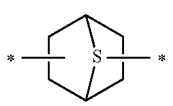

$X^L$-42

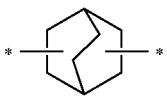

$X^L$-43

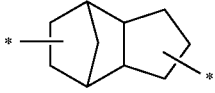

$X^L$-44

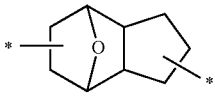

$X^L$-45

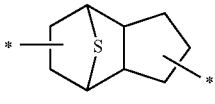

$X^L$-46

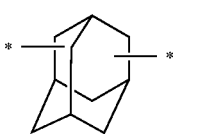

$X^L$-47

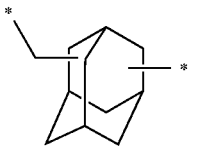

$X^L$-48

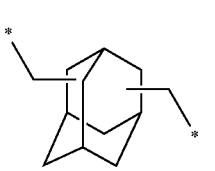

$X^L$-49

Of these, the groups $X^L$-0 to $X^L$-22 and $X^L$-47 to $X^L$-49 are preferred, with the groups $X^L$-0 to $X^L$-17 being more preferred.

Of the anions having formula (A1), those having the formula (A2) are preferred.

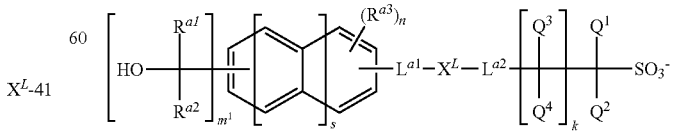

(A2)

Herein $Q^1$ to $Q^4$, $L^{a1}$, $L^{a2}$, $X^L$, $R^{a1}$ to $R^{a3}$, k, $m^1$ and n are as defined above, s is an integer of 0 to 2.

Of the anions having formula (A2), those having the formula (A3) are preferred.

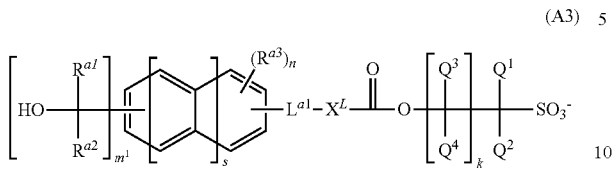

(A3)

Herein $Q^1$ to $Q^4$, $L^{a1}$, $X^L$, $R^{a1}$ to $R^3$, k, $m^1$, n and s are as defined above.

Of the anions having formula (A3), those having the formula (A4) are preferred.

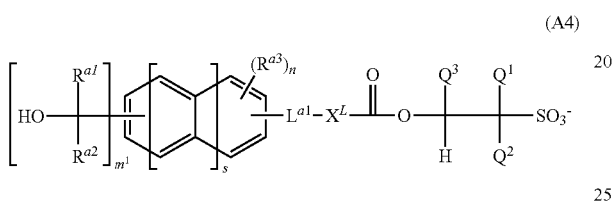

(A4)

Herein $Q^1$ to $Q^3$, $L^{a1}$, $X^L$, $R^{a1}$ to $R^{a3}$, $m^1$, n and s are as defined above.

In formulae (A1) to (A4), preferably both $Q^1$ and $Q^2$ are fluorine. $Q^3$ is preferably hydrogen, fluorine or trifluoromethyl, especially trifluoromethyl in view of the acid strength of generated acid and solvent solubility.

Examples of the anion having formula (A1) are shown below, but not limited thereto. Herein $Q^3$ is as defined above.

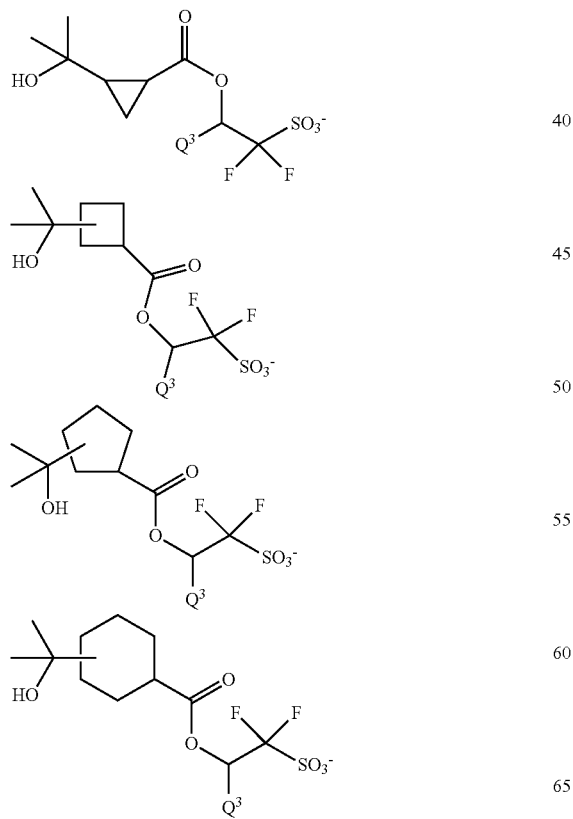

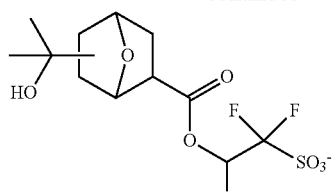

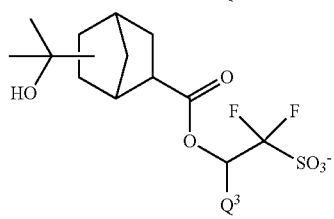

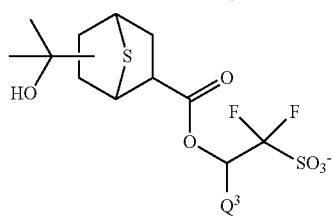

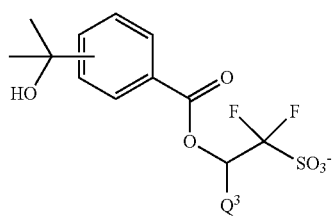

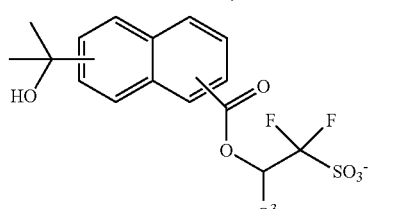

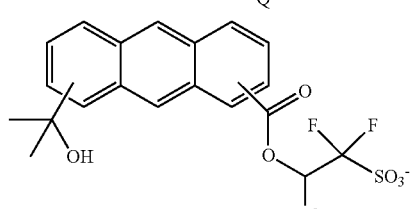

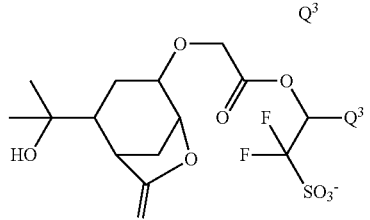

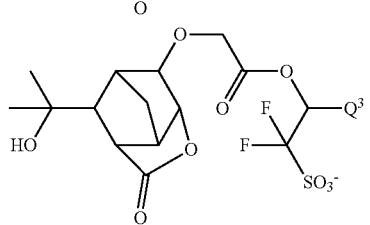

-continued
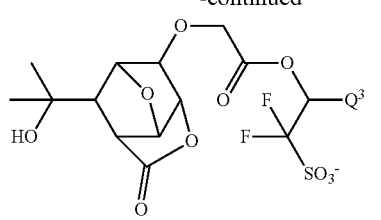
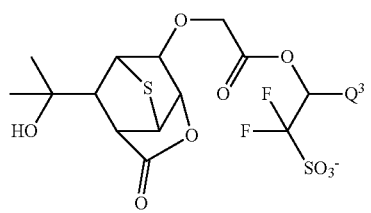
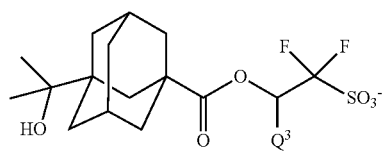
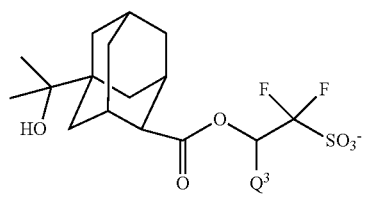
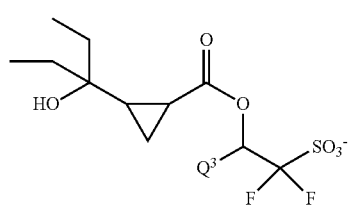
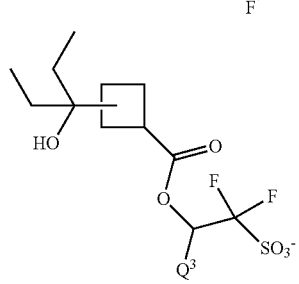
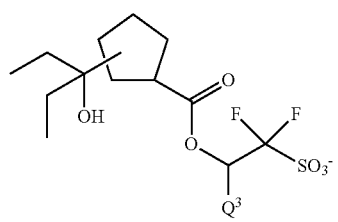
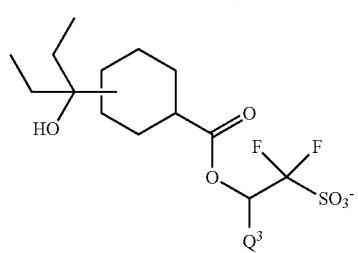
-continued
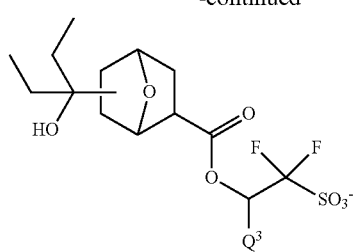
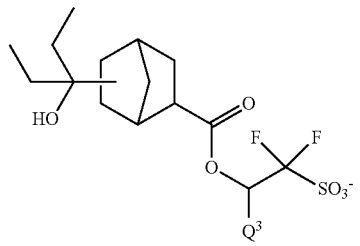
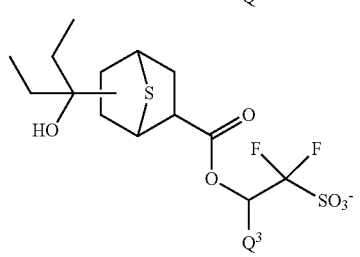
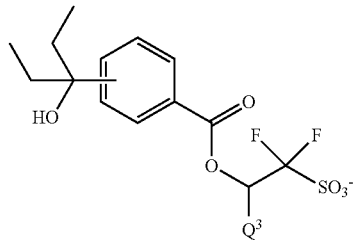
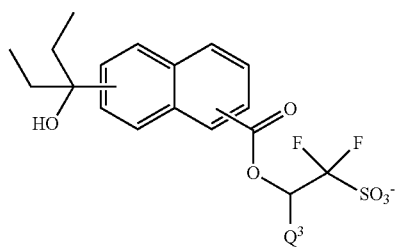
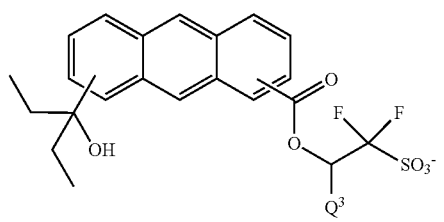
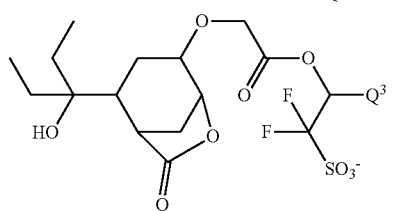

-continued
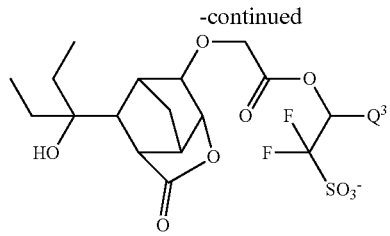
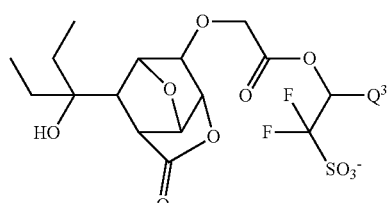
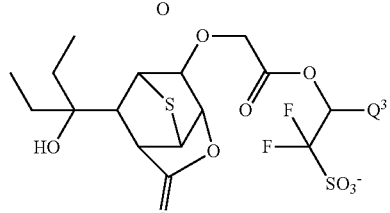
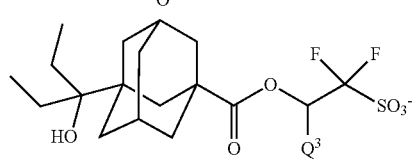
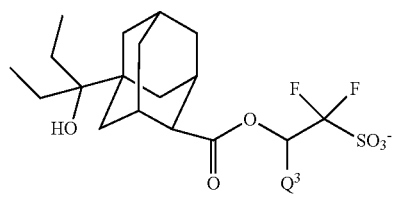
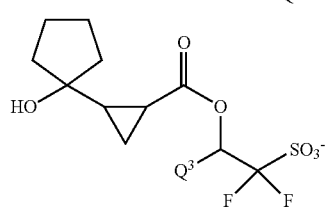
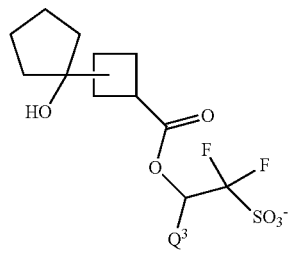
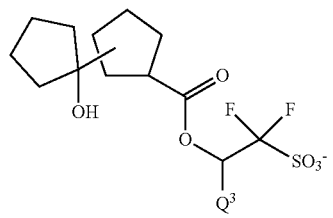
-continued
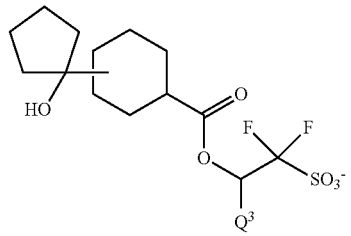
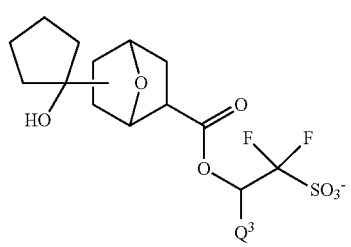
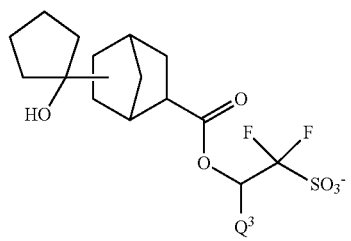
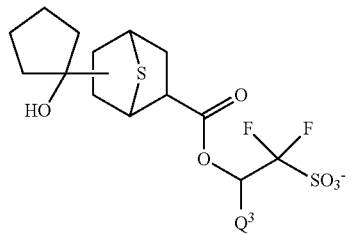
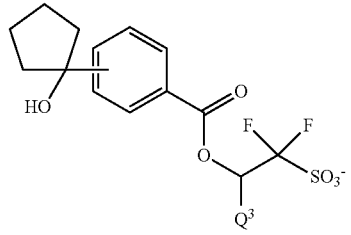
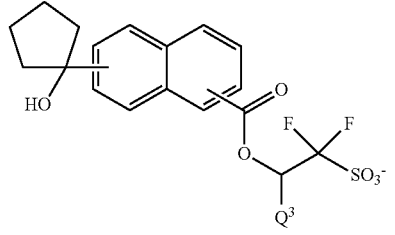
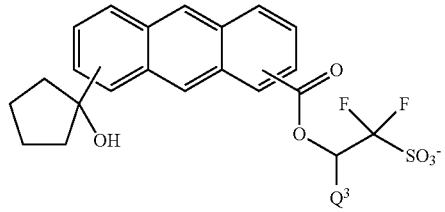

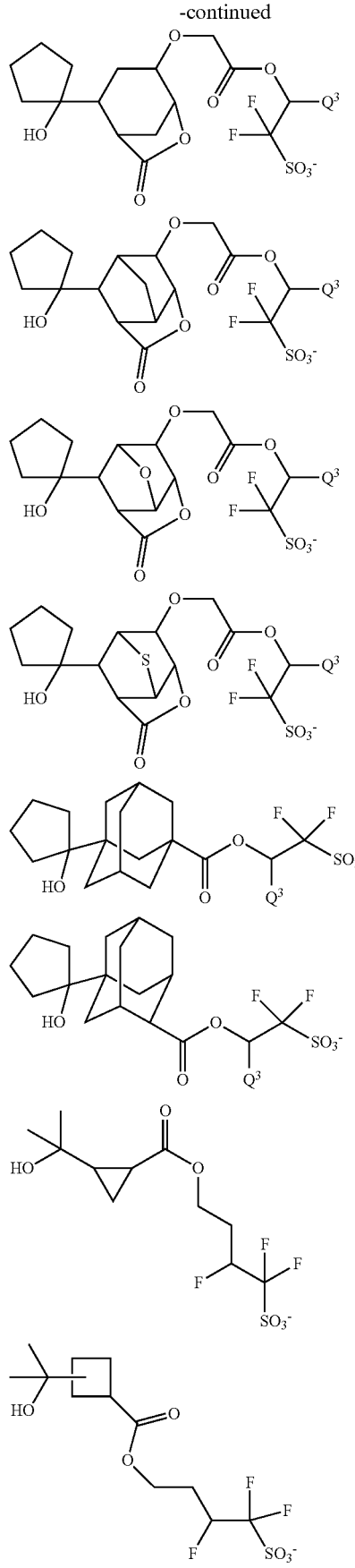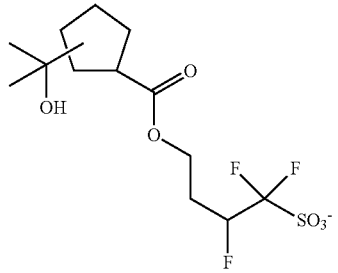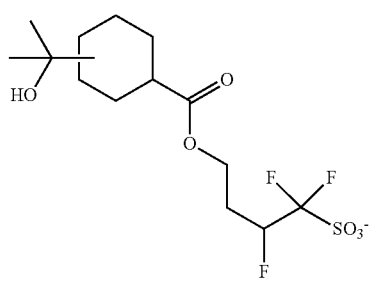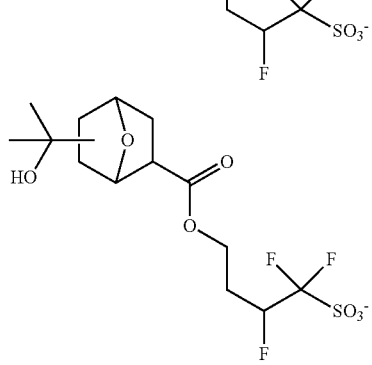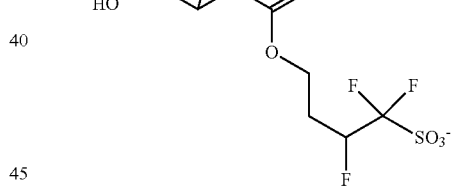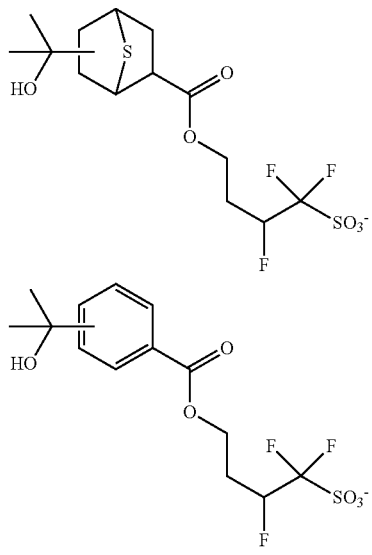

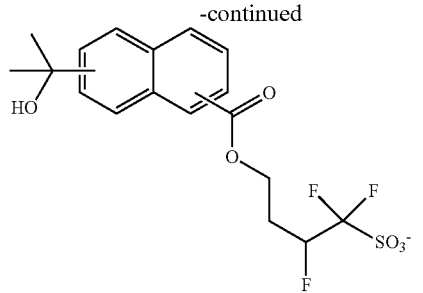
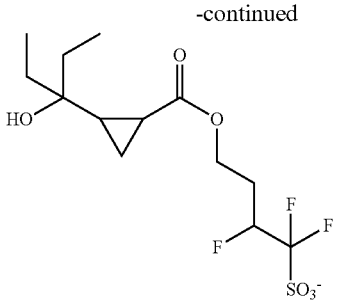
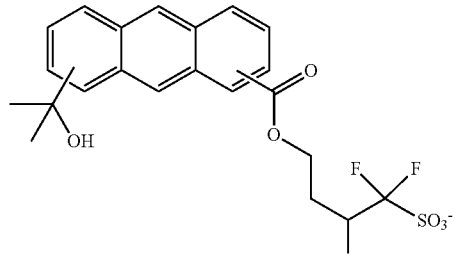
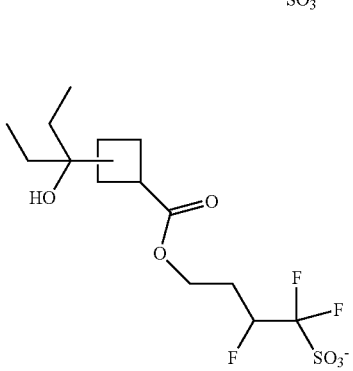
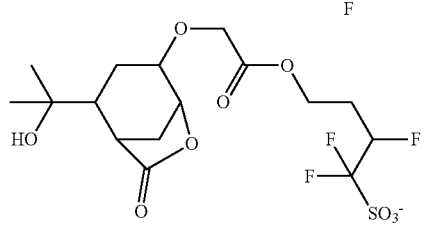
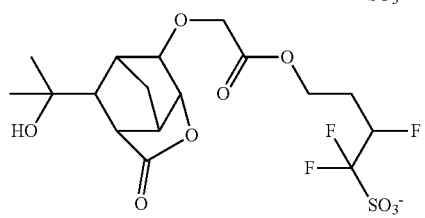
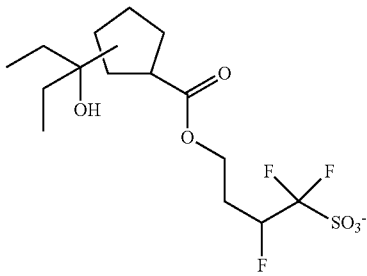
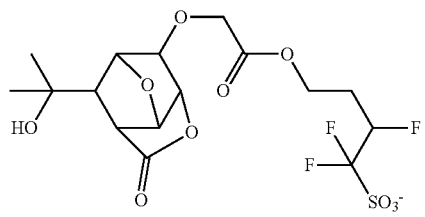
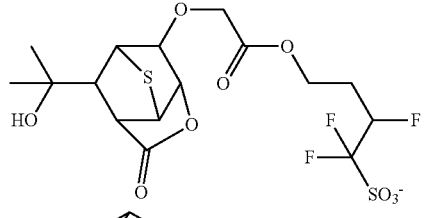
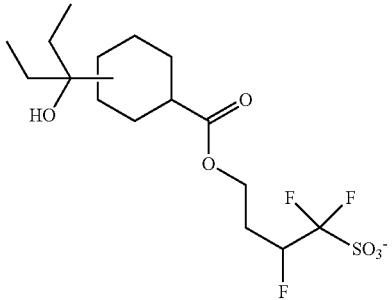
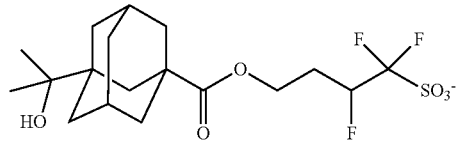
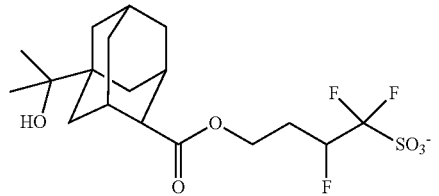
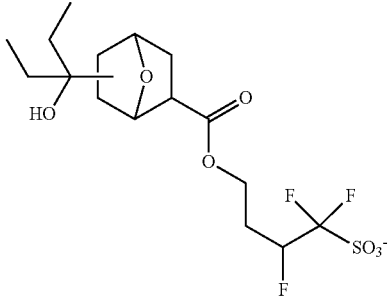

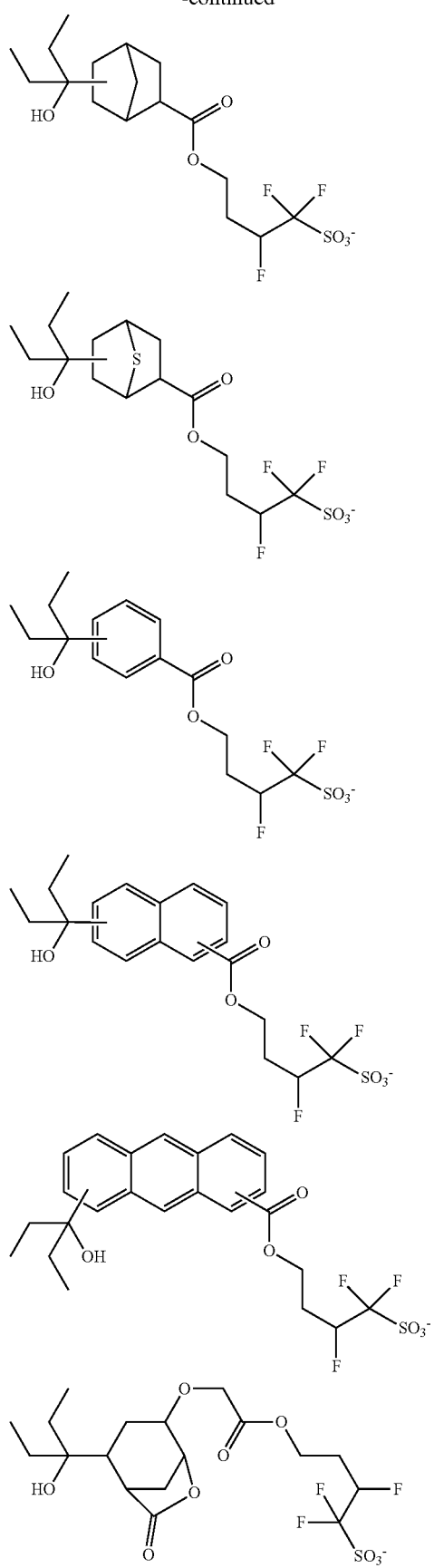
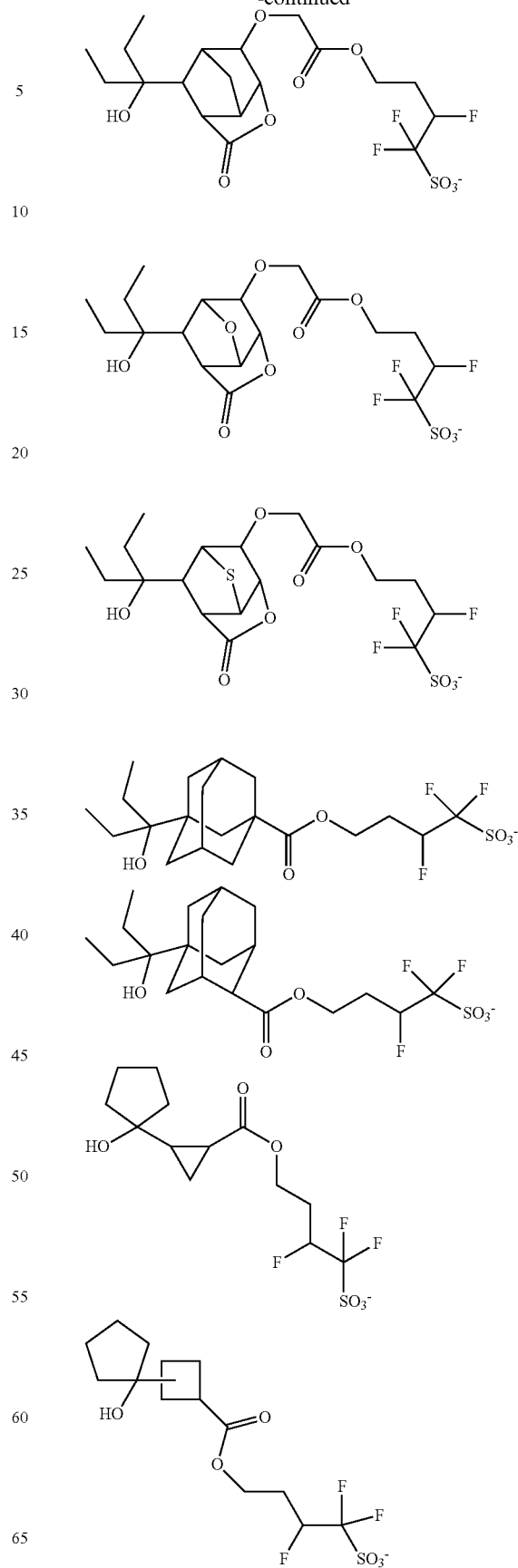

-continued
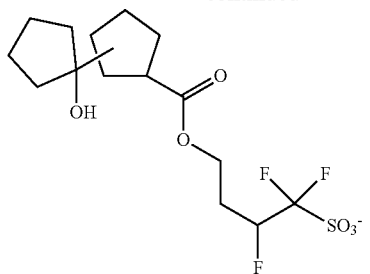
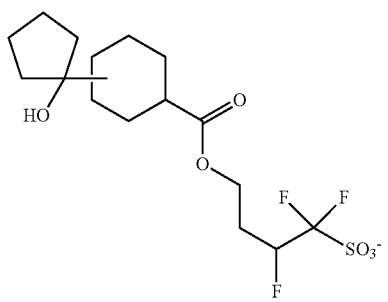
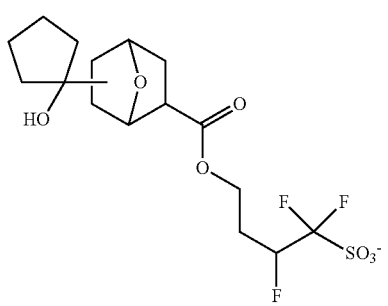
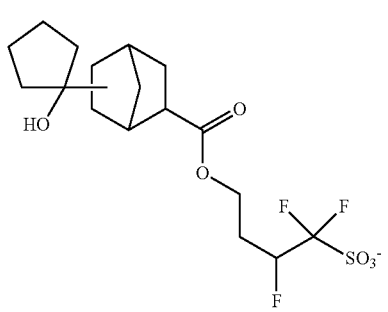
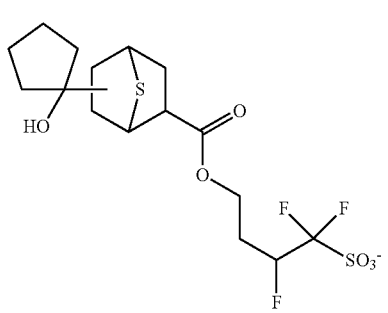
-continued
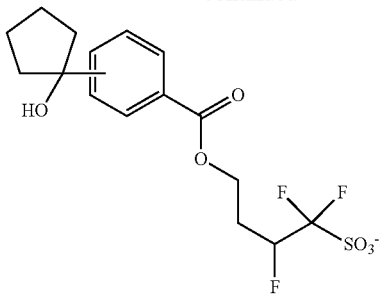
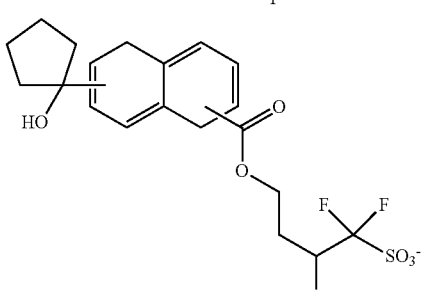
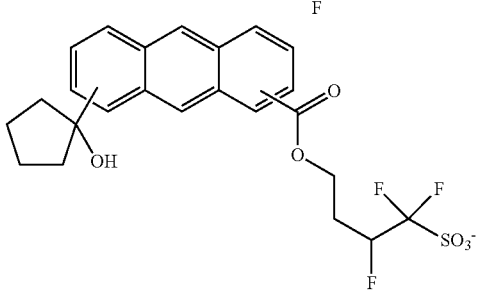
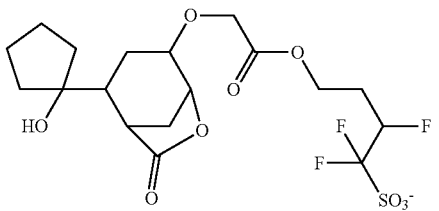
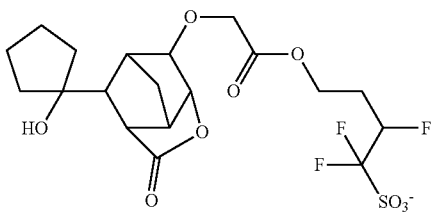
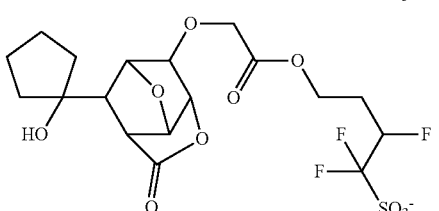
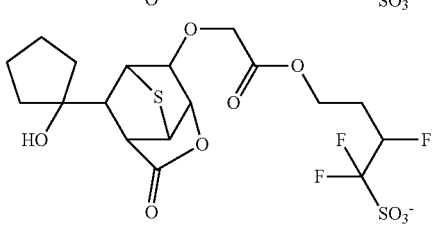

31
-continued
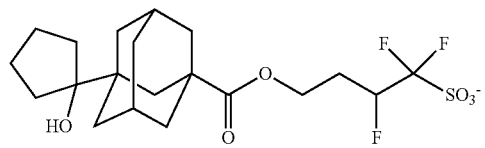
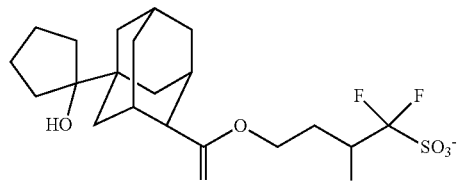
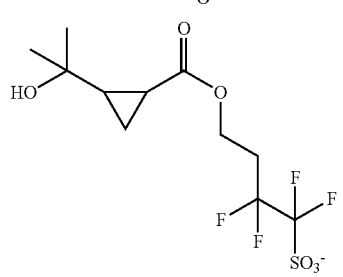
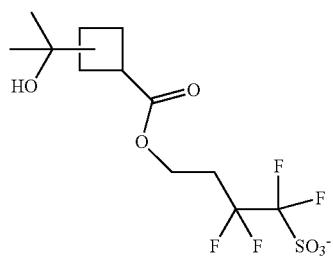
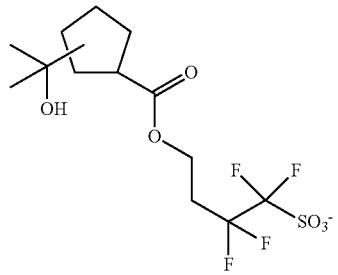
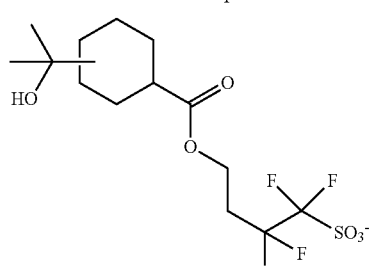
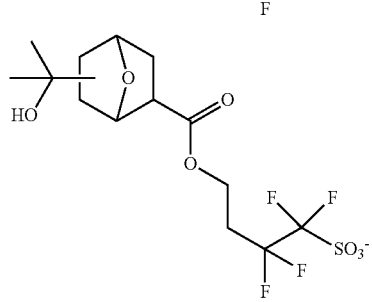
32
-continued
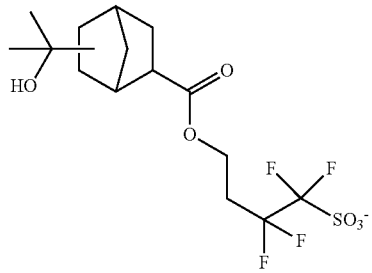
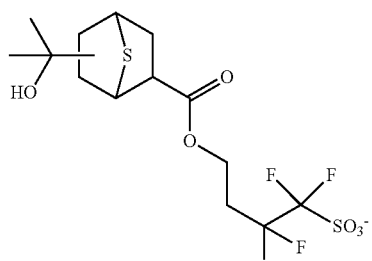
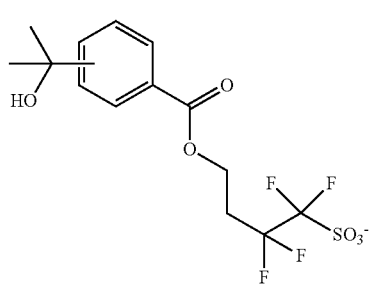
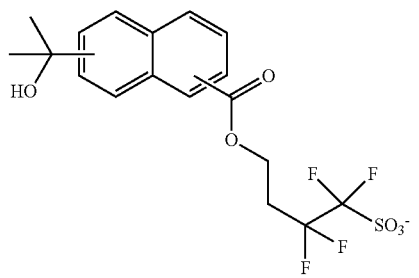
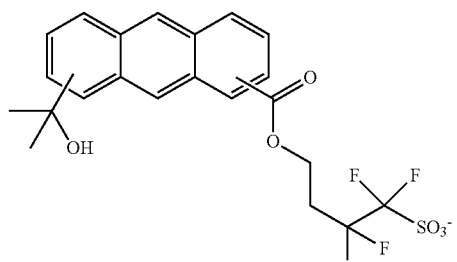
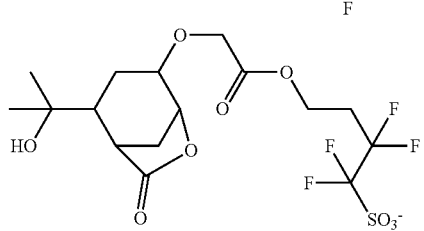

-continued
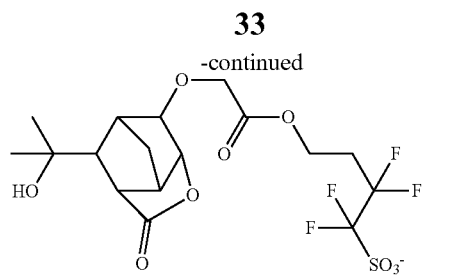
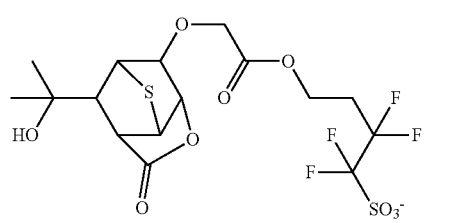
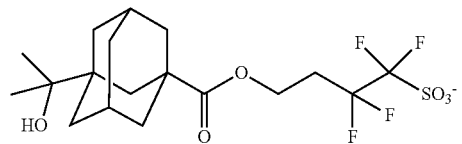
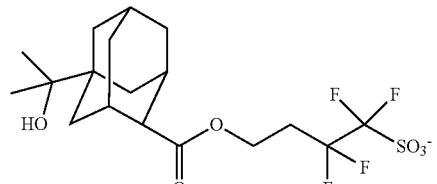
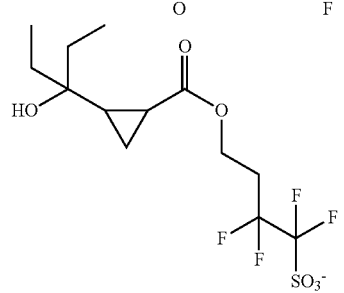
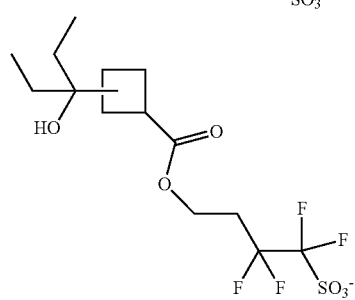
-continued
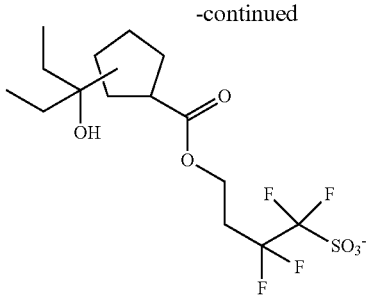
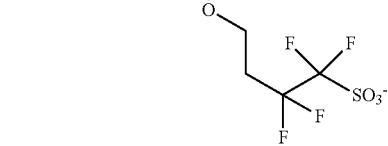
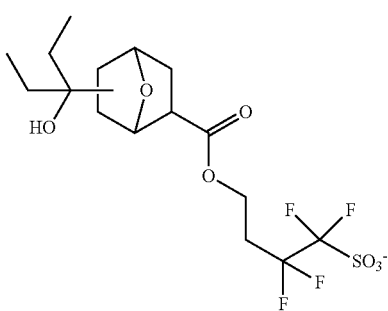
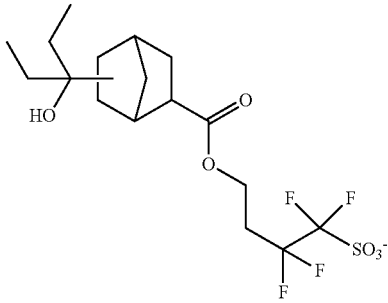
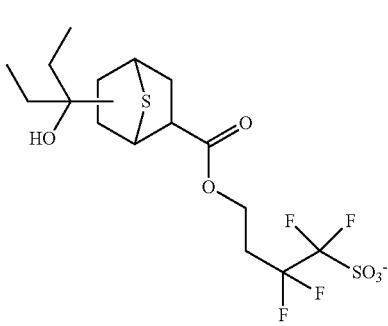

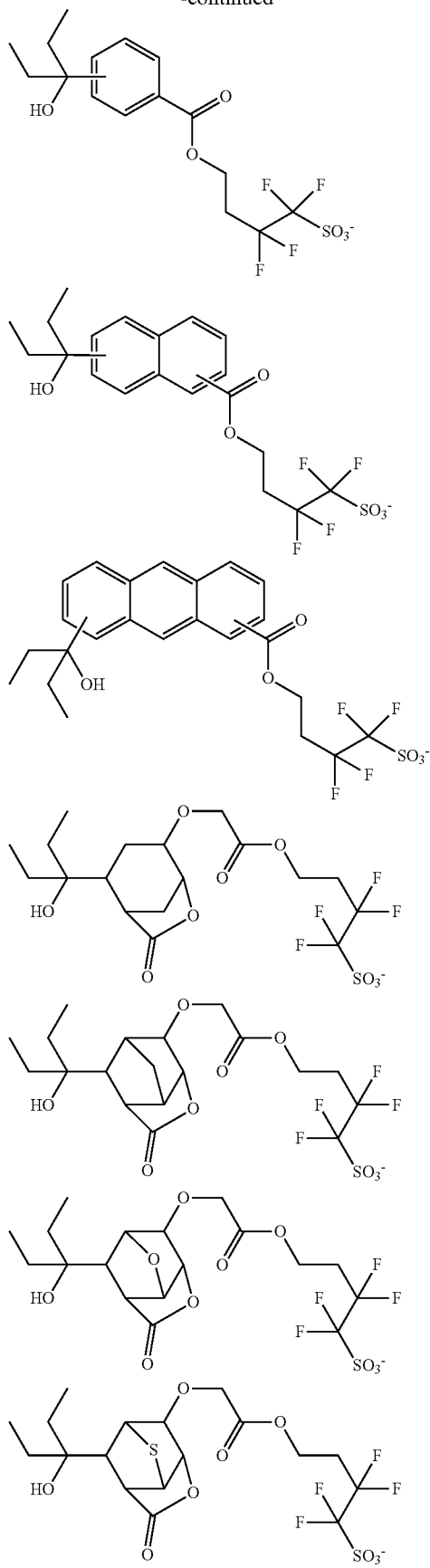
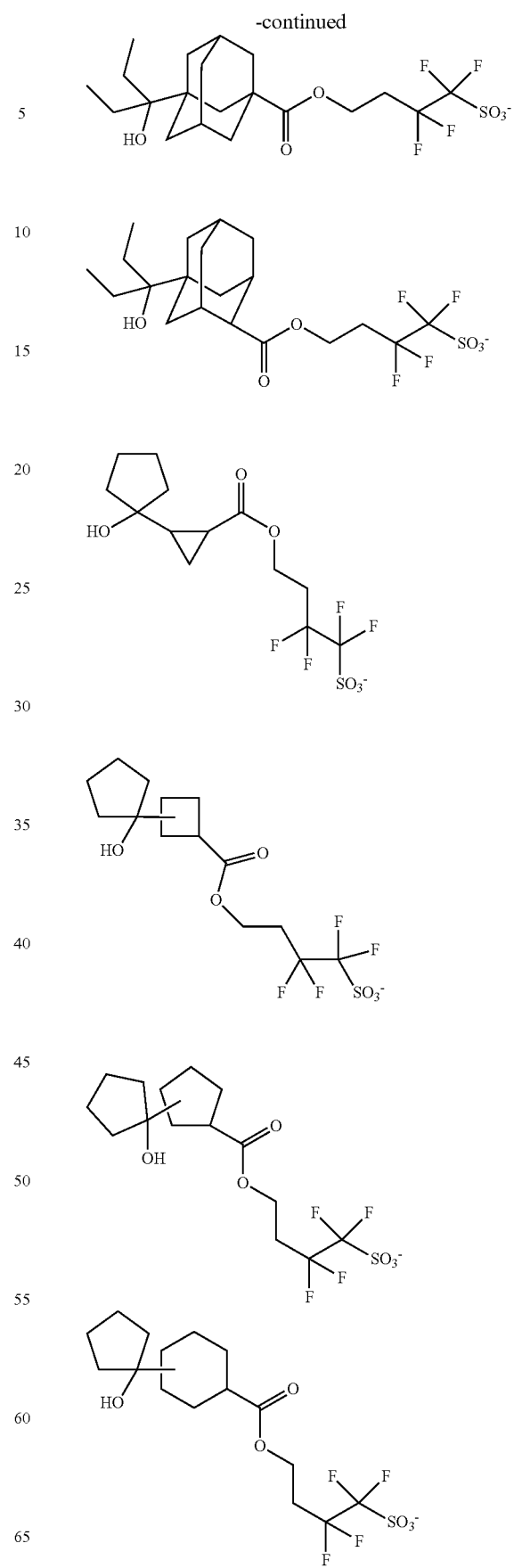

-continued
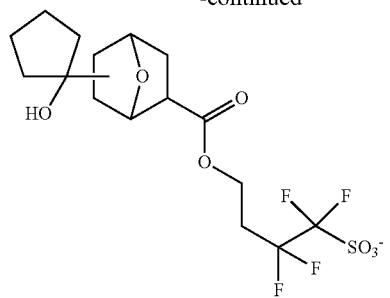
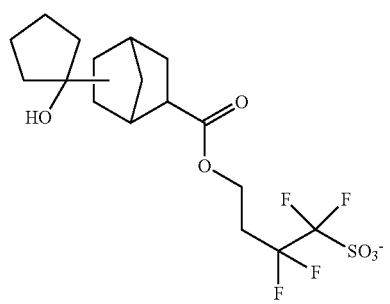
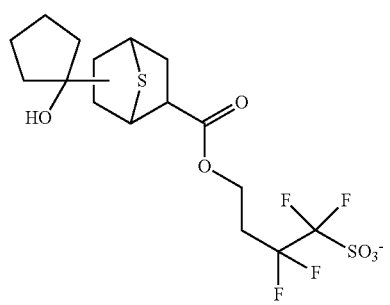
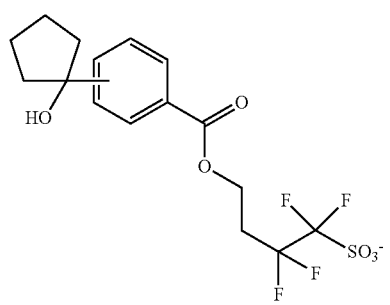
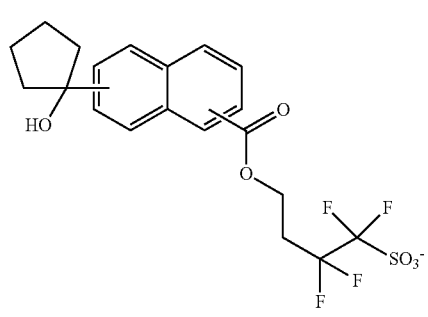
-continued
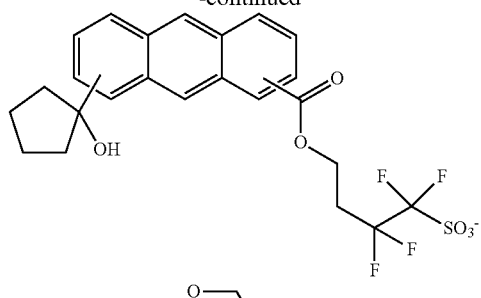
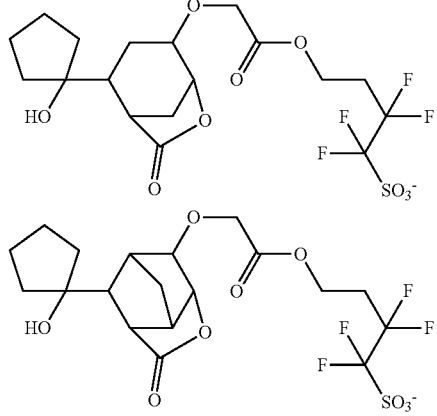
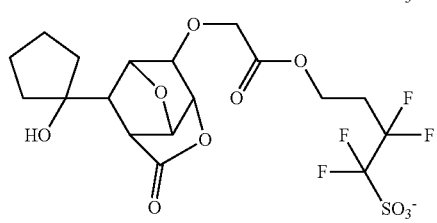
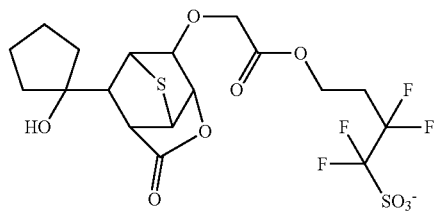
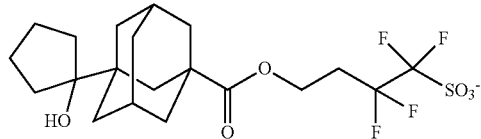
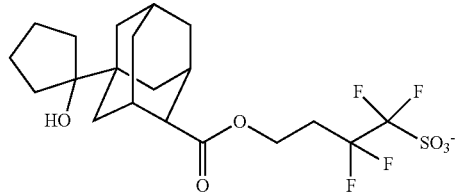
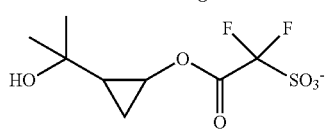
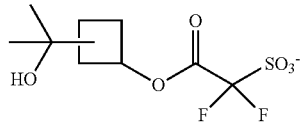

-continued
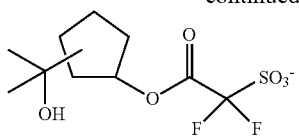
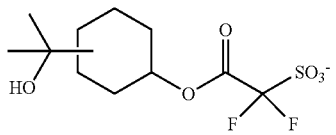
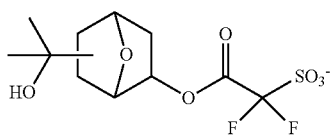
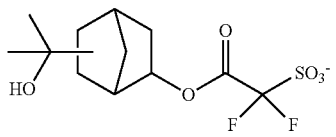
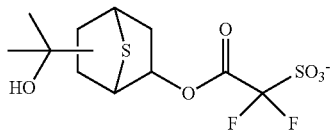
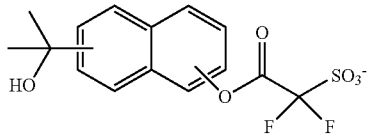
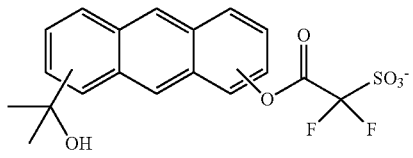
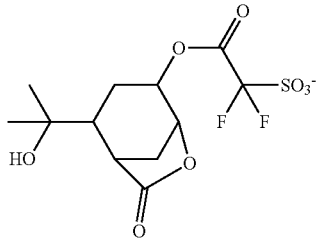
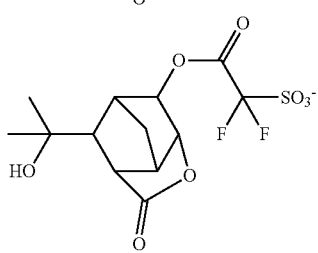
-continued
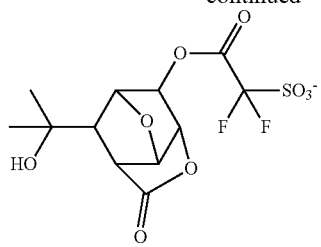
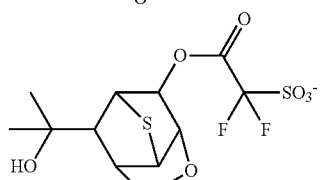
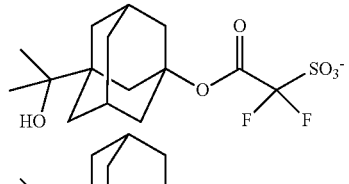
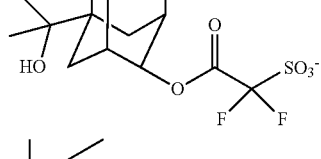
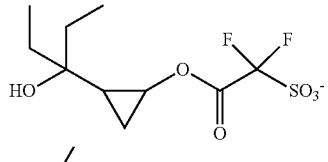
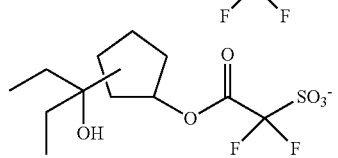
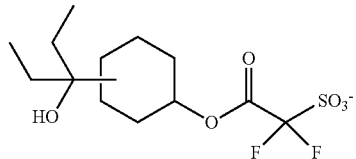
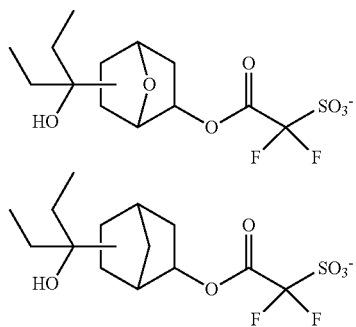

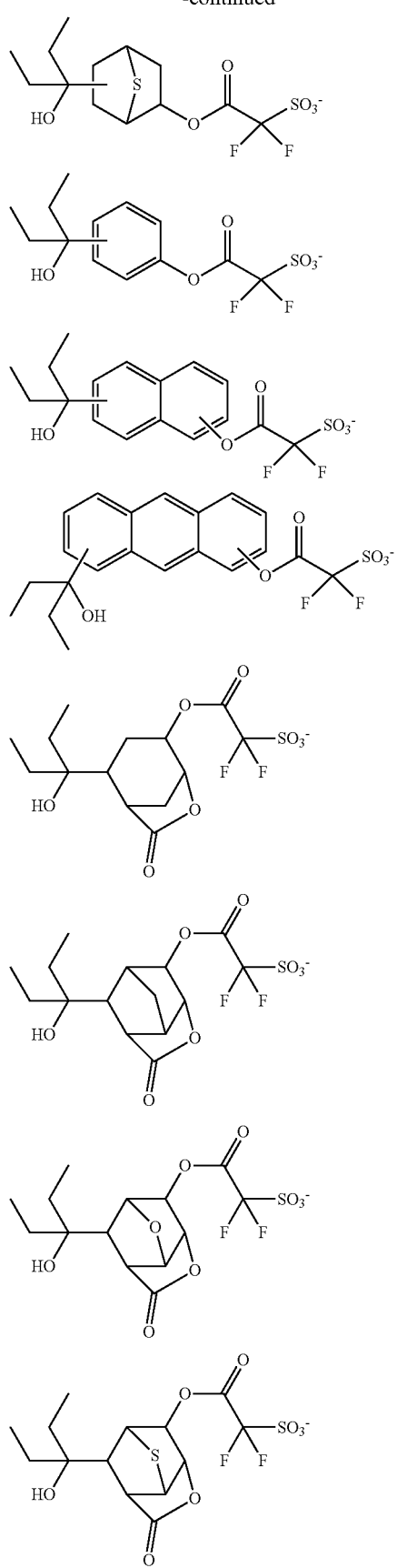
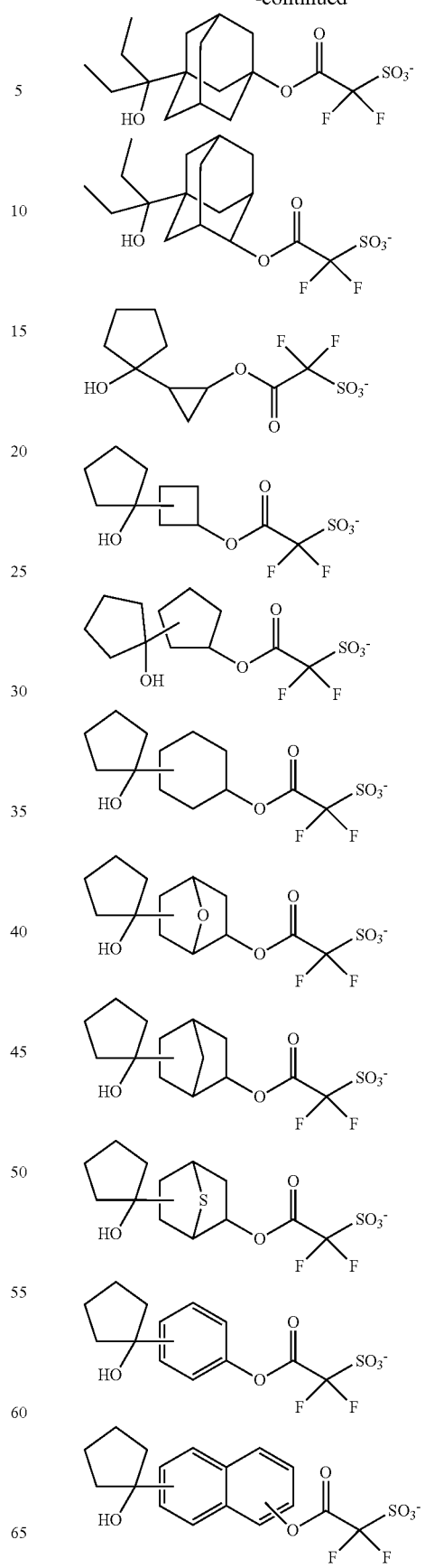

-continued
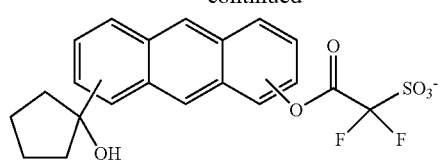
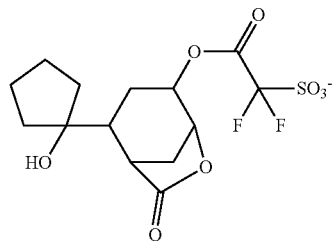
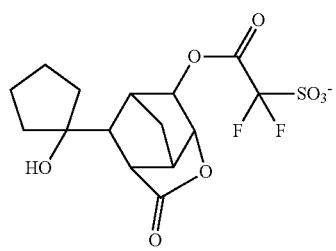
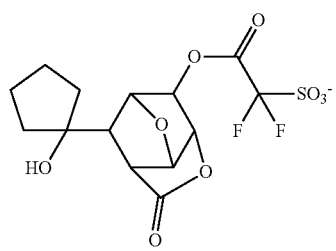
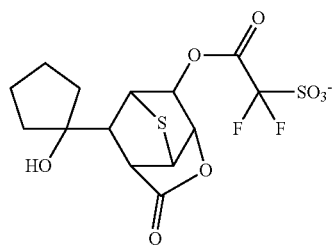
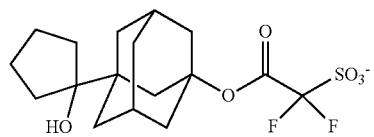
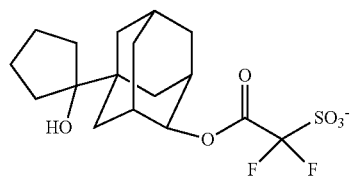
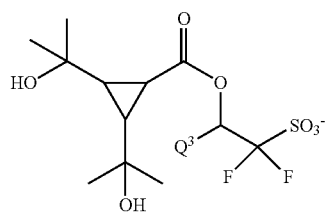
-continued
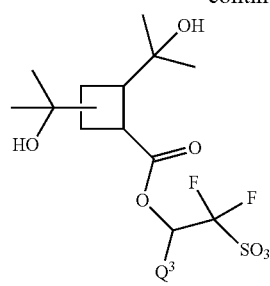
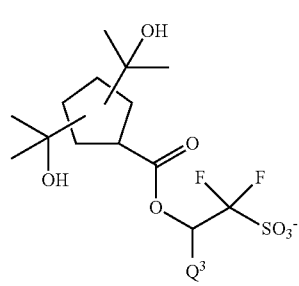
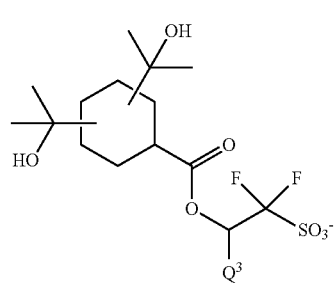
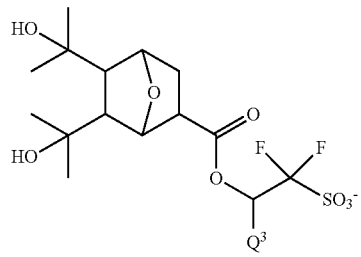
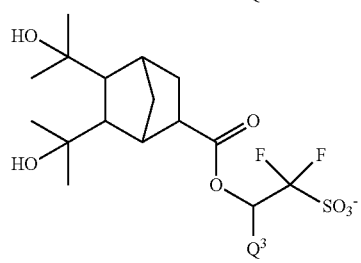
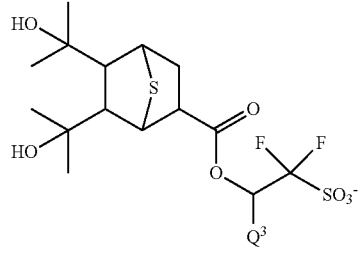

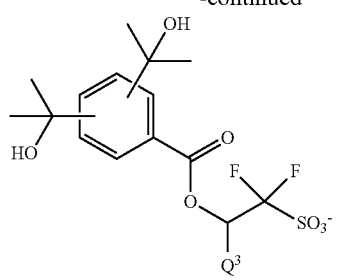
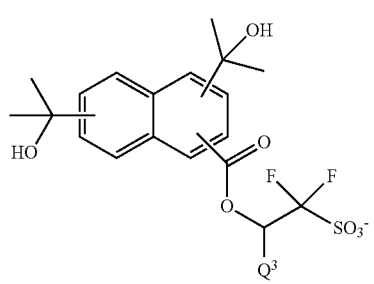
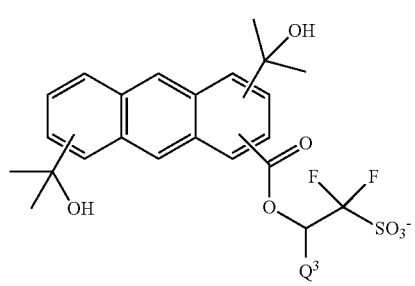
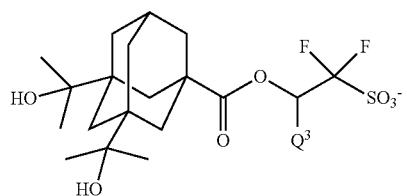
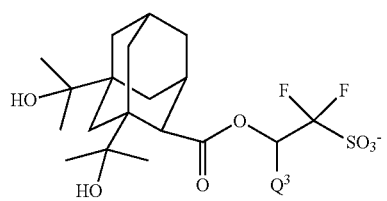
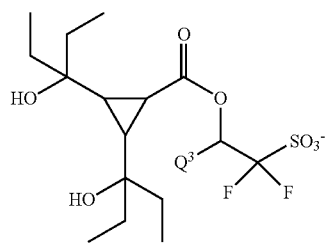
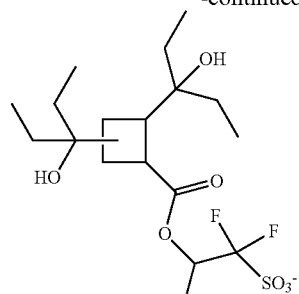
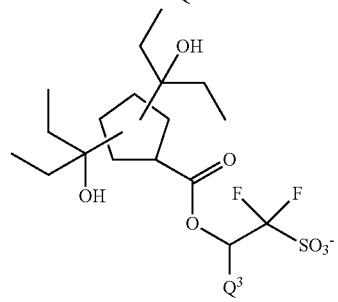
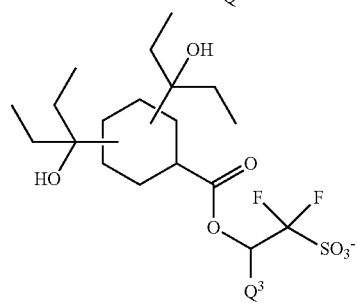
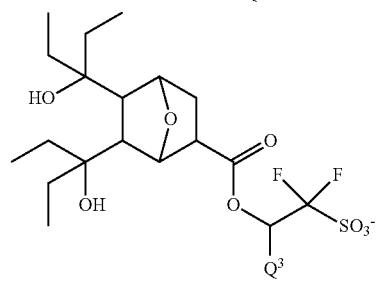
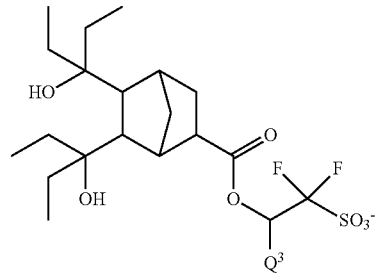
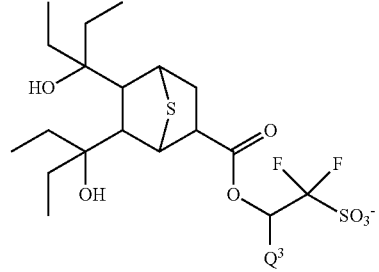

-continued
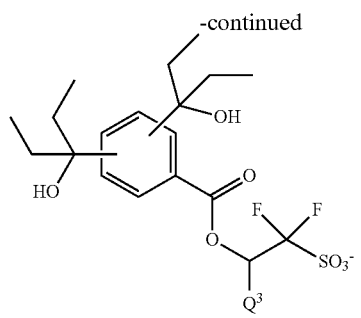
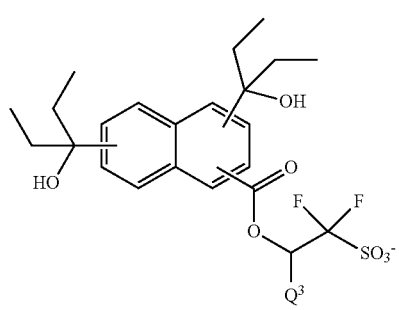
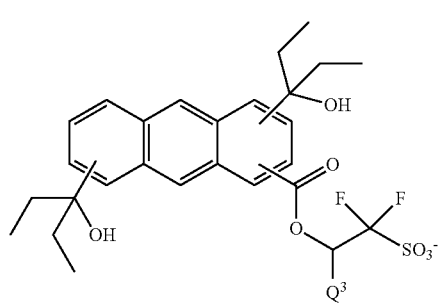
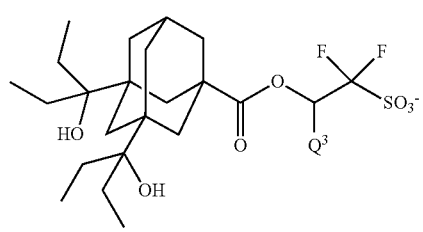
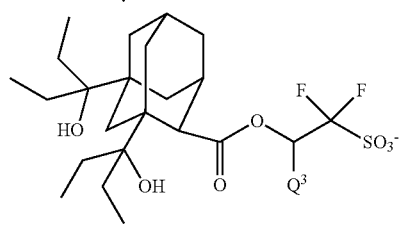
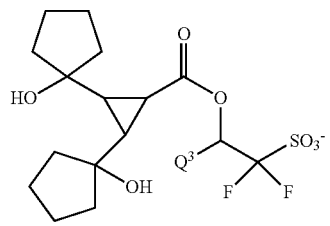
-continued
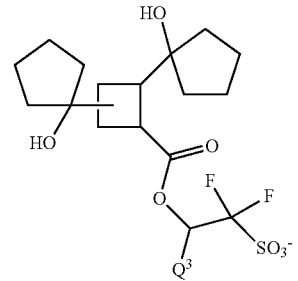
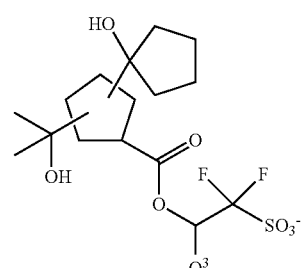
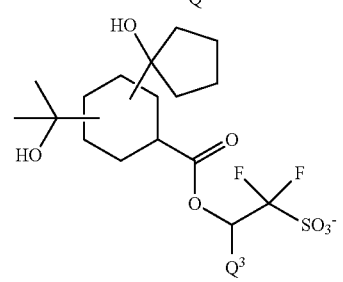
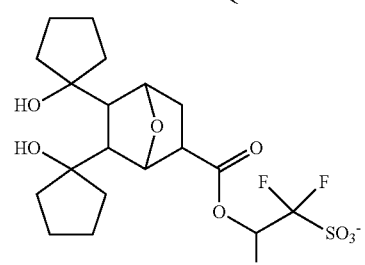
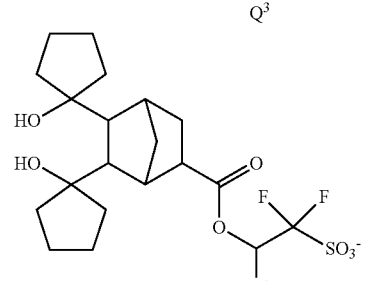
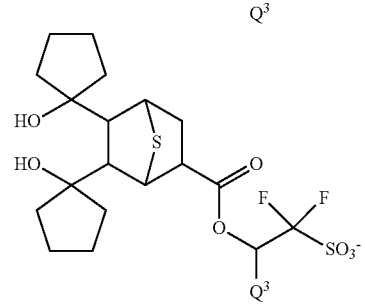

49
-continued
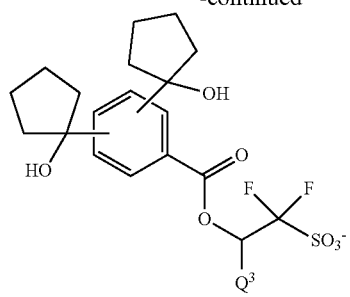
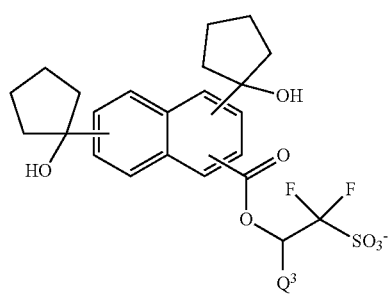
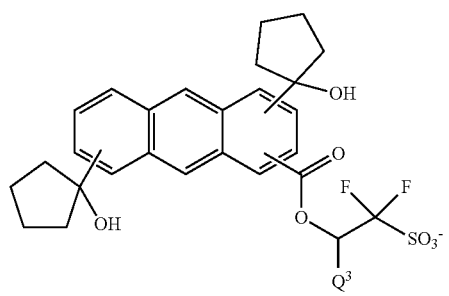
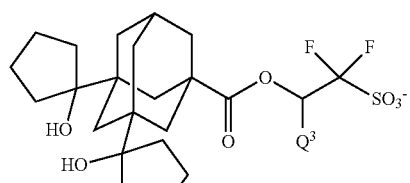
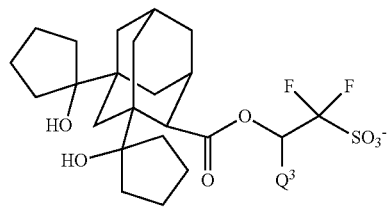
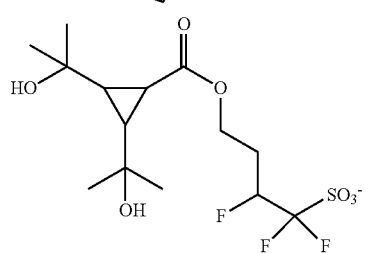
50
-continued
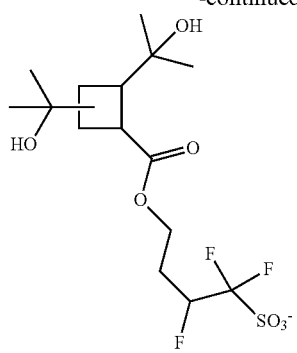
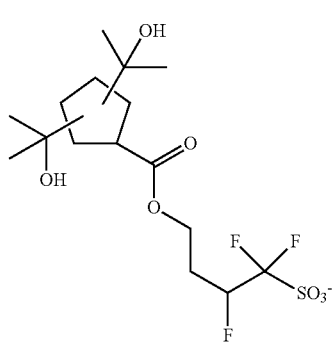
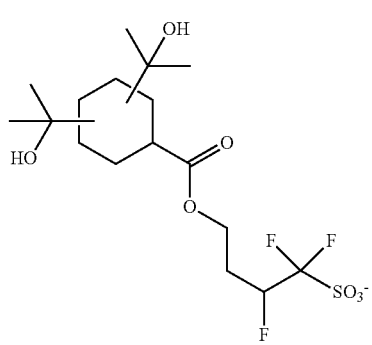
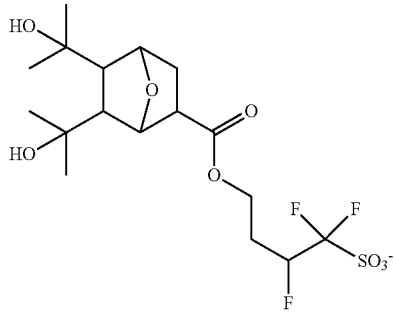
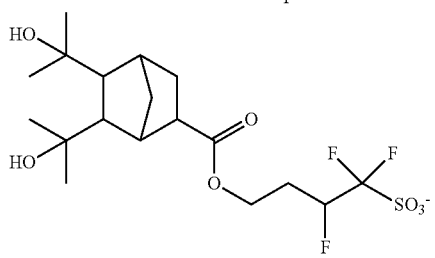

51
-continued
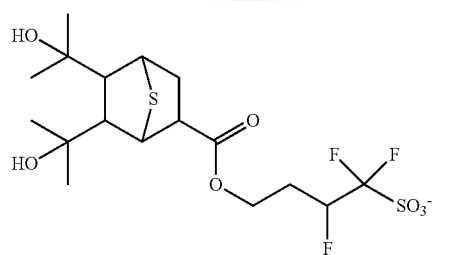
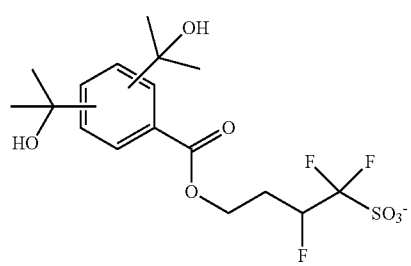
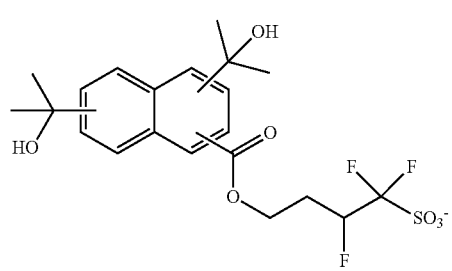
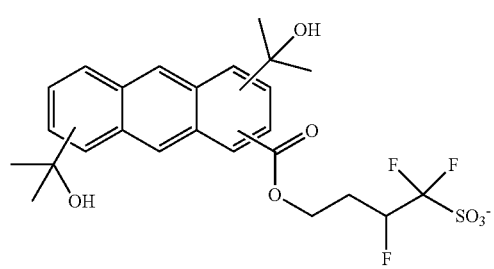
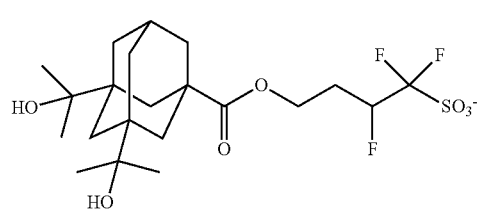
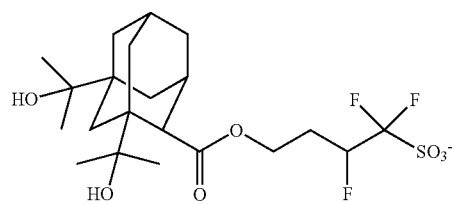
52
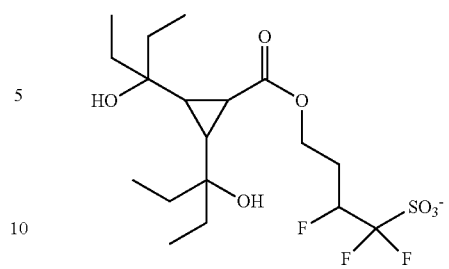
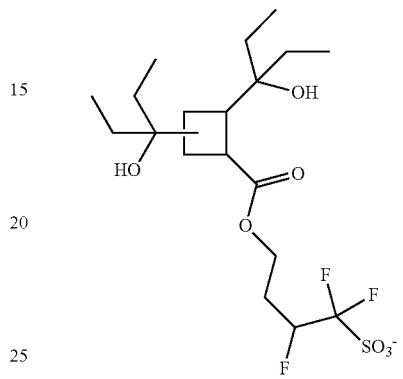
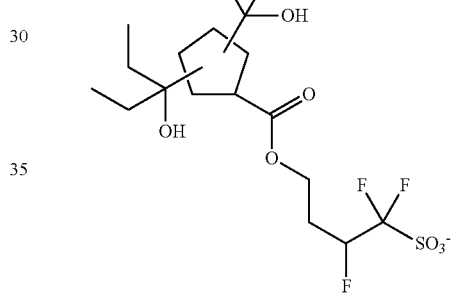
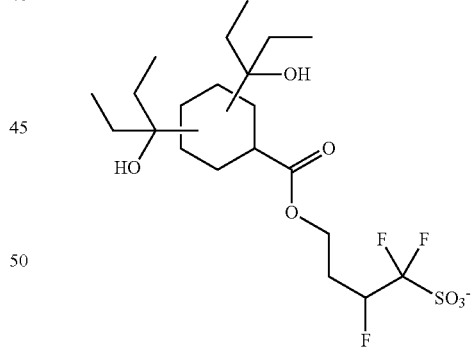
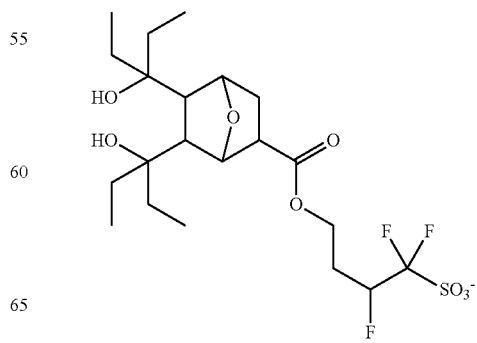

-continued
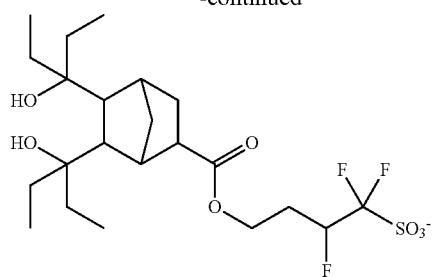
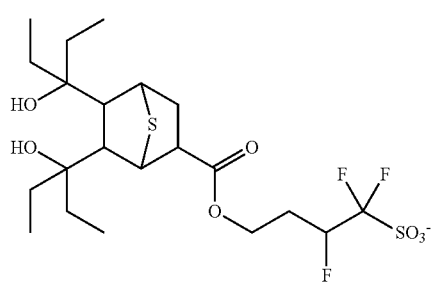
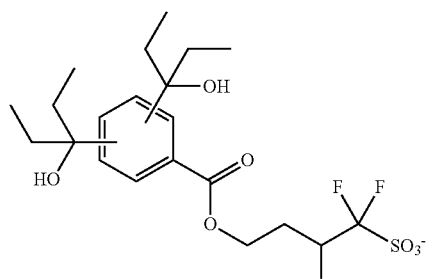
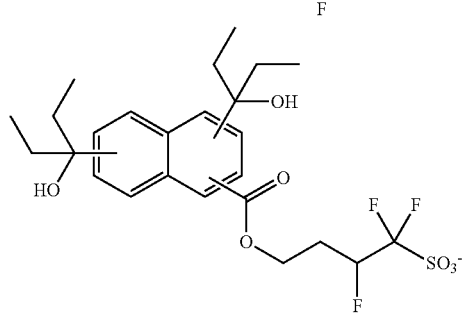
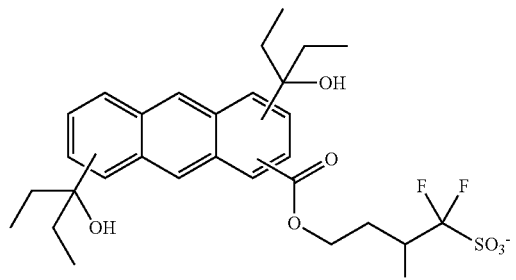
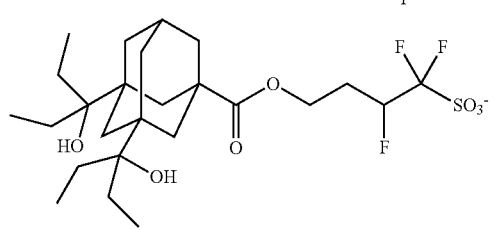
-continued
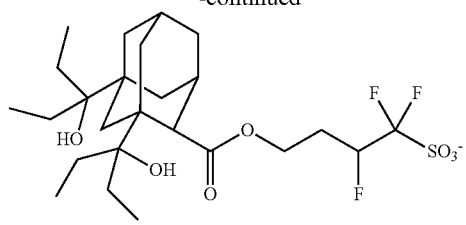
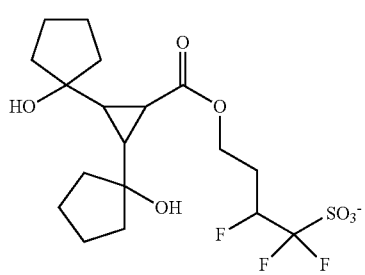
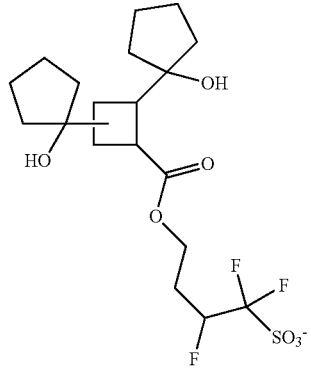
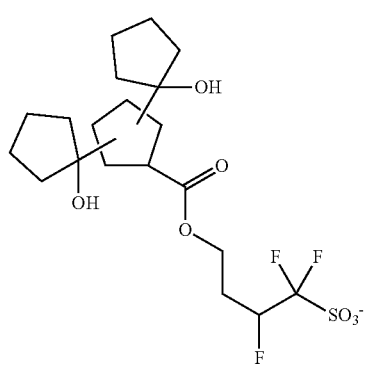
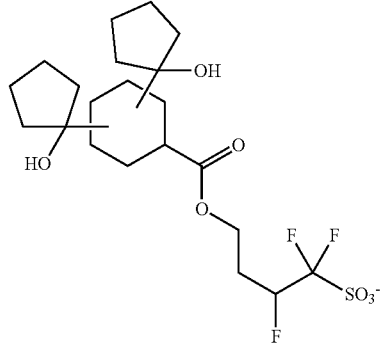

55
-continued
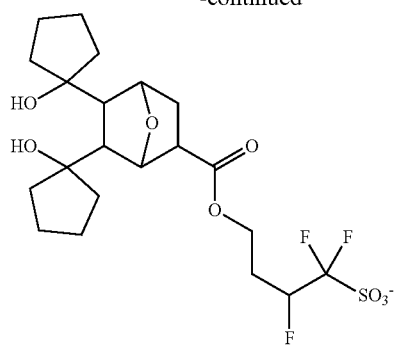
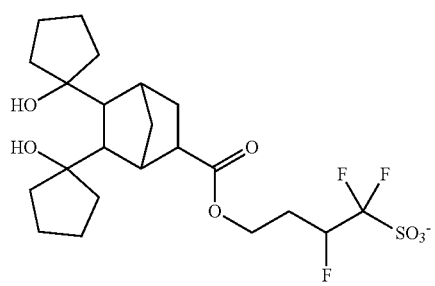
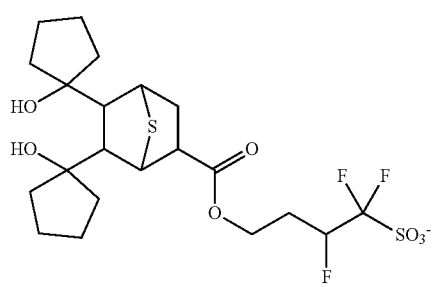
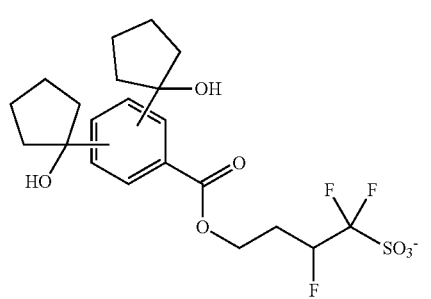
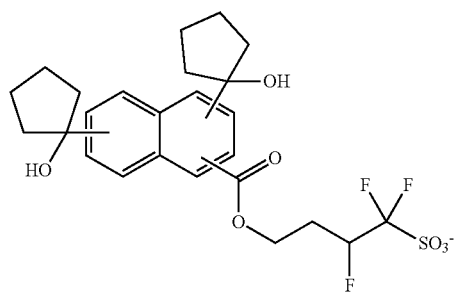
56
-continued
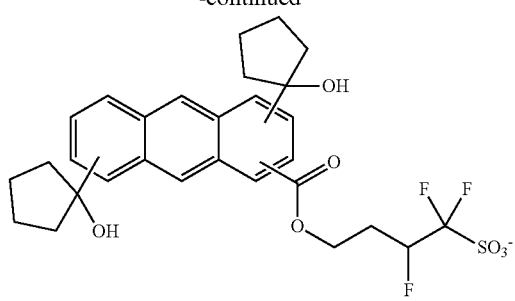
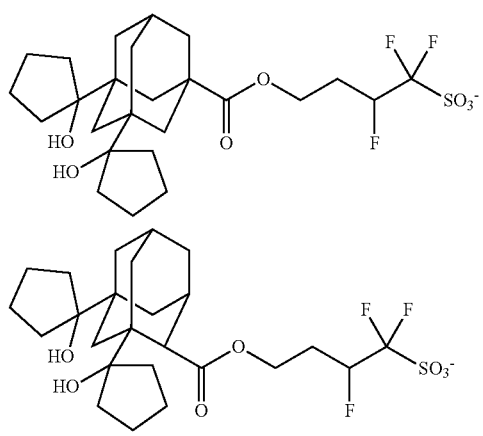
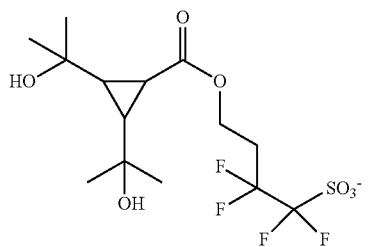
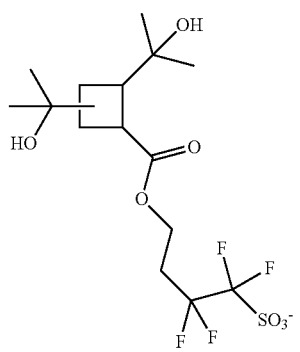
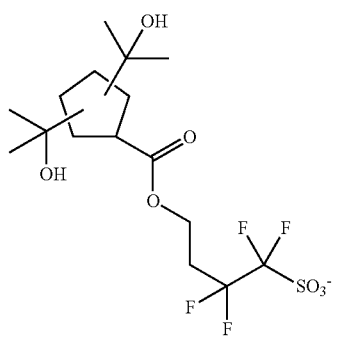

57
-continued
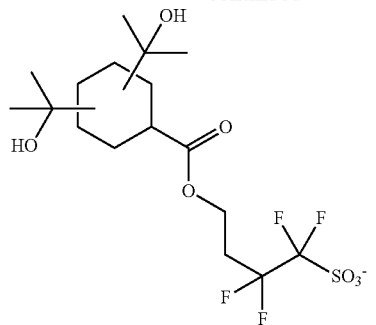
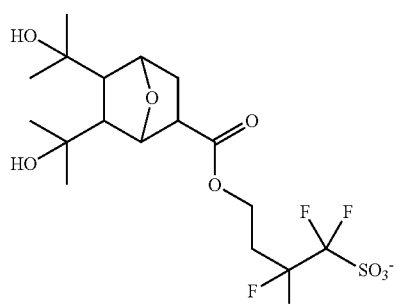
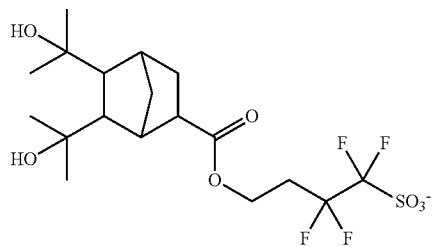
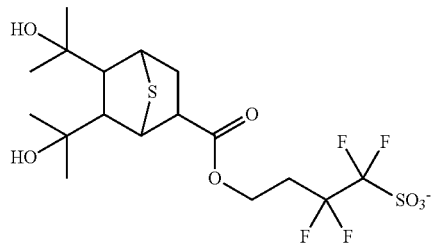
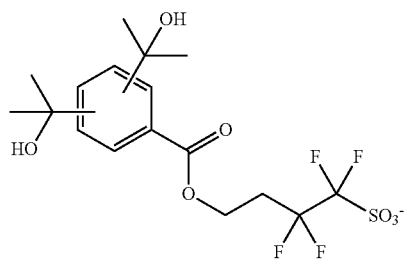
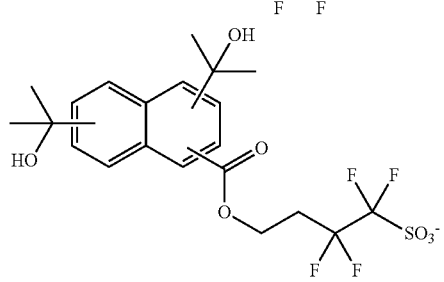
58
-continued
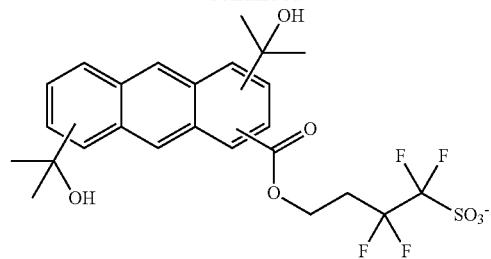
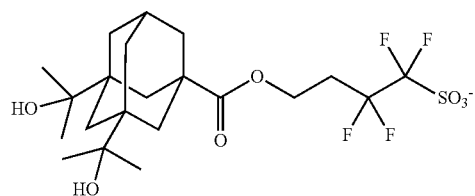
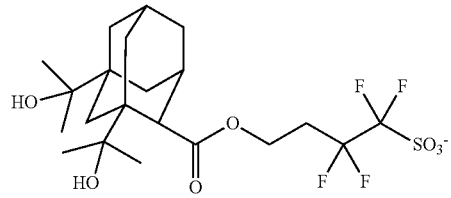
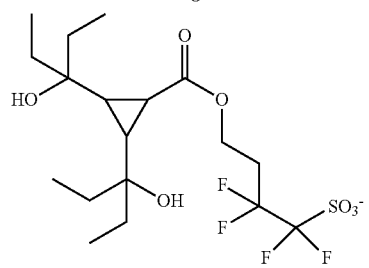
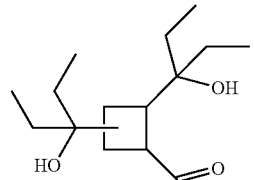
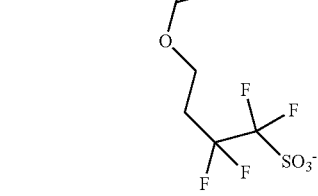
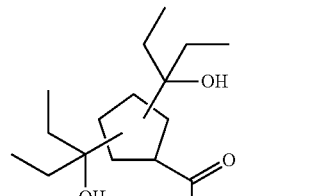
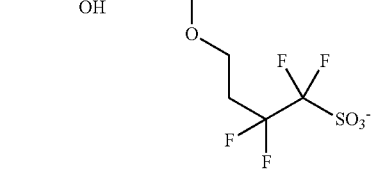

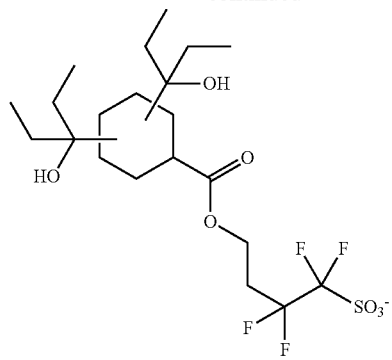
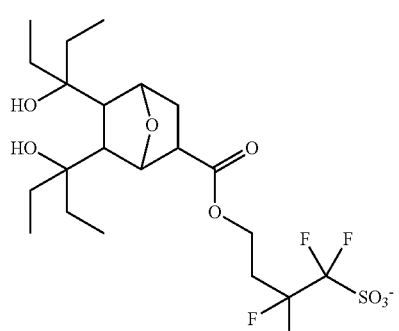
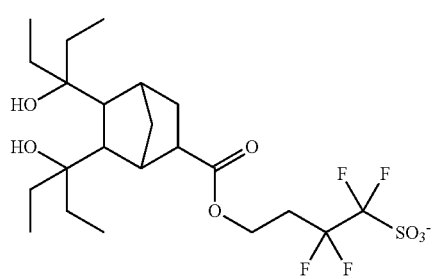
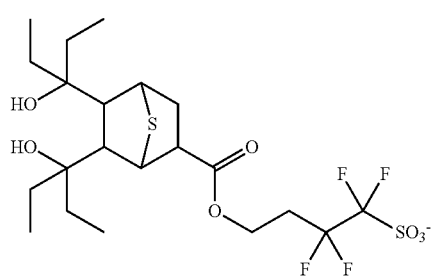
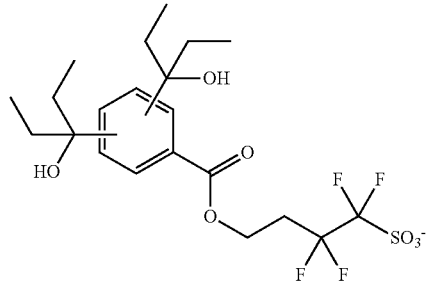
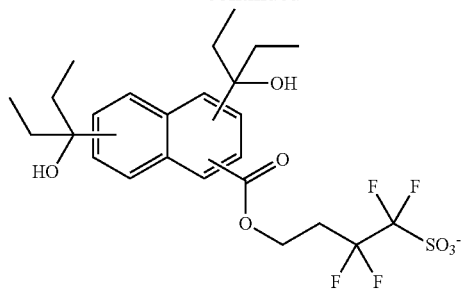
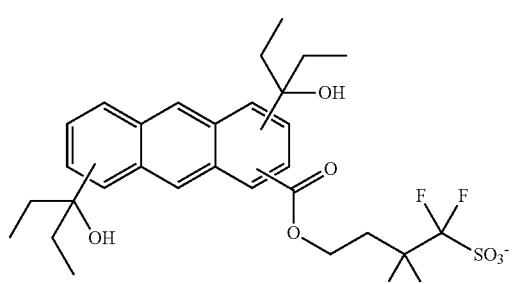
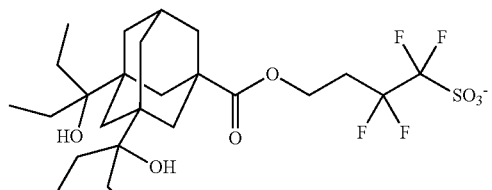
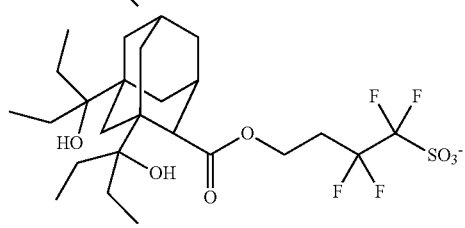
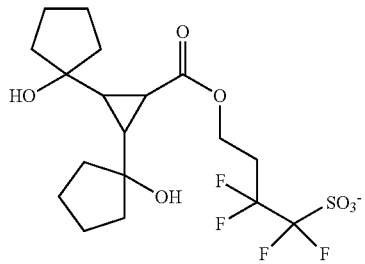
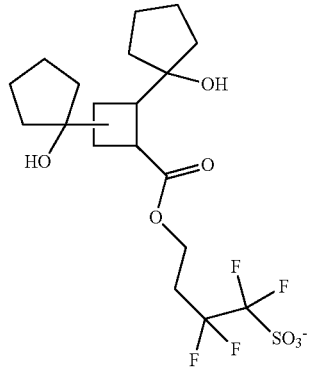

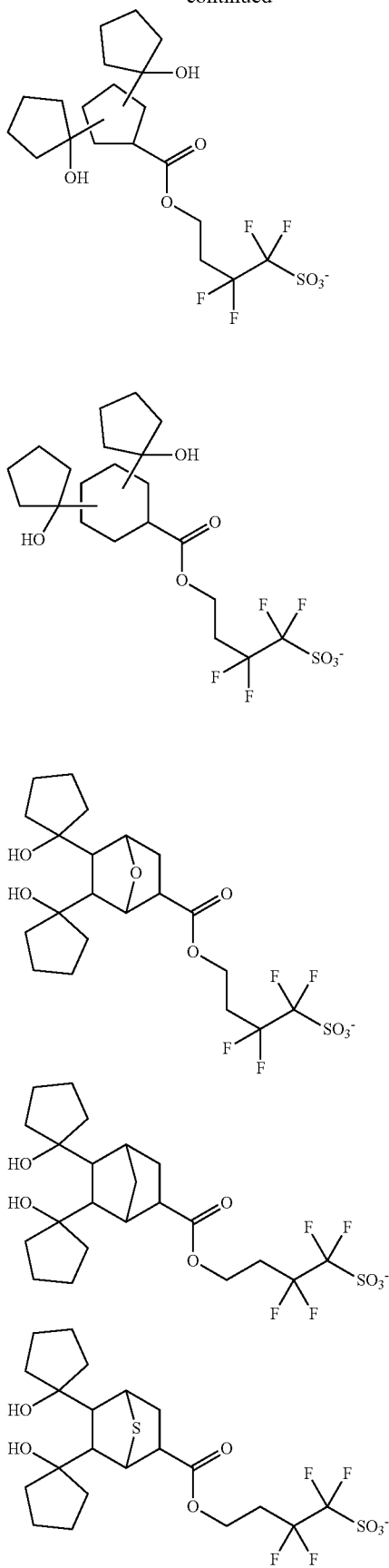
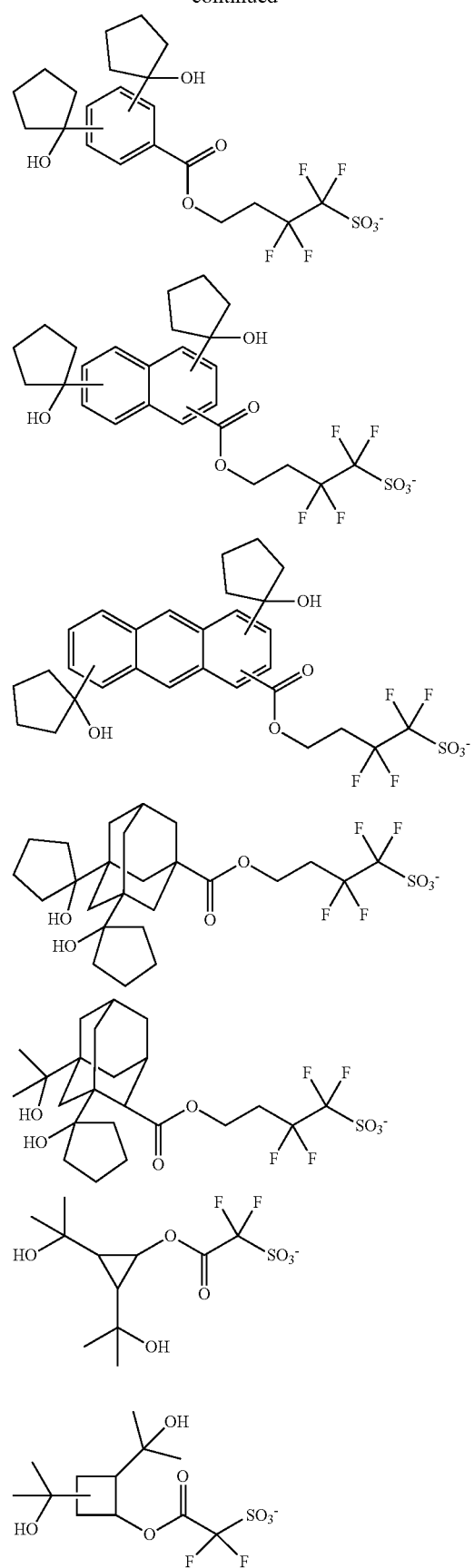

-continued
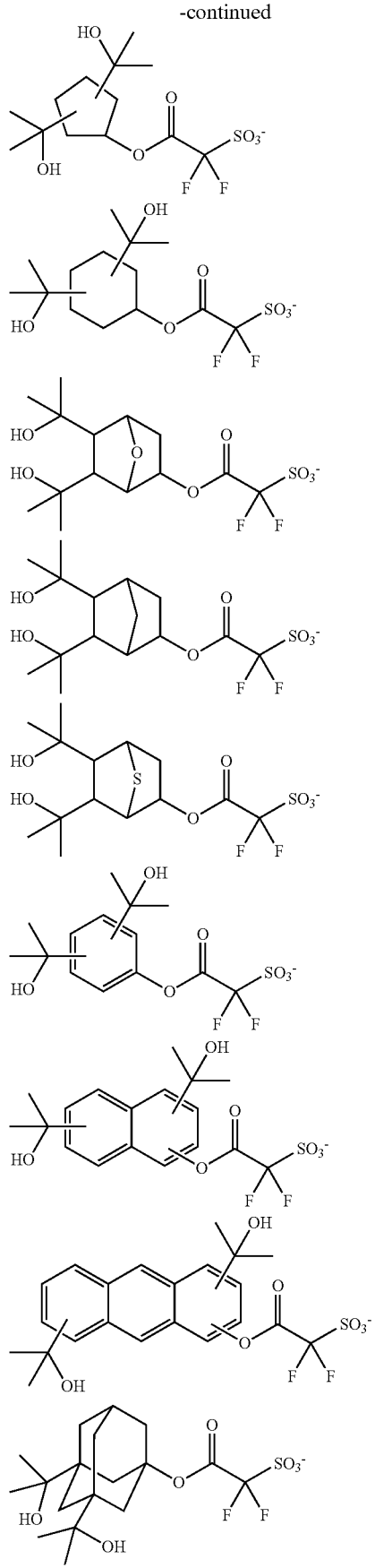
-continued
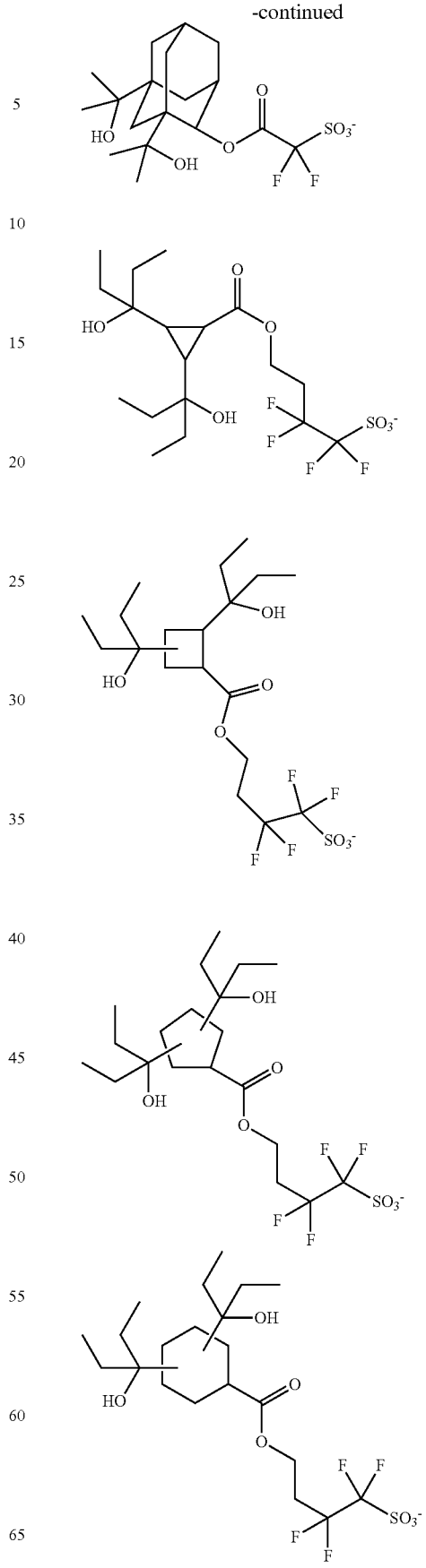

-continued
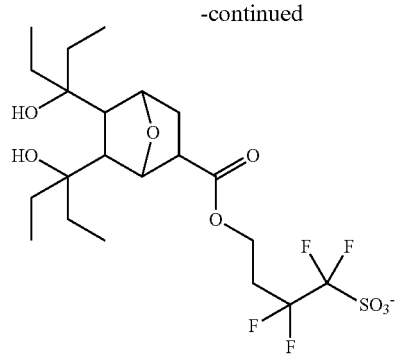
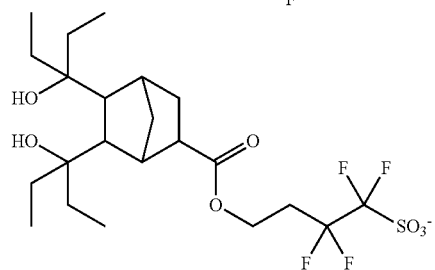
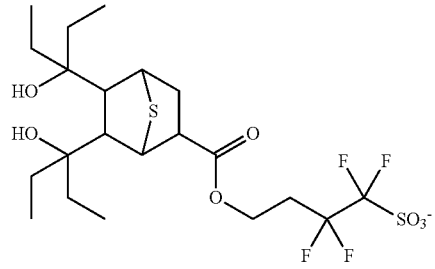
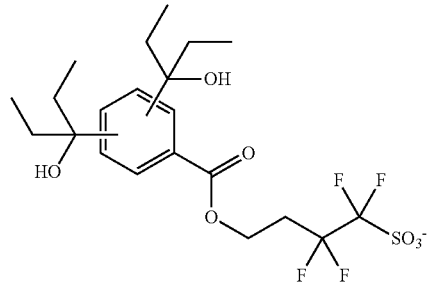
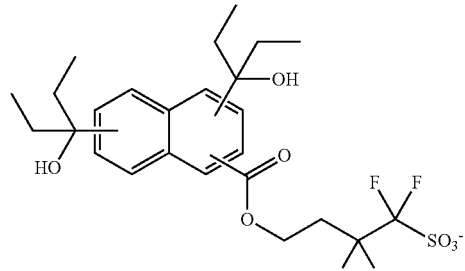
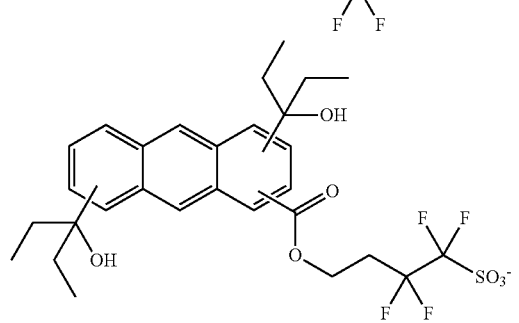
-continued
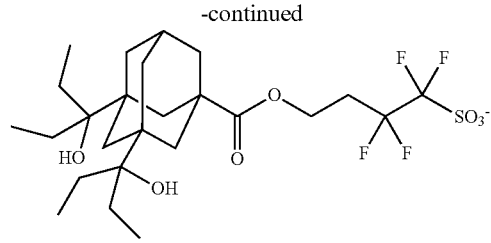
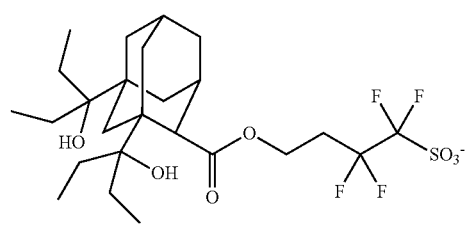
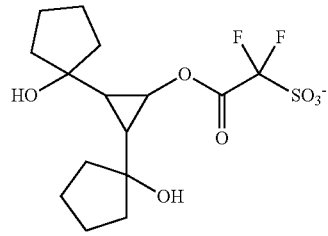
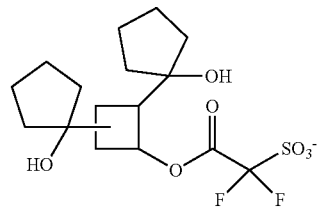
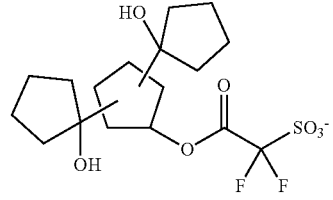
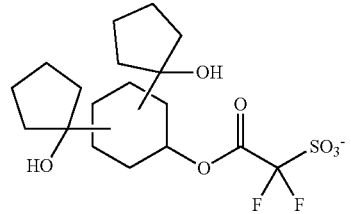
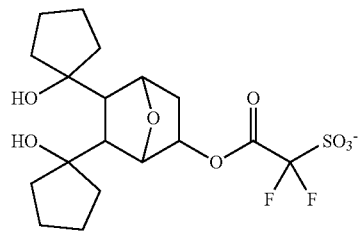

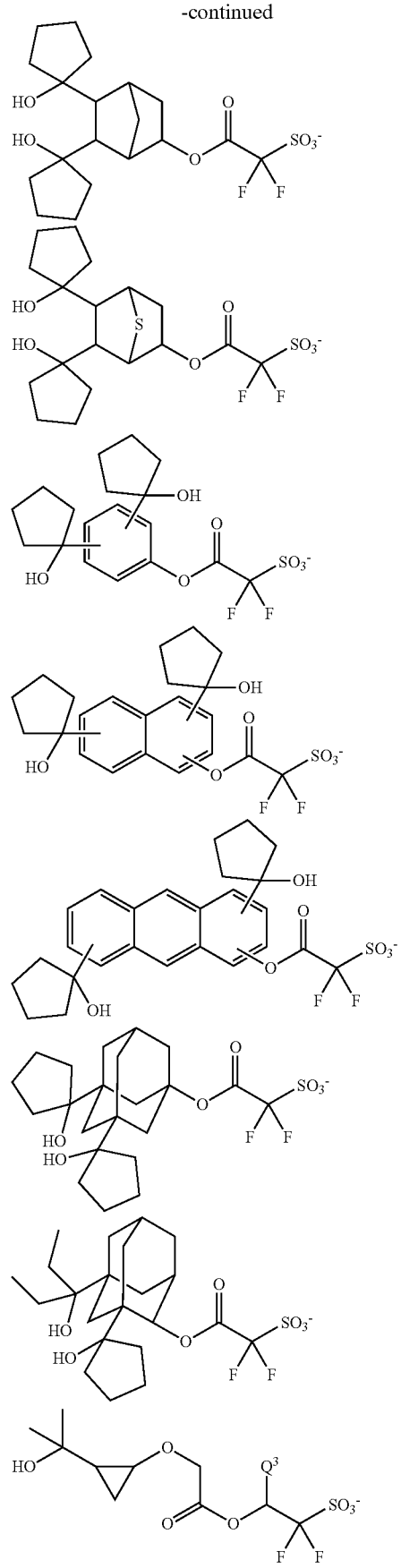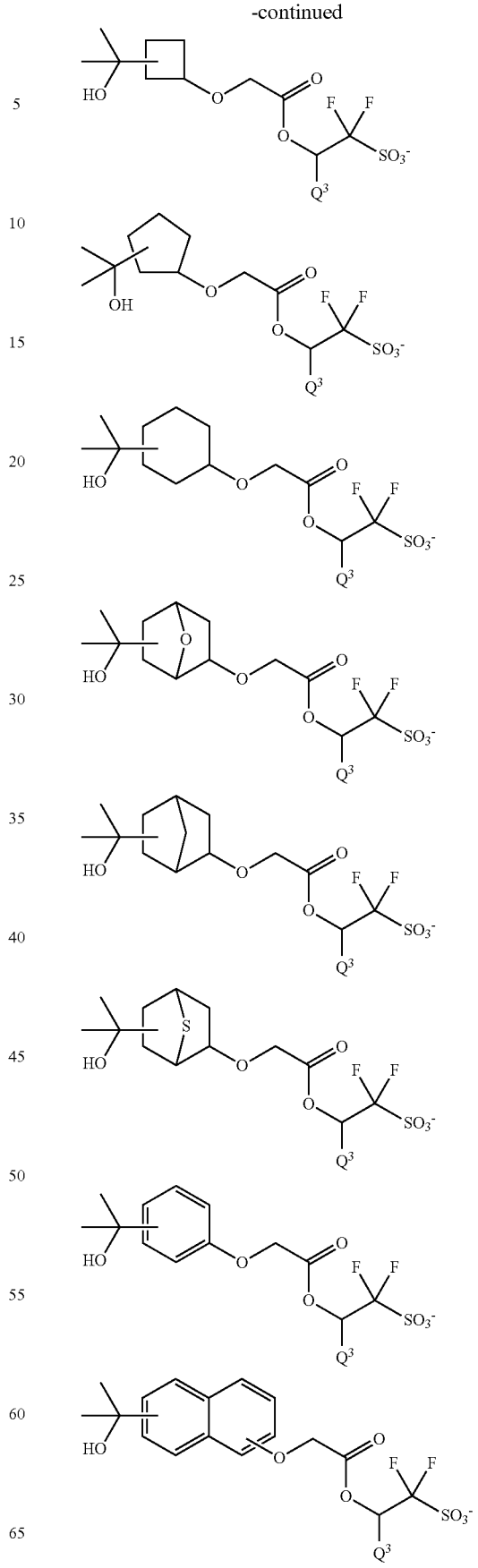

69
-continued
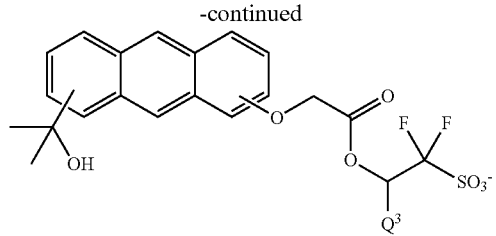
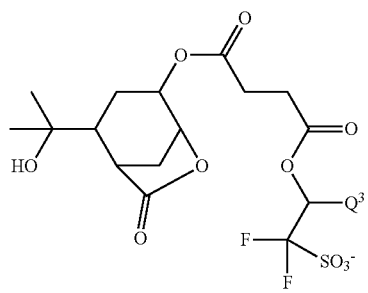
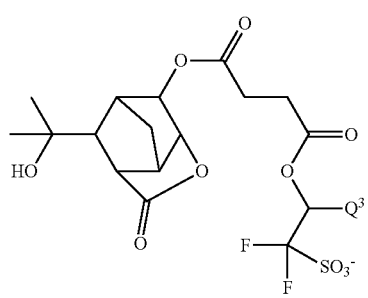
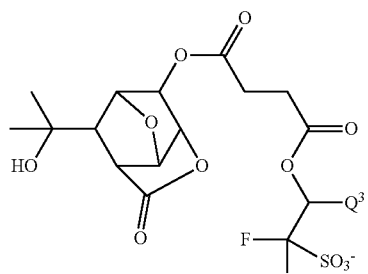
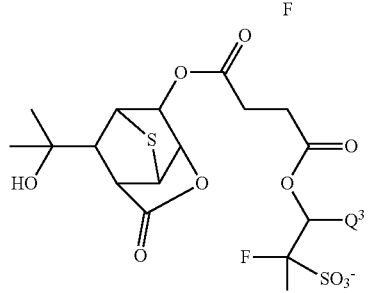
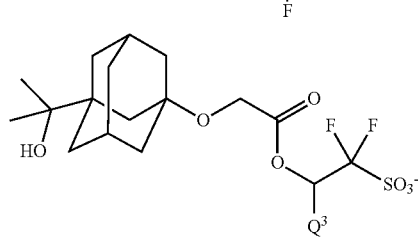
70
-continued
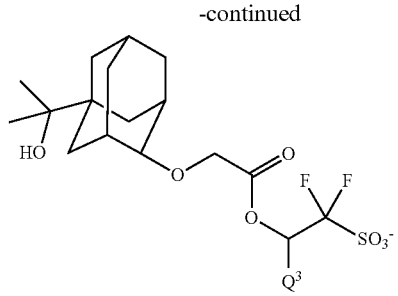
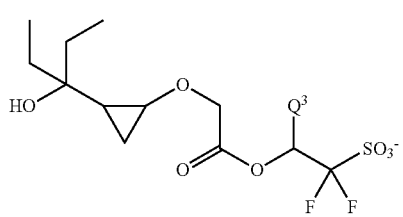
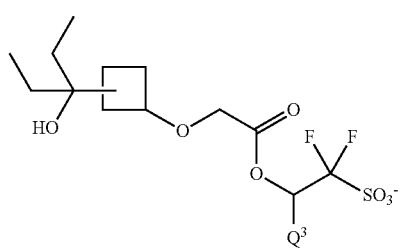
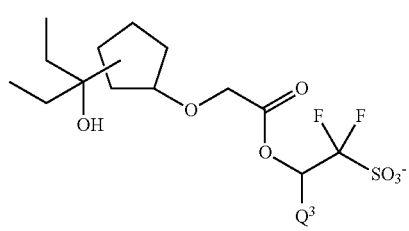
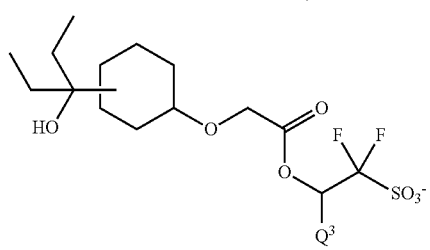
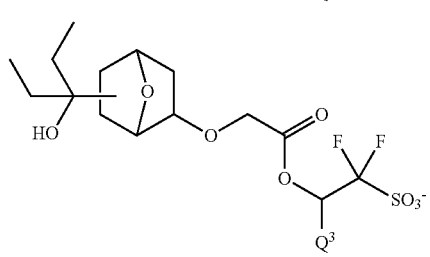

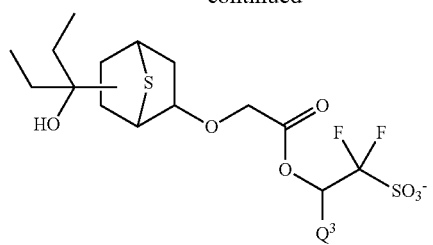
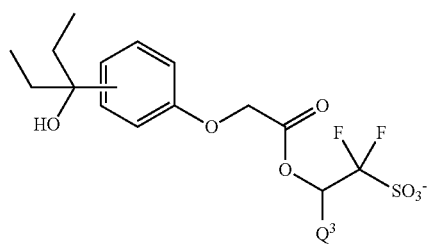
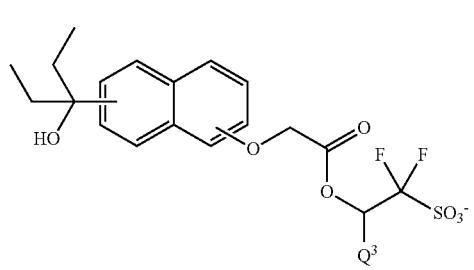
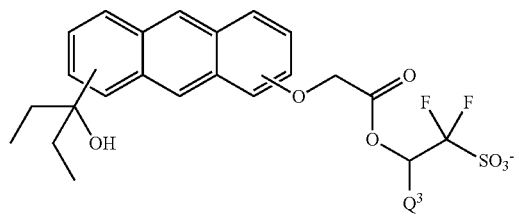
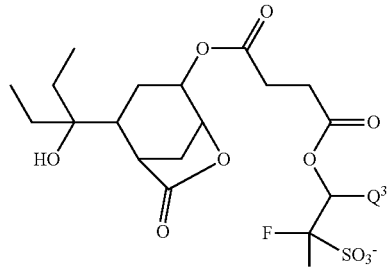
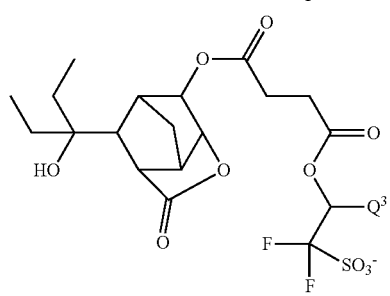
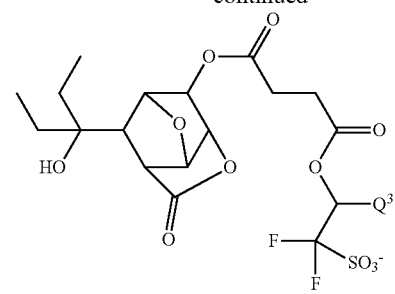
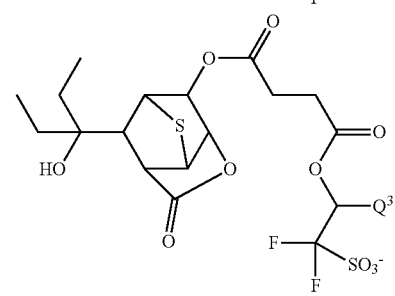
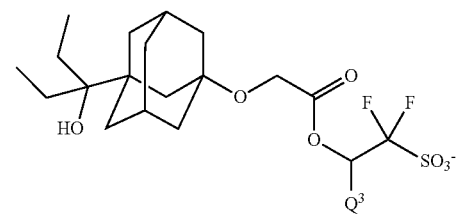
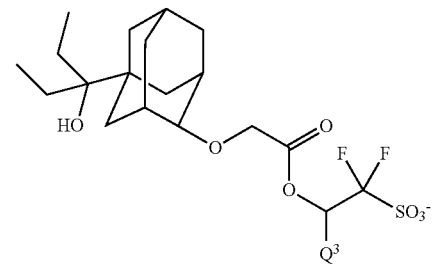
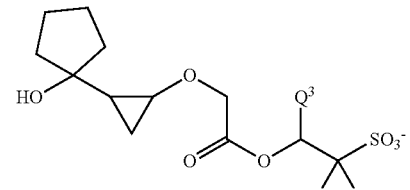
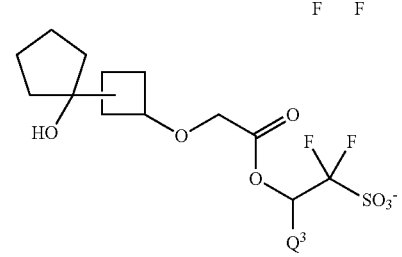
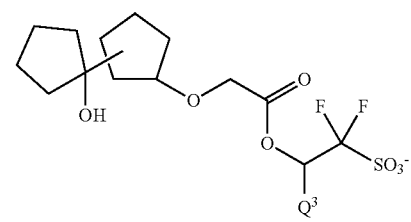

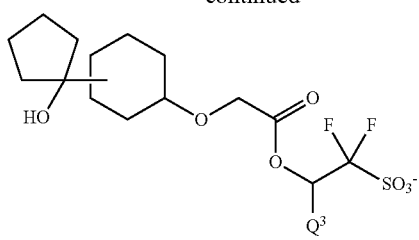
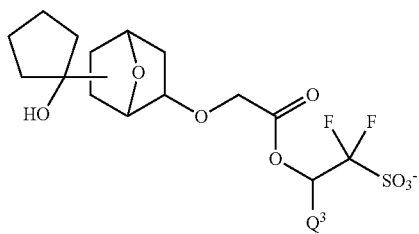
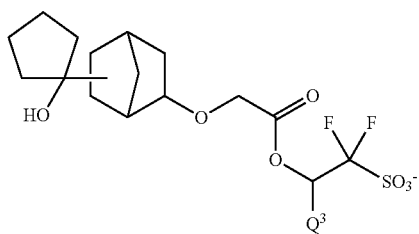
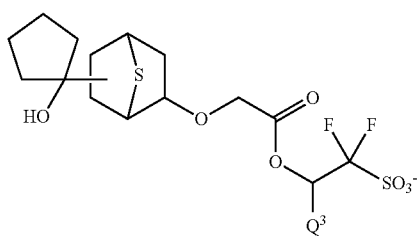
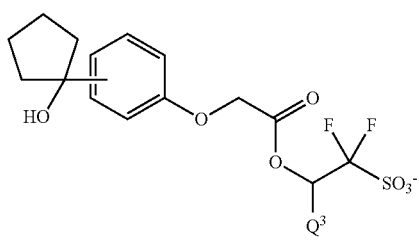
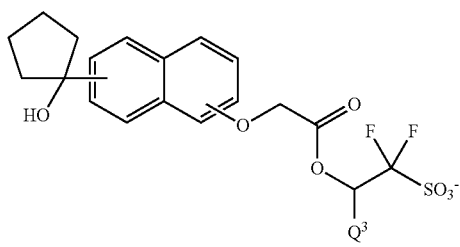
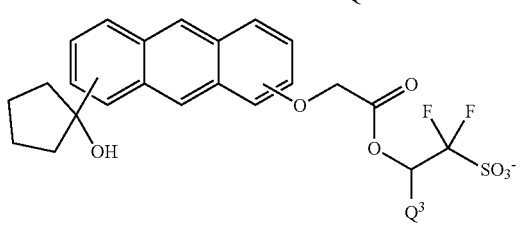
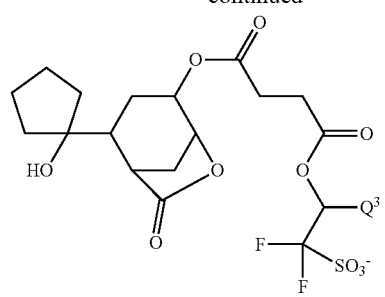
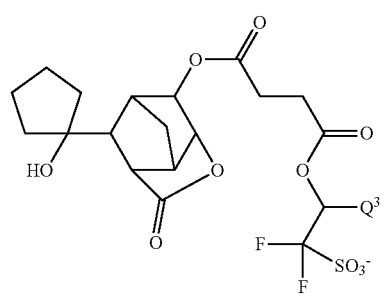
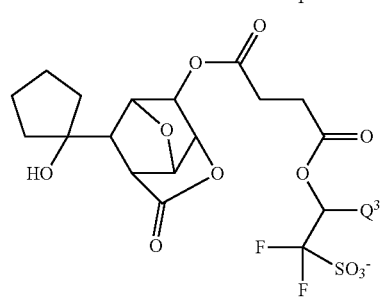
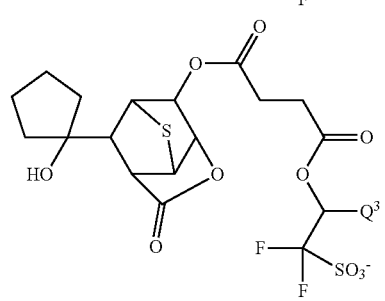
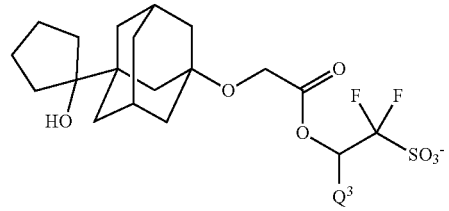
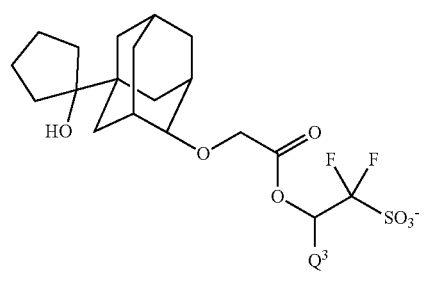

75
-continued
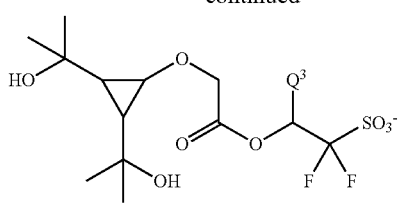
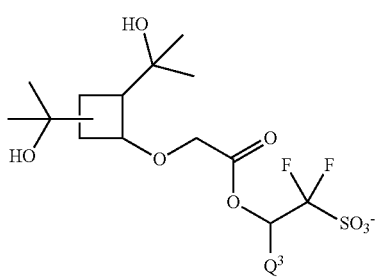
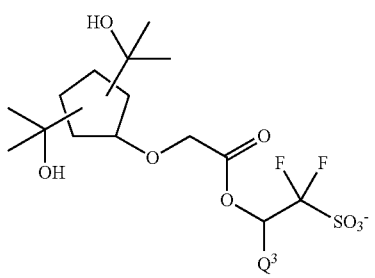
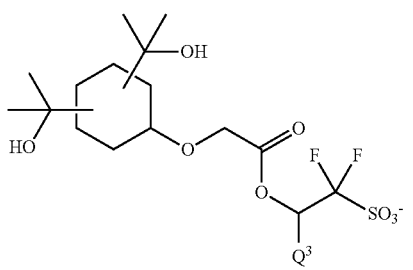
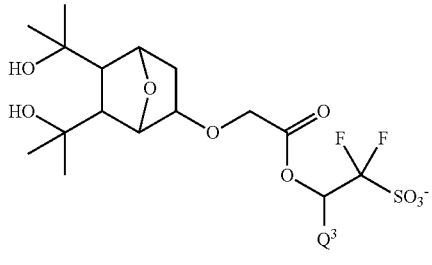
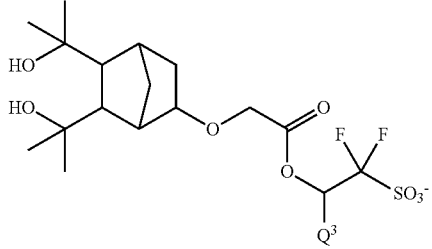
76
-continued
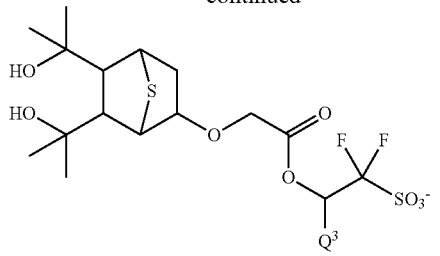
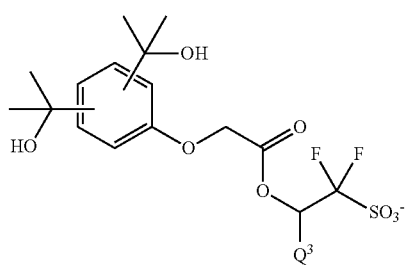
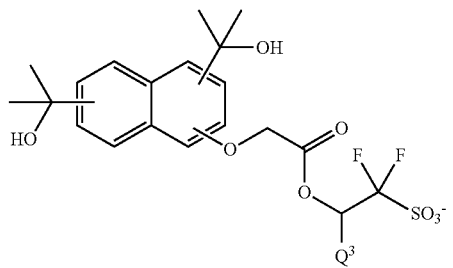
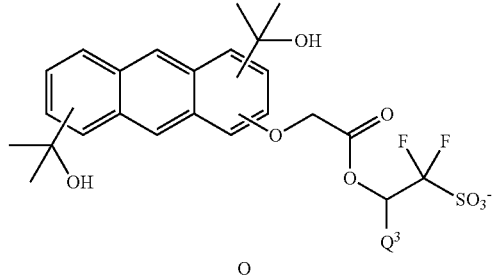
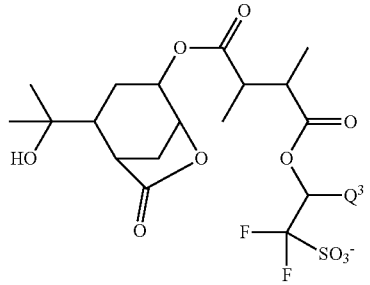
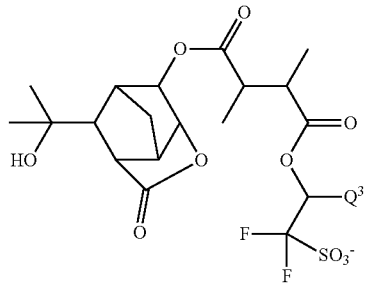

77
-continued
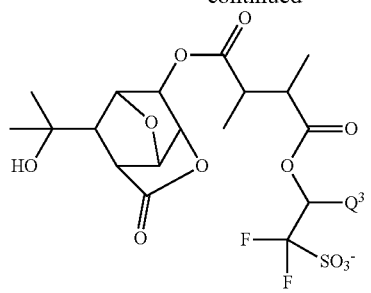
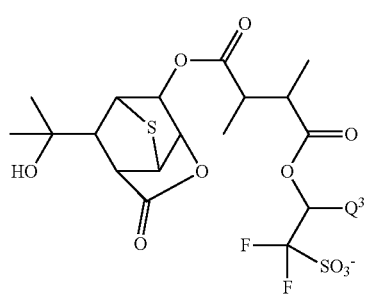
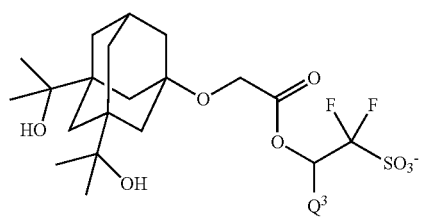
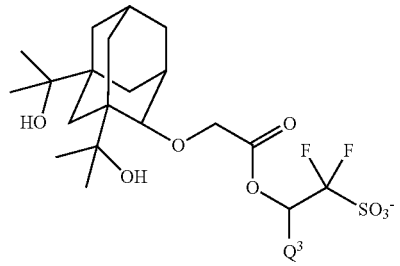
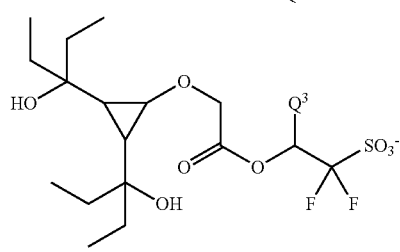
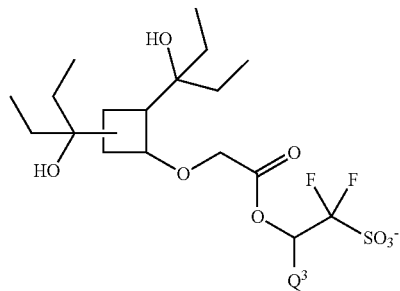
78
-continued
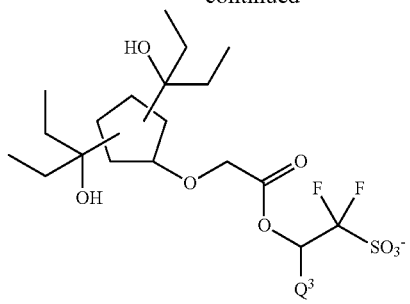
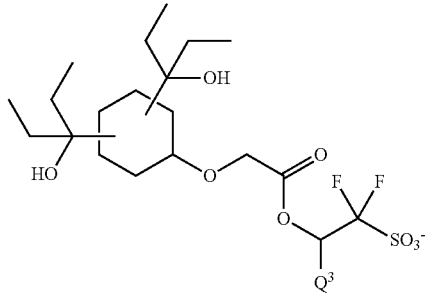
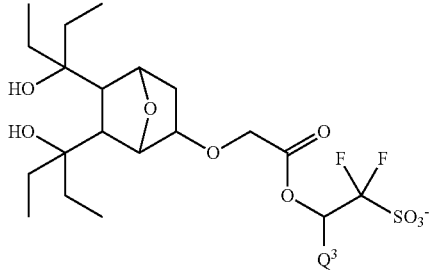
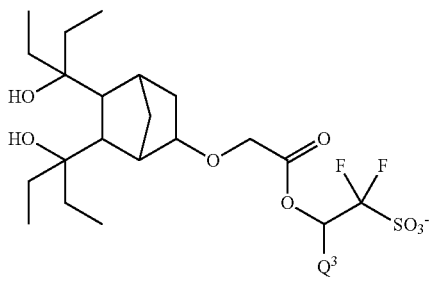
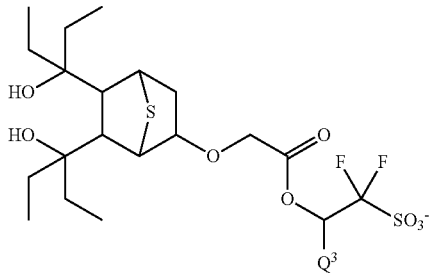
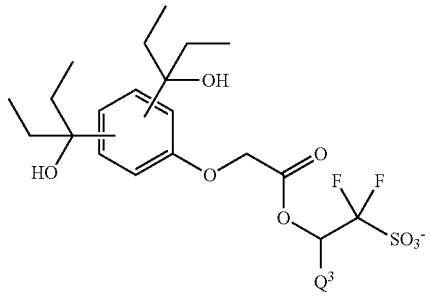

79
-continued
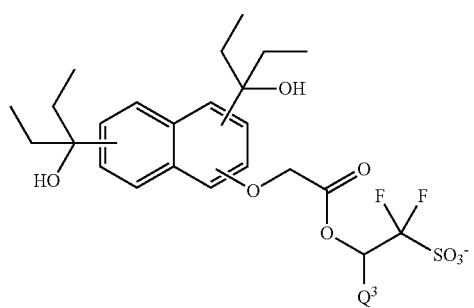
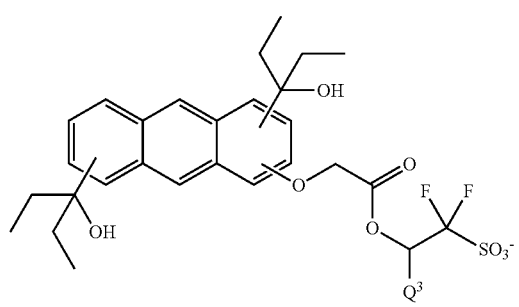
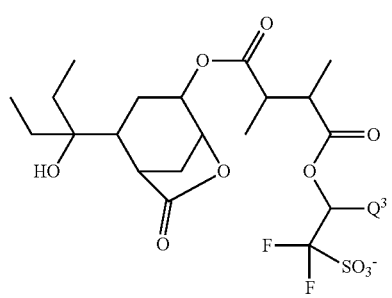
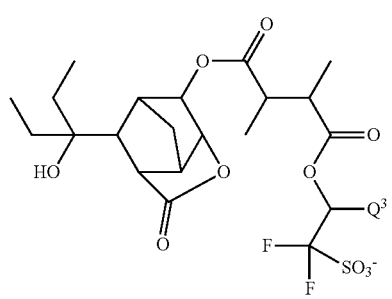
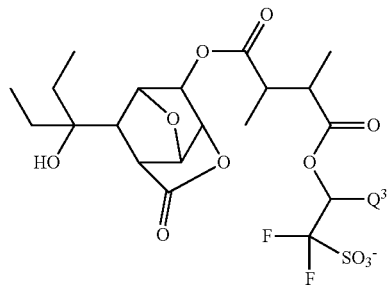
80
-continued
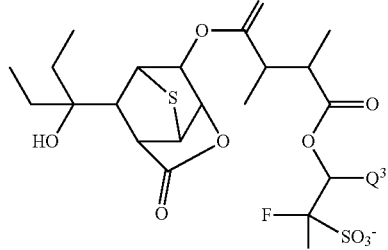
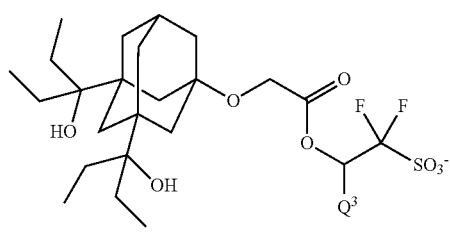
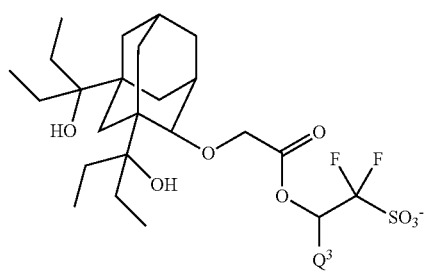
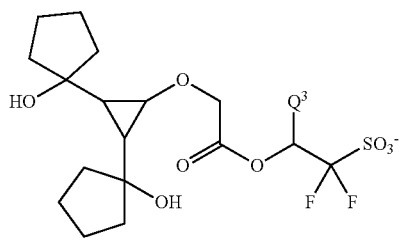
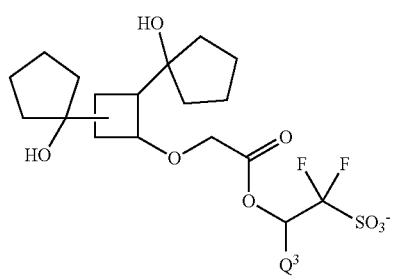
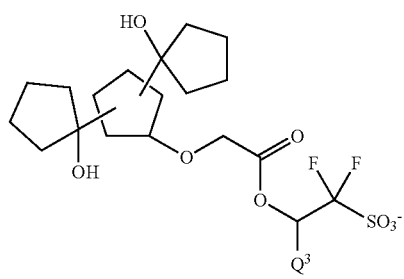

-continued
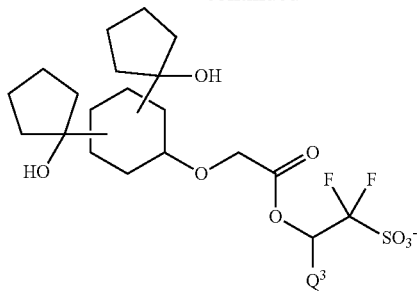
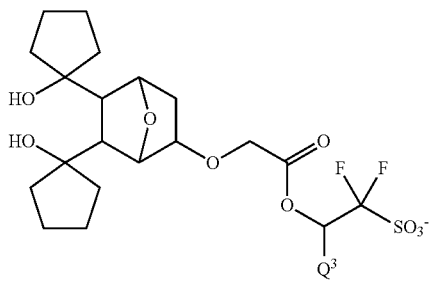
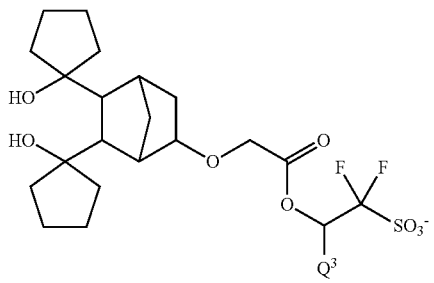
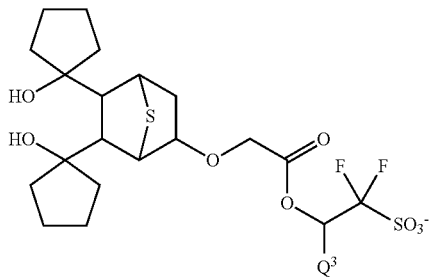
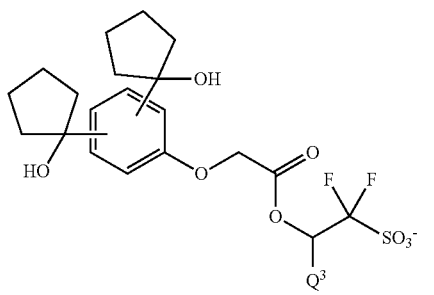
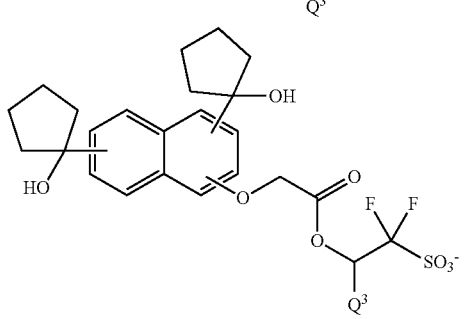
-continued
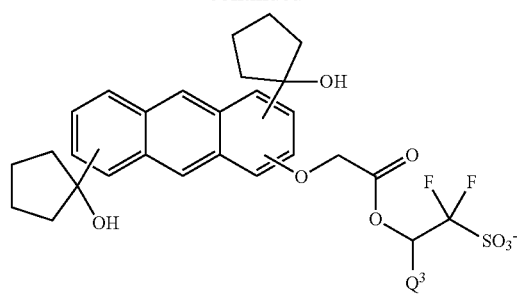
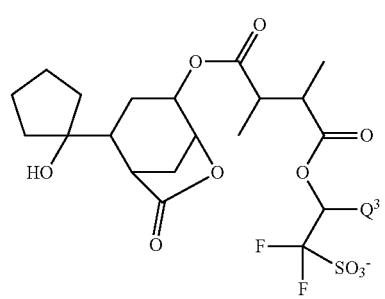
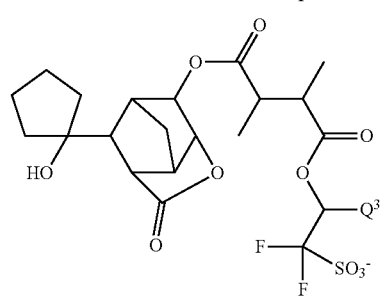
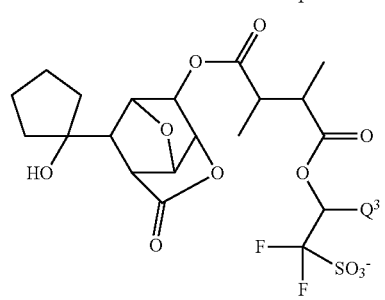
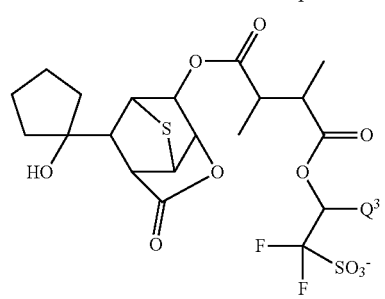
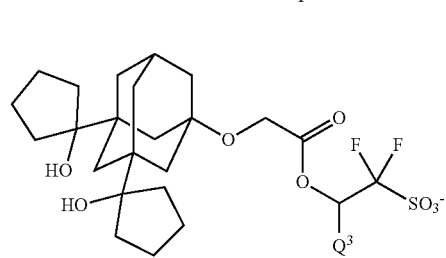

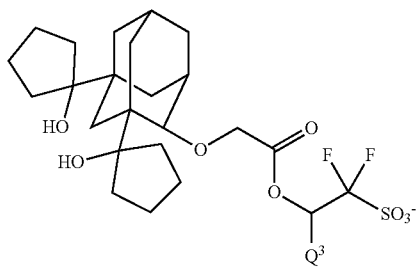

The cation of formula (A1-a) is a sulfonium cation. In formula (A1-a), $R^1$ is a $C_1$-$C_{20}$ hydrocarbyl group which may contain a heteroatom. The hydrocarbyl group may be saturated or unsaturated and straight, branched or cyclic. Examples thereof include alkyl groups such as methyl, ethyl, n-propyl, isopropyl, n-butyl, tert-butyl; cyclic saturated hydrocarbyl groups such as cyclopropyl, cyclopentyl, cyclohexyl, cyclopropylmethyl, 4-methylcyclohexyl, cyclohexylmethyl, norbornyl and adamantyl; alkenyl groups such as vinyl, allyl, propenyl, butenyl and hexenyl; cyclic unsaturated aliphatic hydrocarbyl groups such as cyclohexenyl; aryl groups such as phenyl and naphthyl; heteroaryl groups such as thienyl; and aralkyl groups such as benzyl, 1-phenylethyl and 2-phenylethyl. Of these, aryl groups are preferred. In the foregoing hydrocarbyl groups, some or all of the hydrogen atom may be substituted by a moiety containing a heteroatom such as oxygen. sulfur, nitrogen or halogen, or a moiety containing a heteroatom such as oxygen, sulfur or nitrogen may intervene in a carbon-carbon bond, so that the group may contain a hydroxyl moiety, cyano moiety, carbonyl moiety, ether bond, ester bond, sulfonic acid ester bond, carbonate bond, lactone ring, sultone ring, carboxylic anhydride or haloalkyl moiety.

Any two of two $R^1$ and $W^2$ may bond together to form a ring with the sulfur atom in the formula. Examples of the ring structure are shown below.

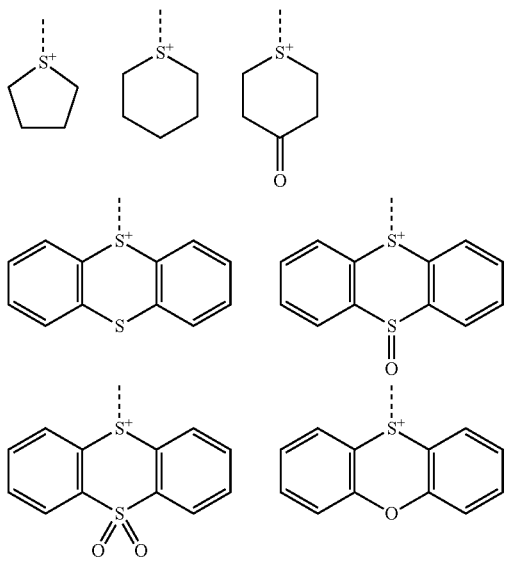

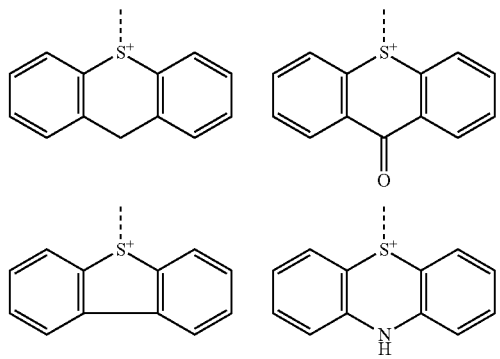

Examples of the sulfonium cation having formula (A1-a) are shown below, but not limited thereto.

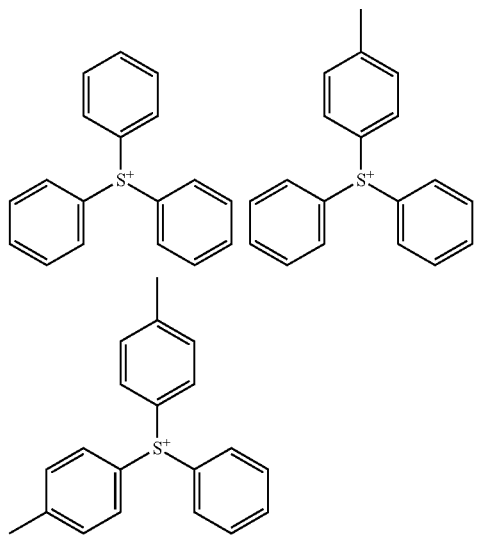

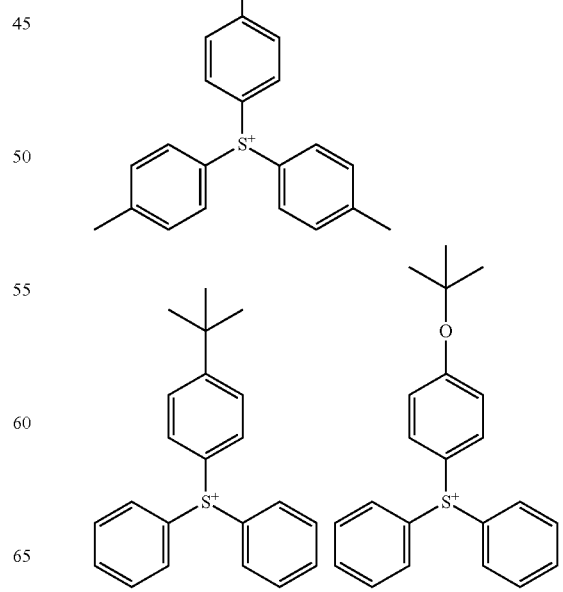

-continued
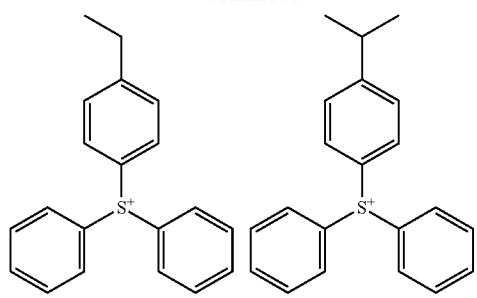
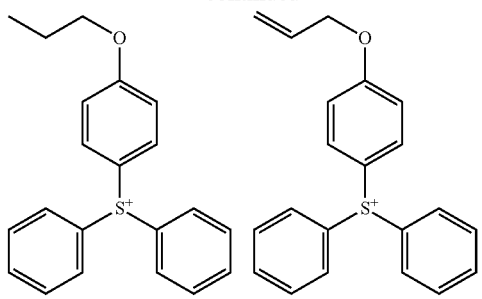
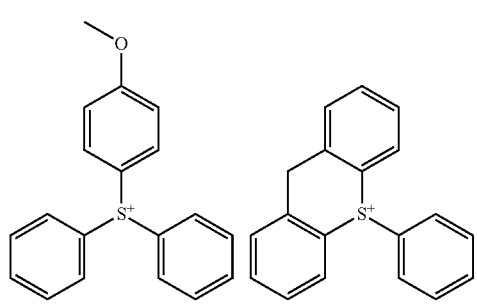
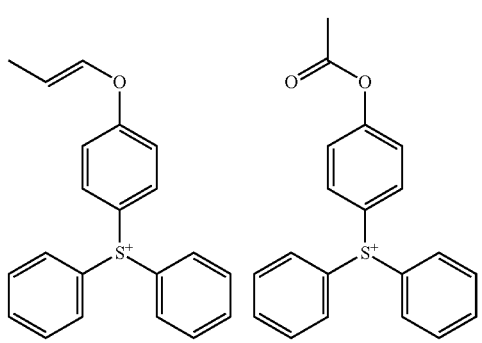
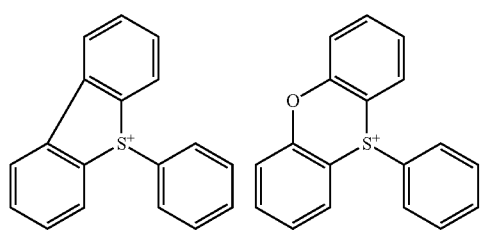
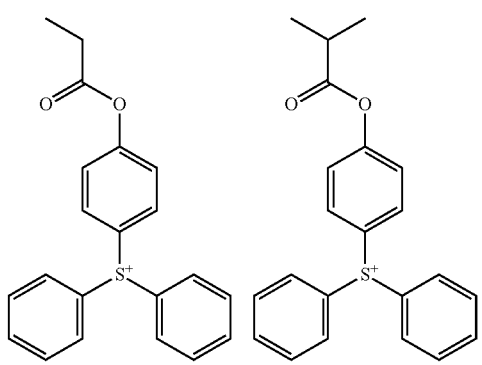
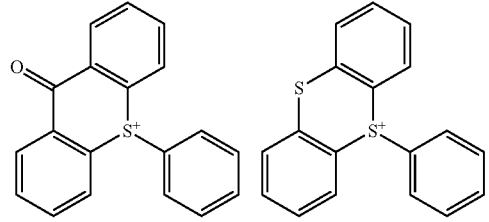
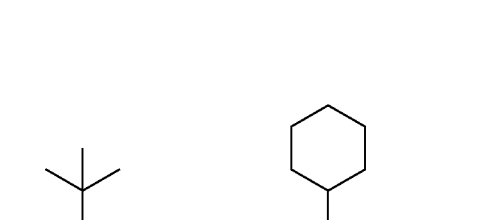
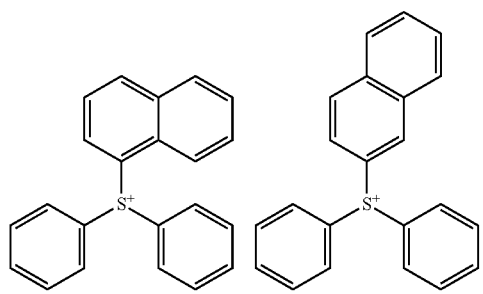
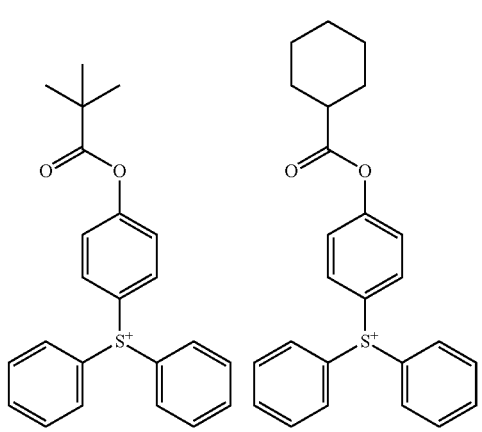
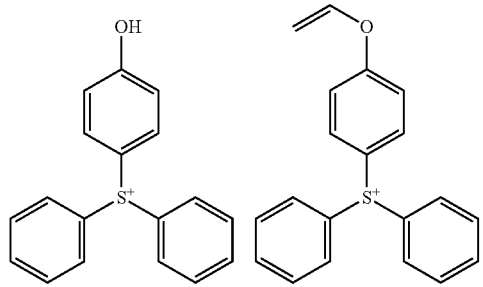

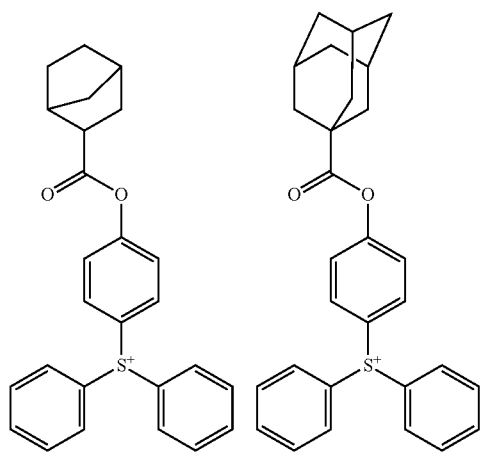
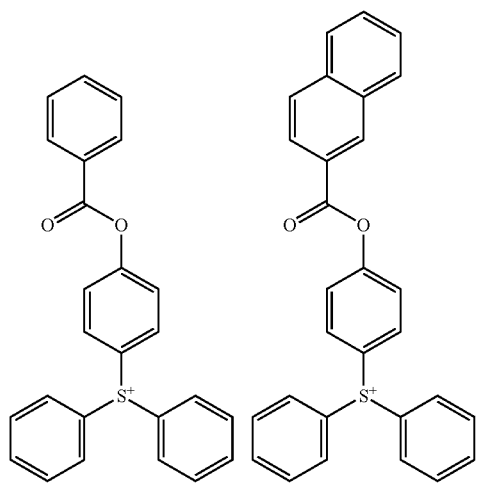
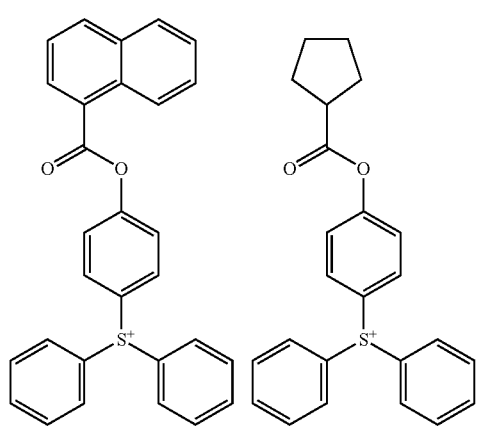
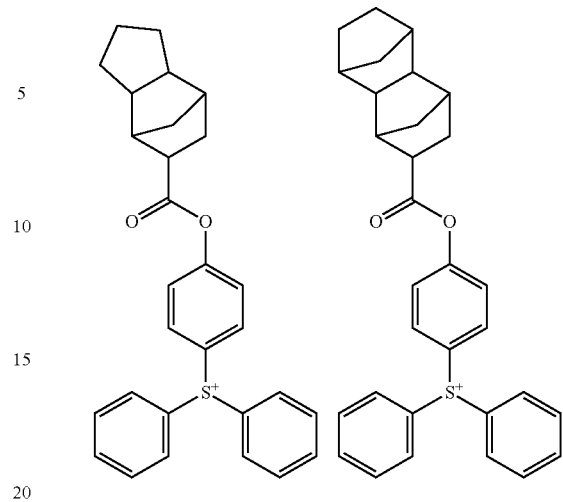
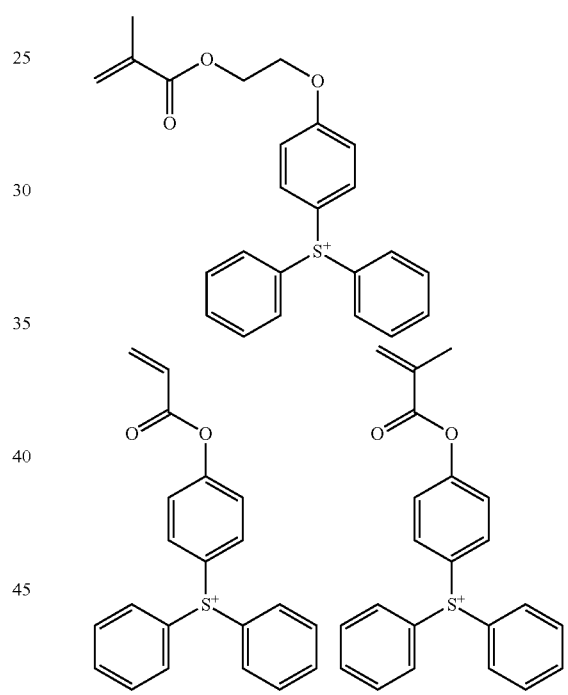
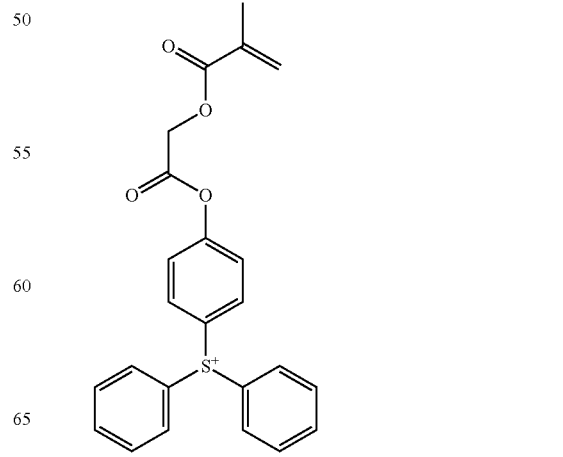

89
-continued
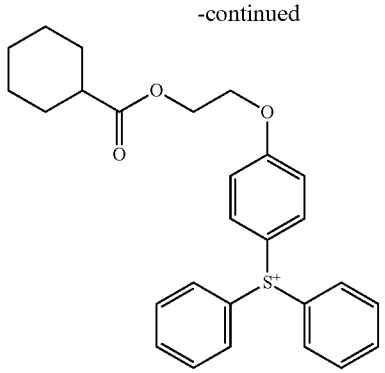
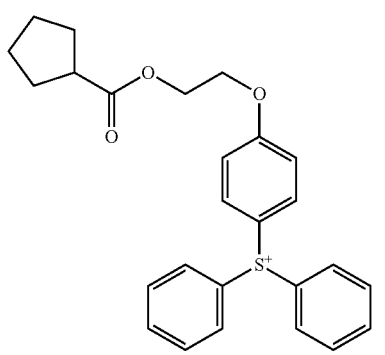
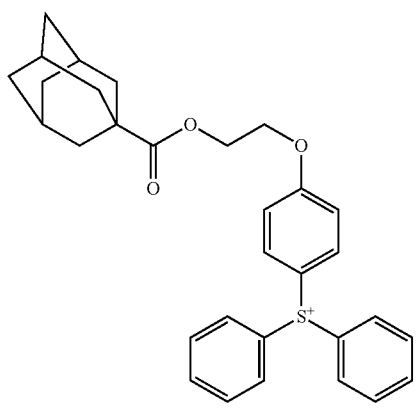
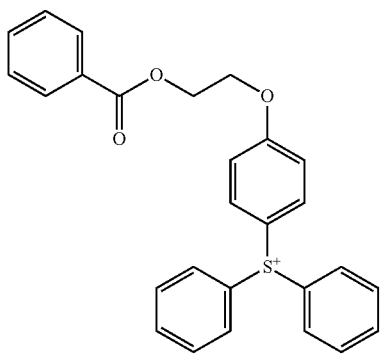
90
-continued
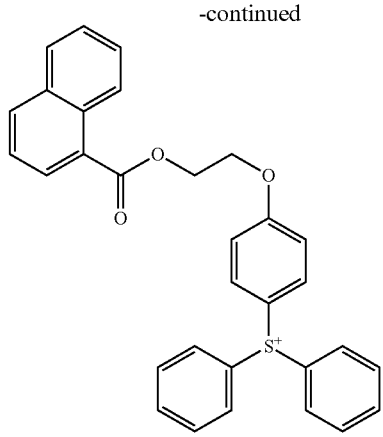
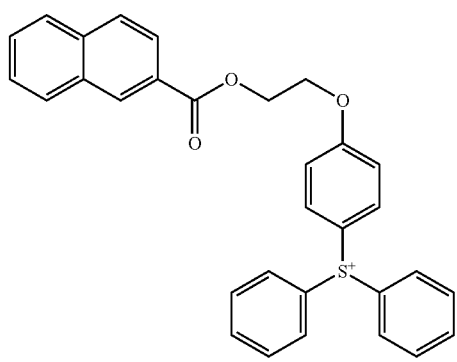
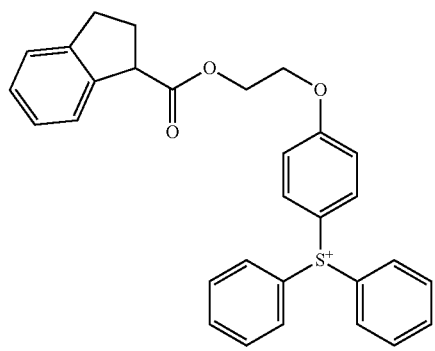
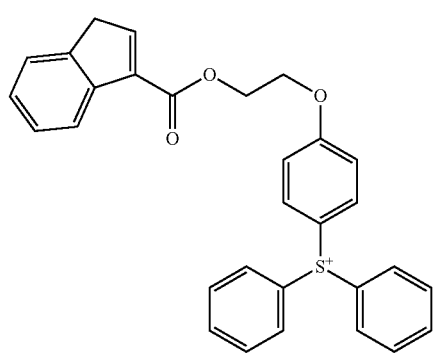

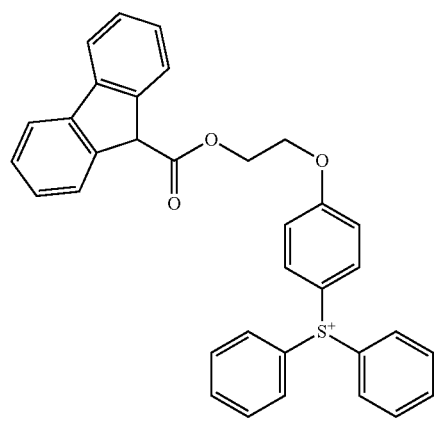
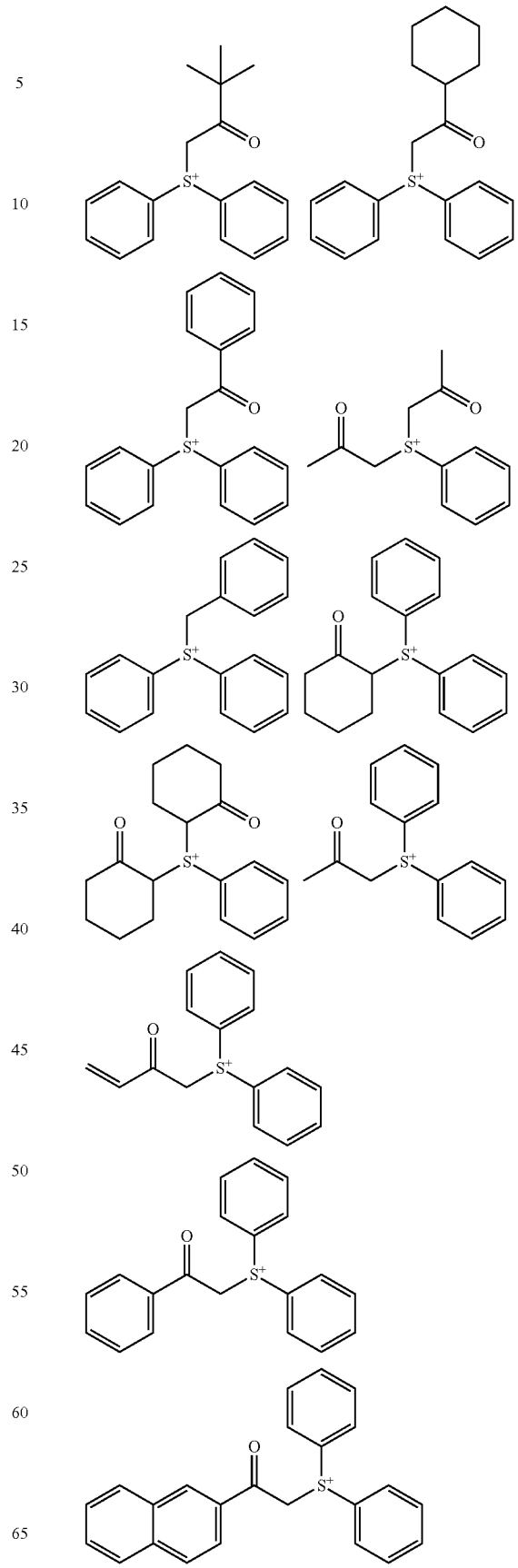

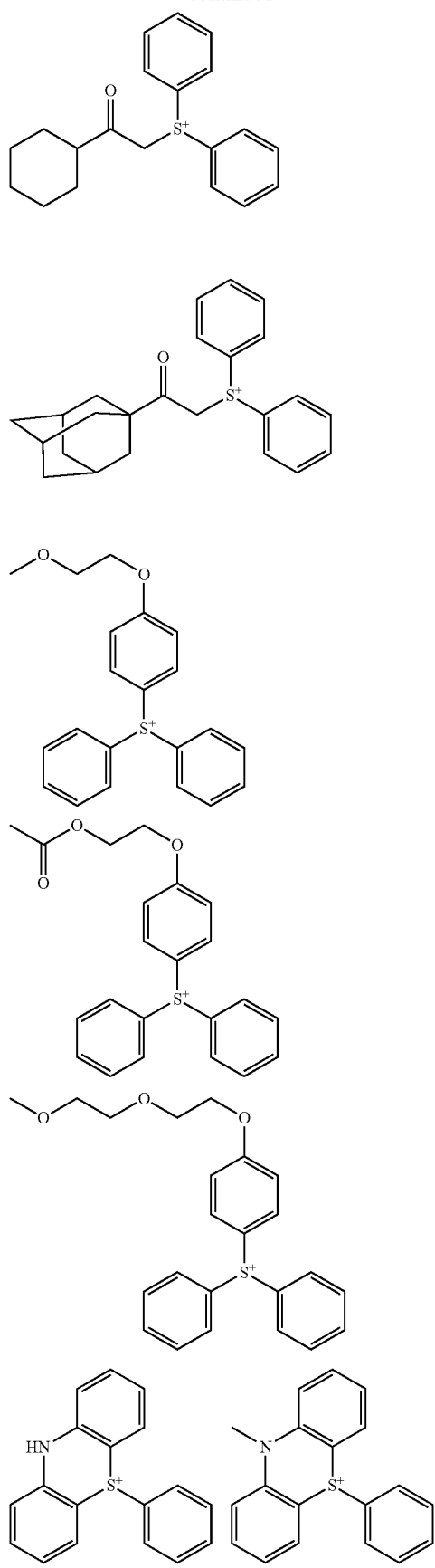

-continued
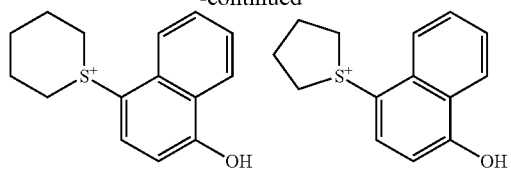
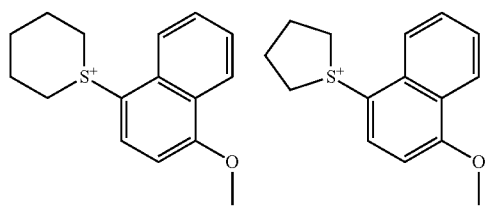
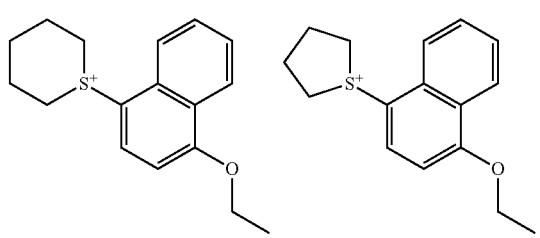
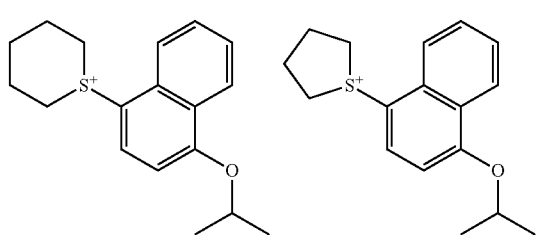
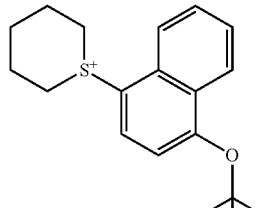
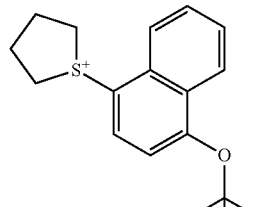
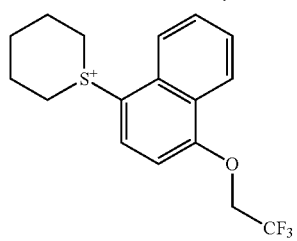
-continued
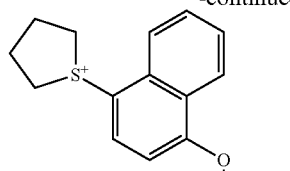
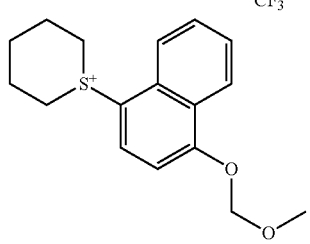
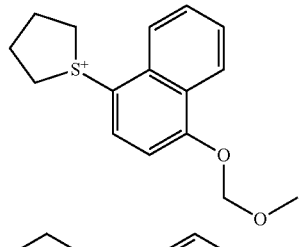
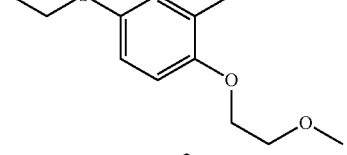
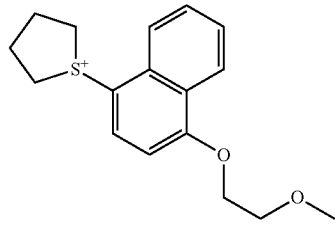
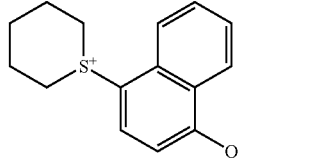
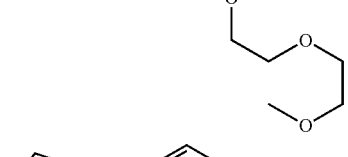
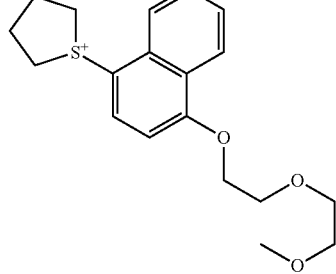

97
-continued
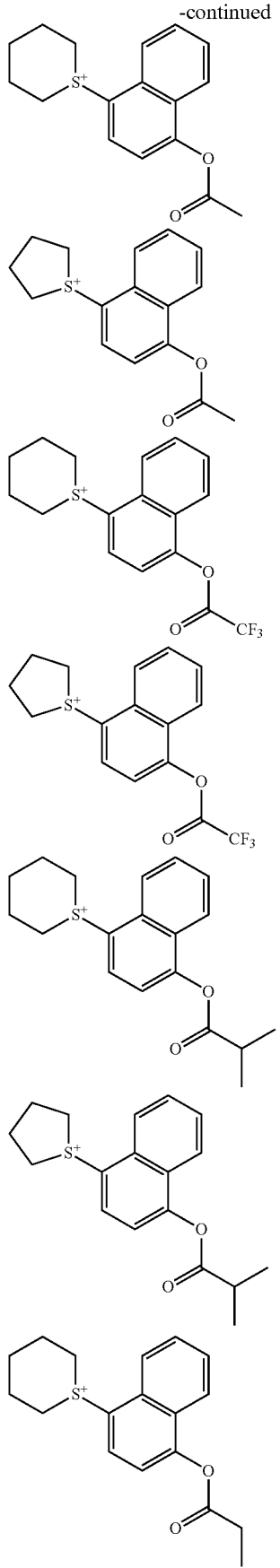
98
-continued
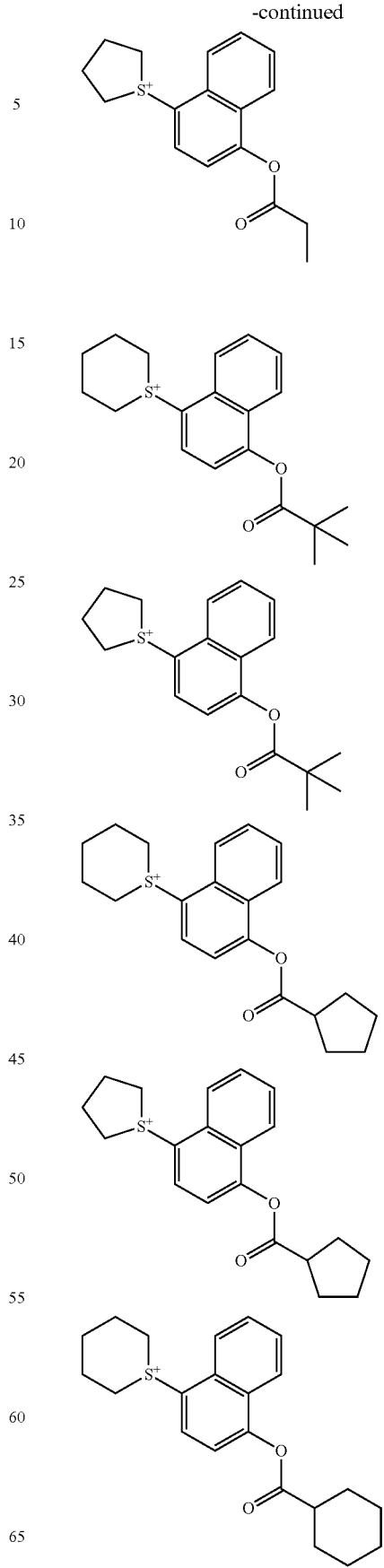

99
-continued
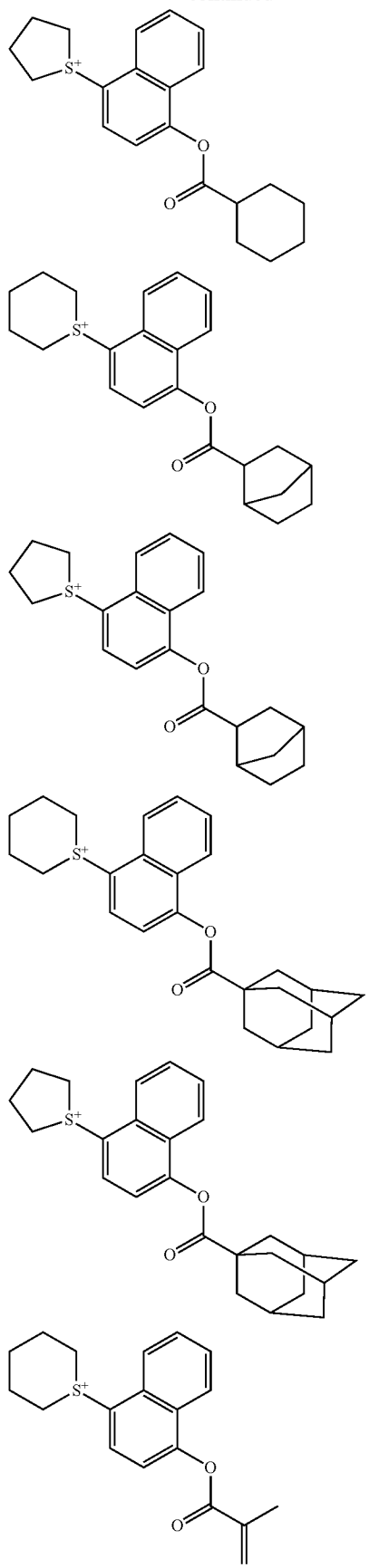
100
-continued
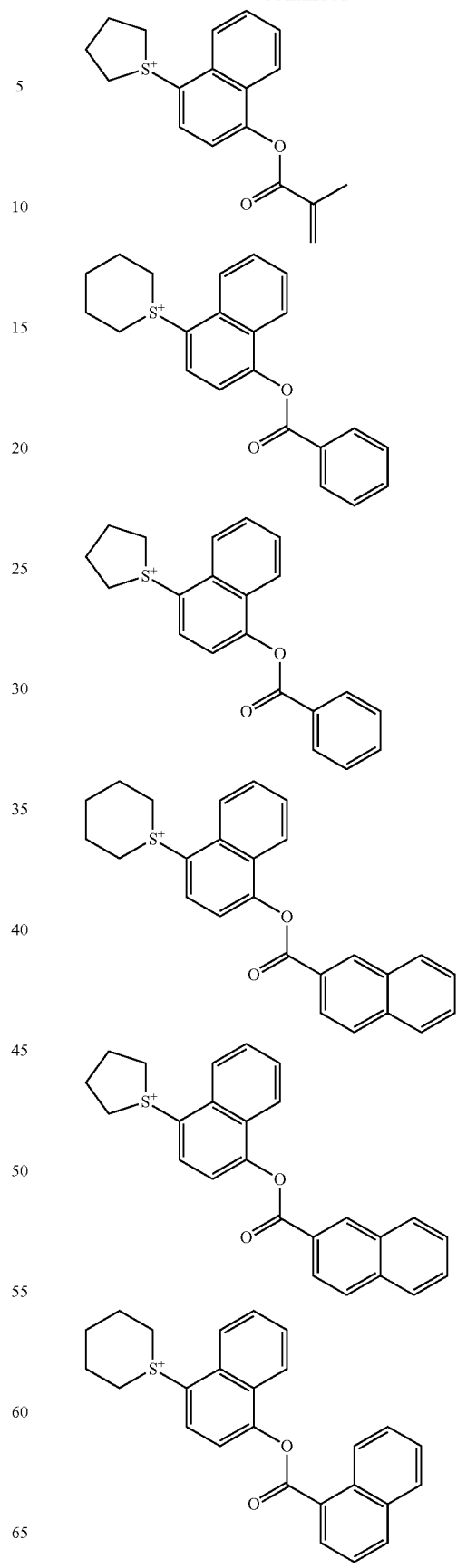

101
-continued
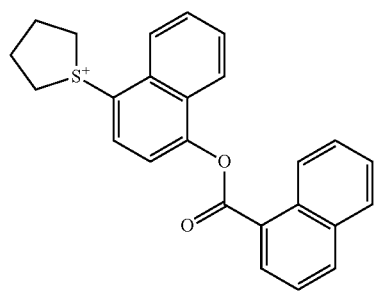
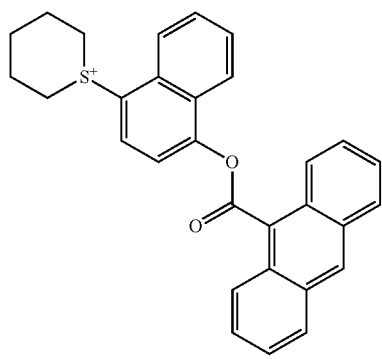
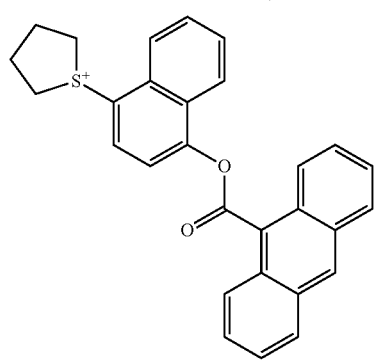
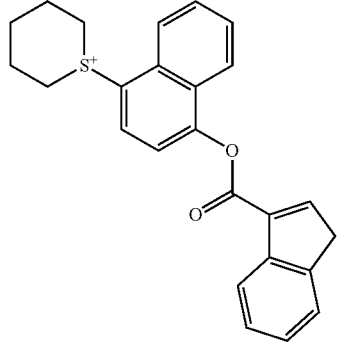
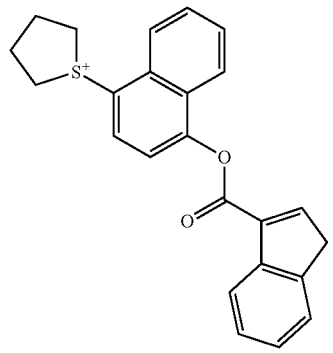
102
-continued
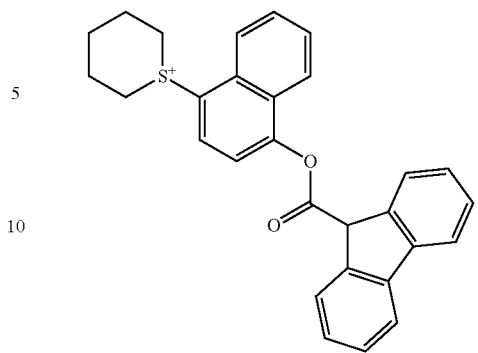
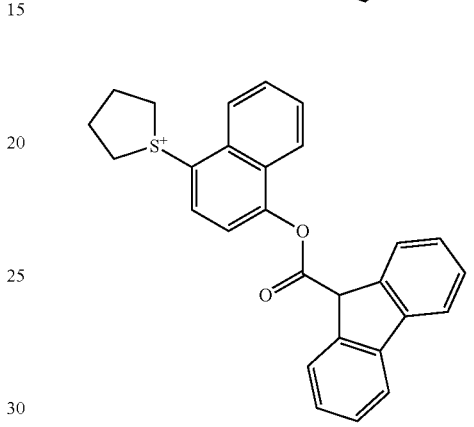
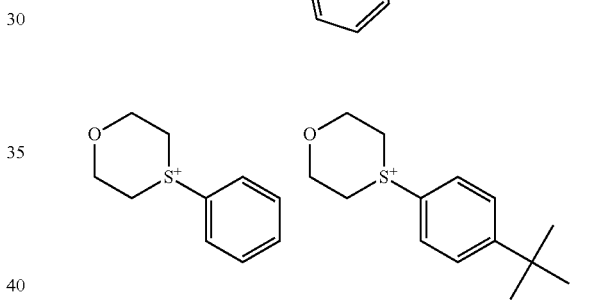
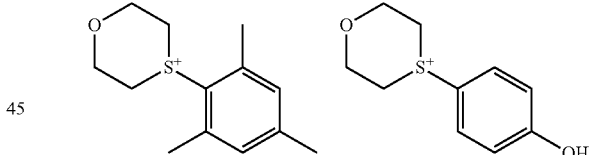
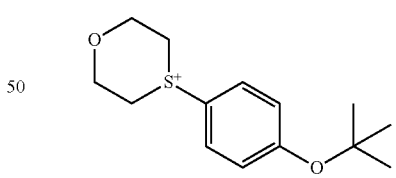
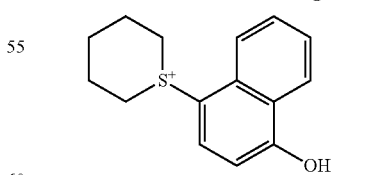
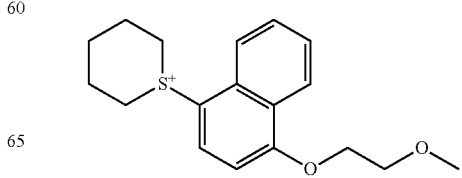

103
-continued
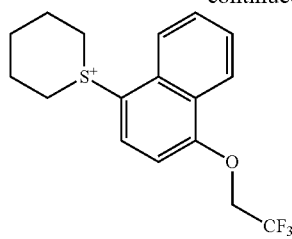
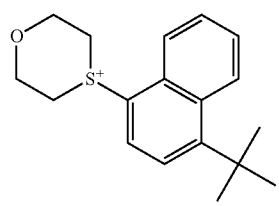
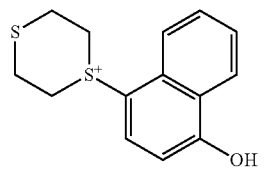
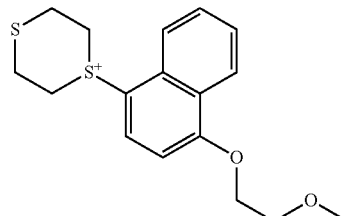
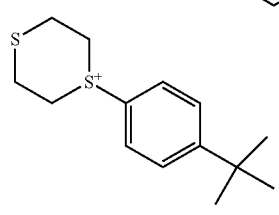
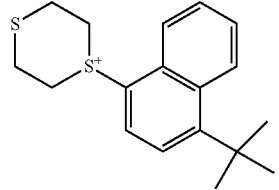
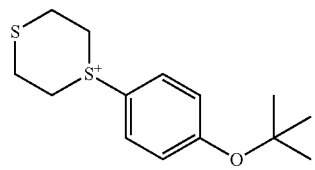
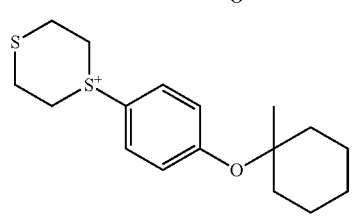
104
-continued
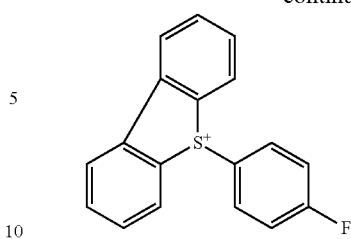
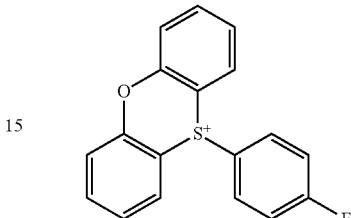
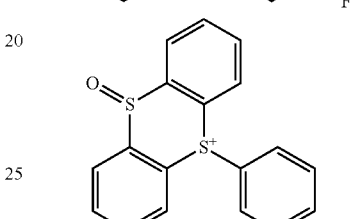
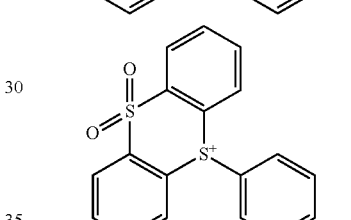
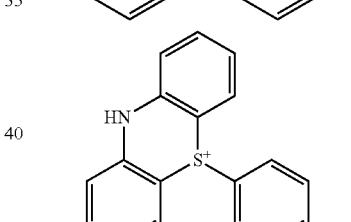
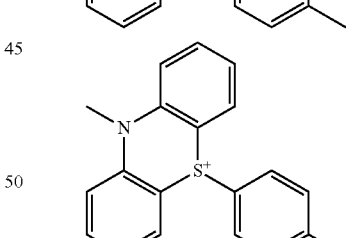
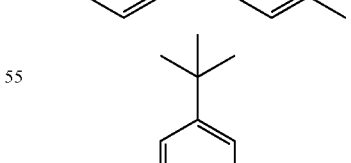
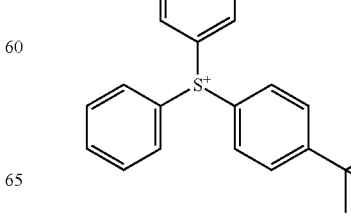

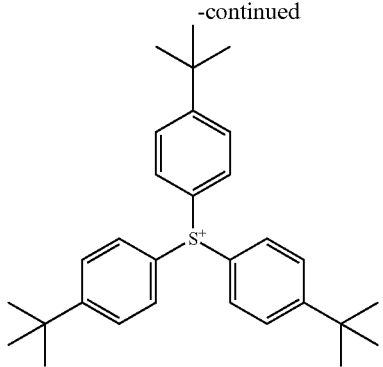
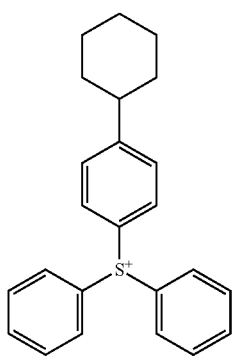
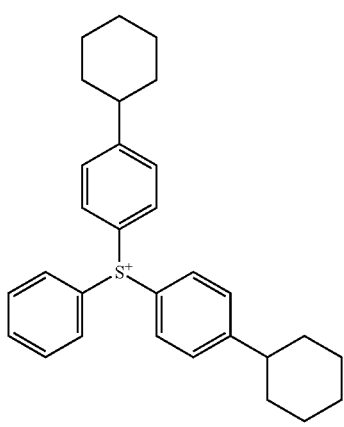
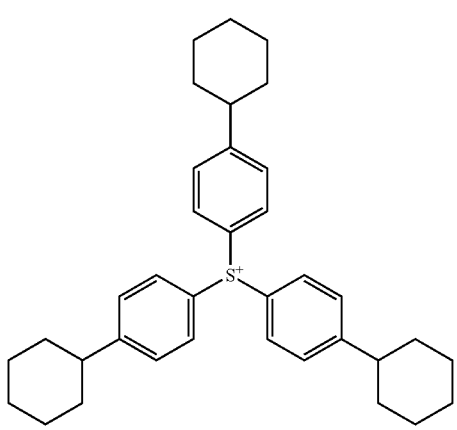
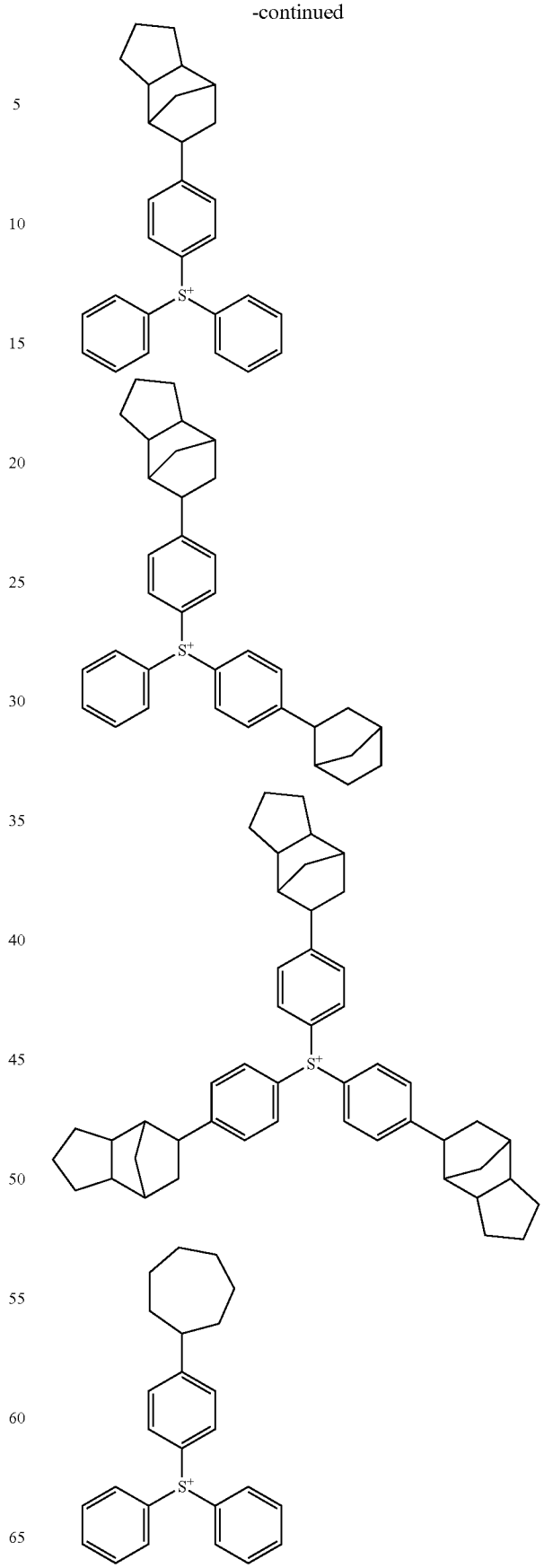

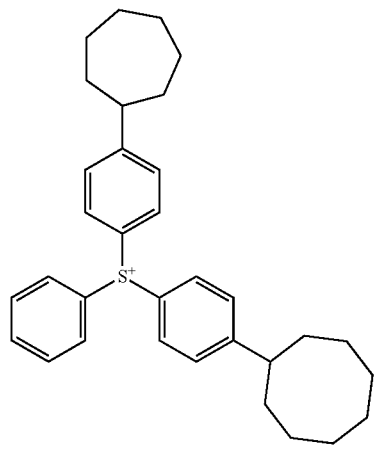
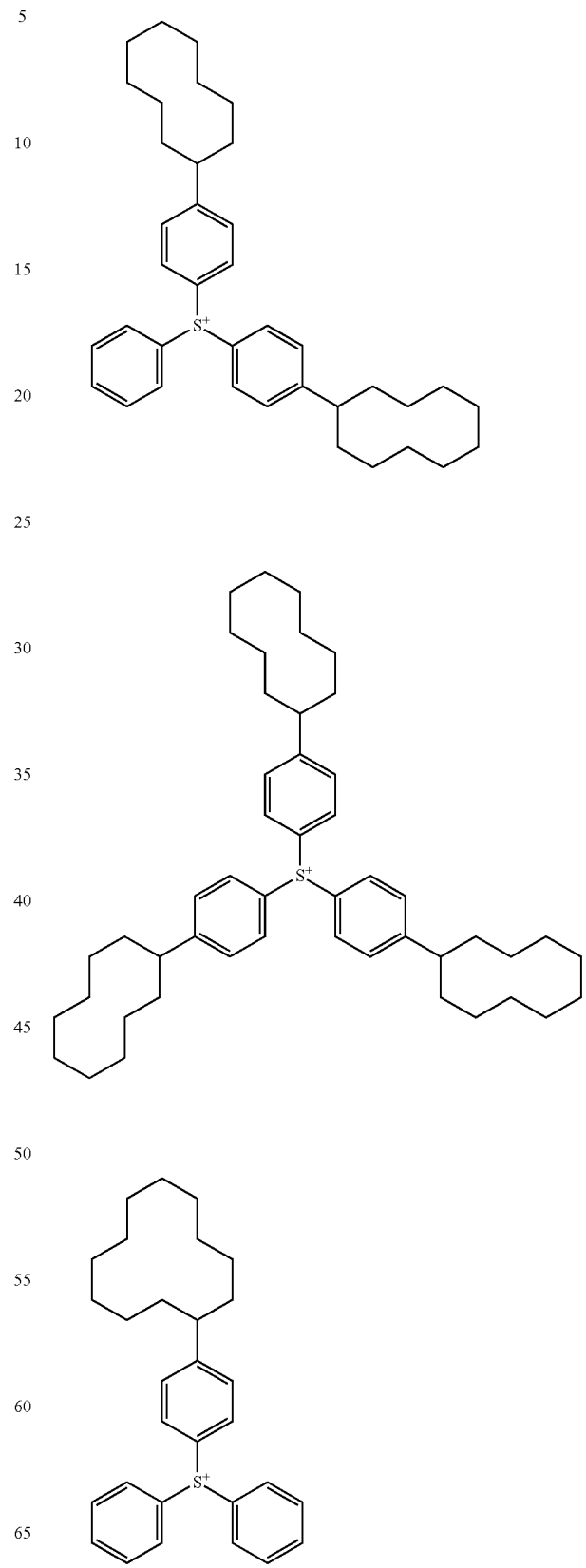

109
-continued
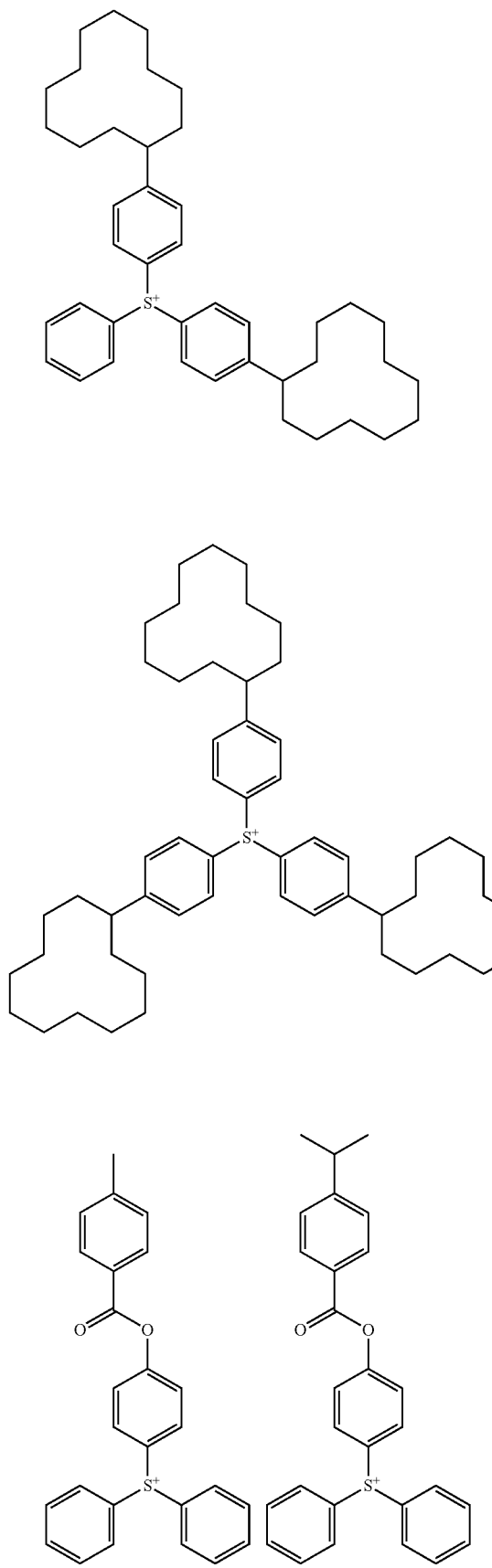
110
-continued
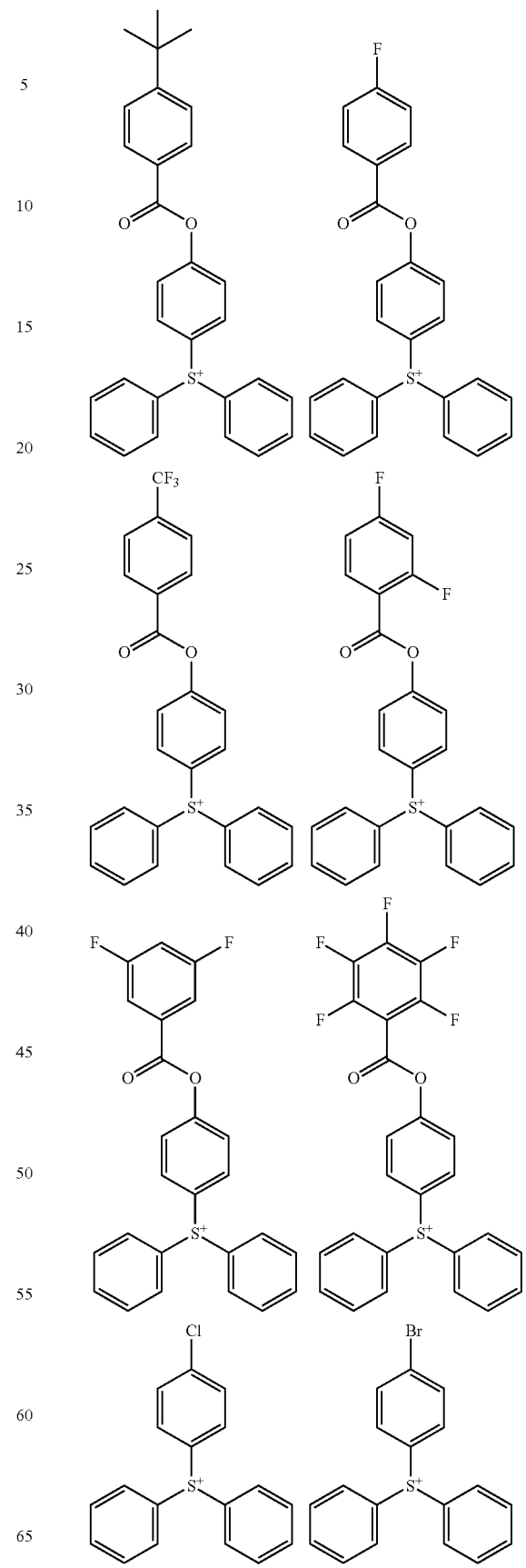

111
-continued
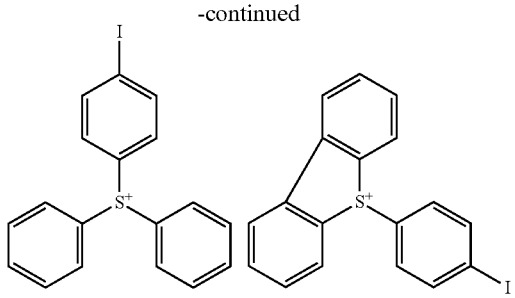
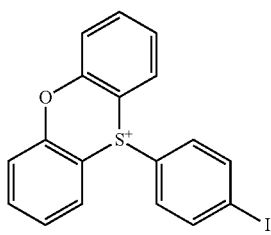
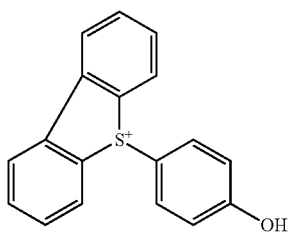
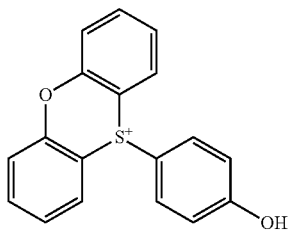
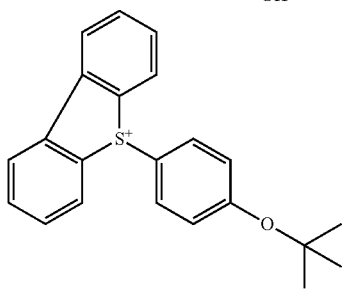
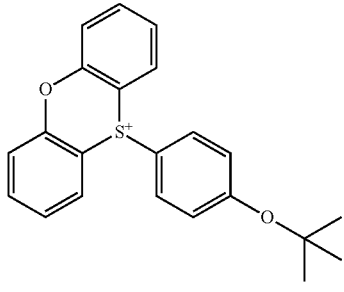
112
-continued
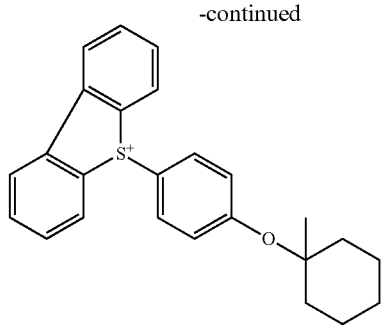

113
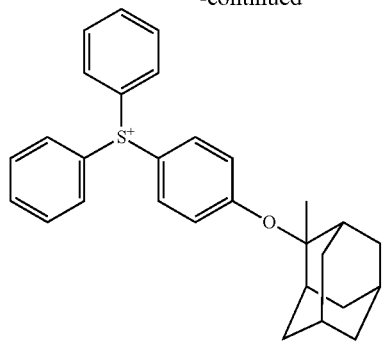
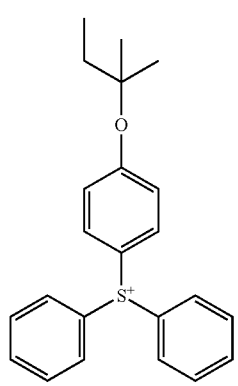
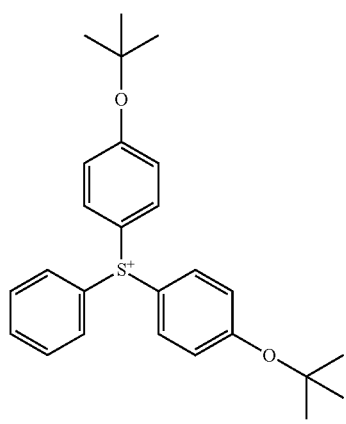
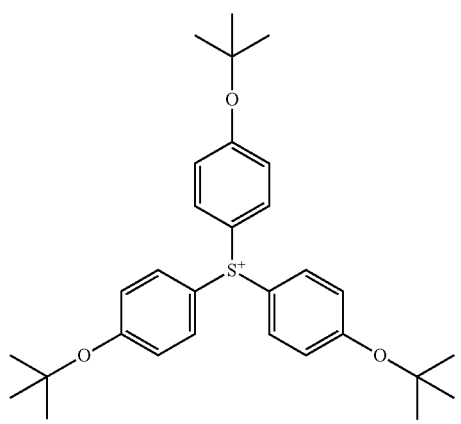
114
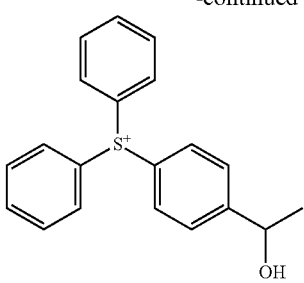
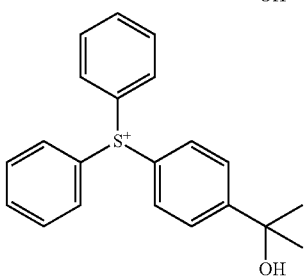
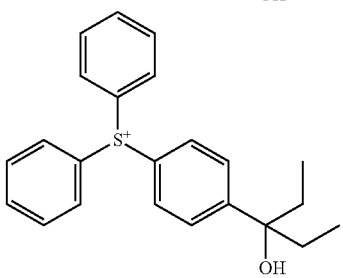
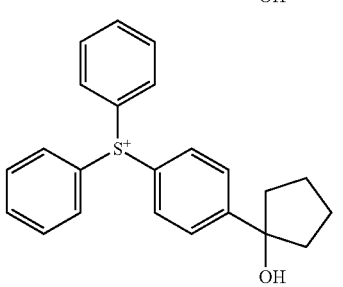
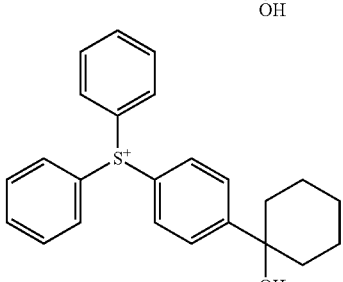
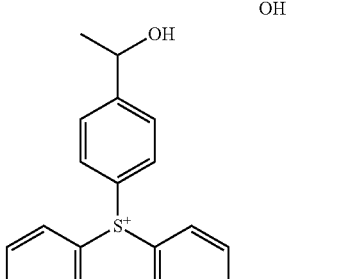

115
-continued
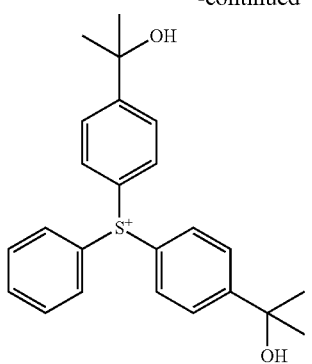
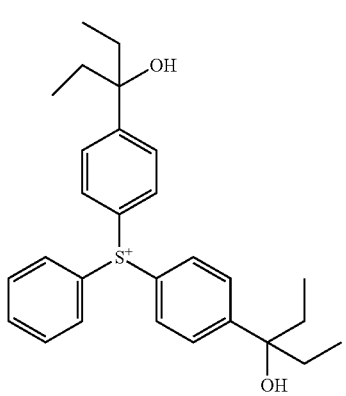
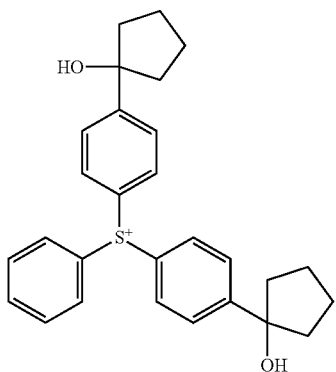
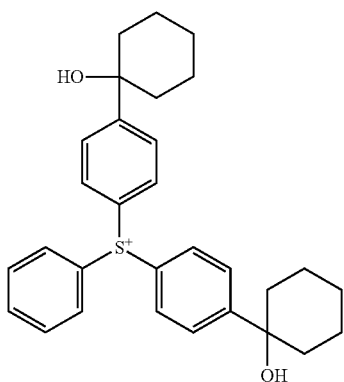
116
-continued
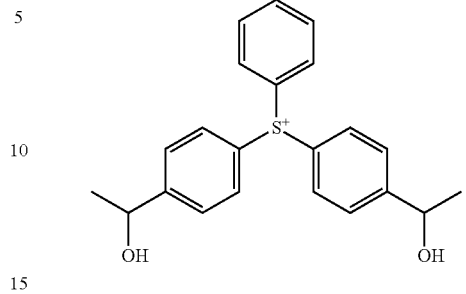
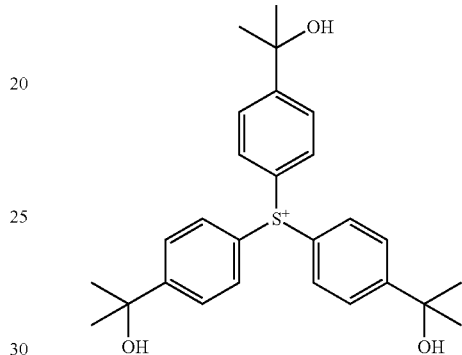
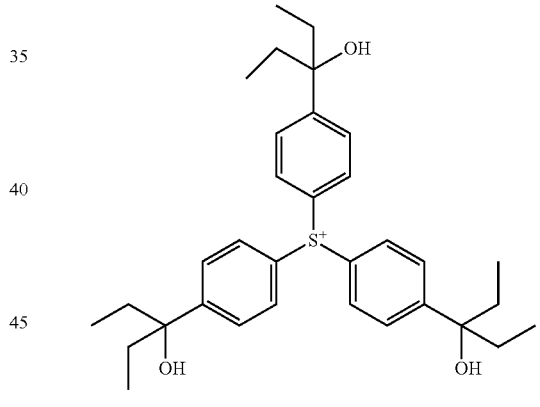
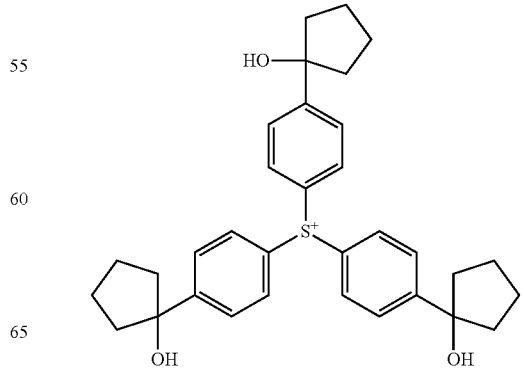

-continued
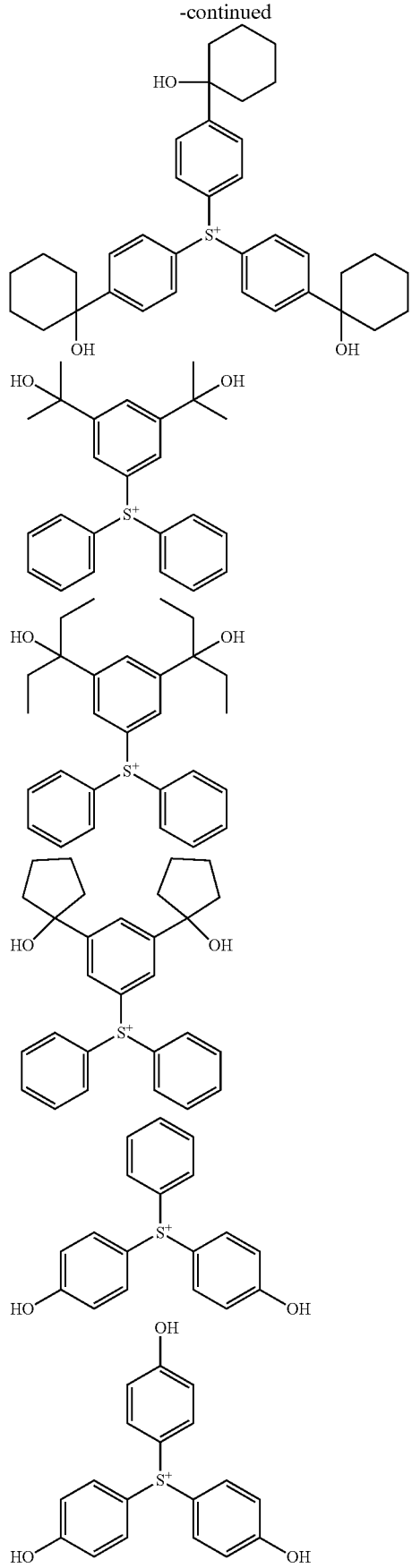
-continued
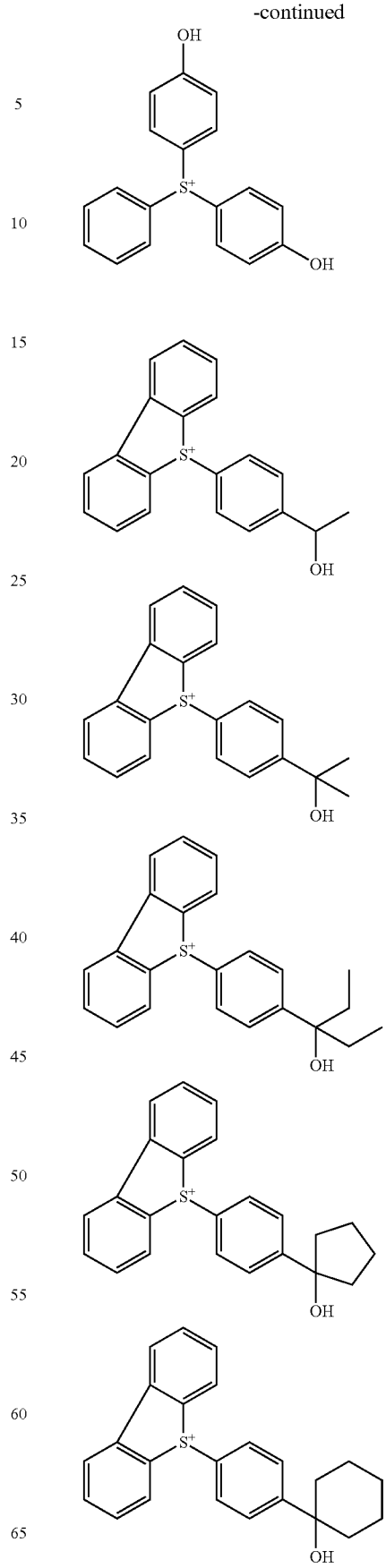

119
-continued
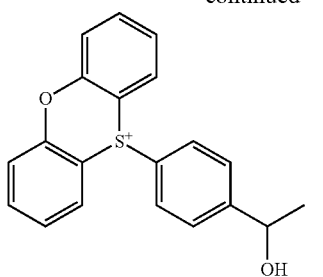
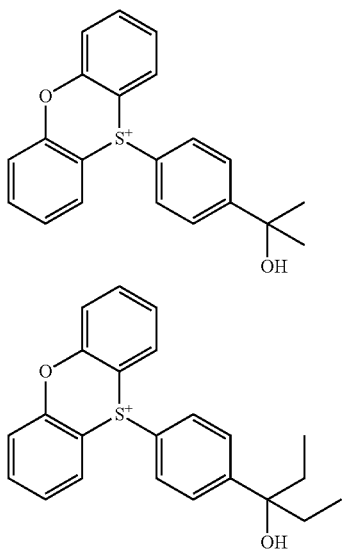
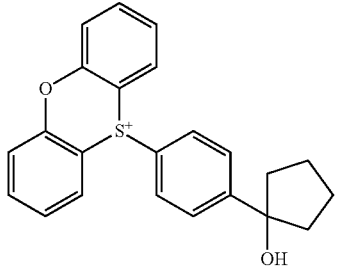
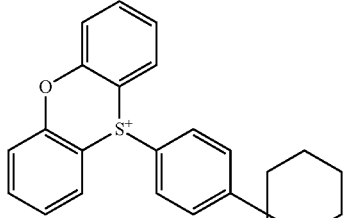
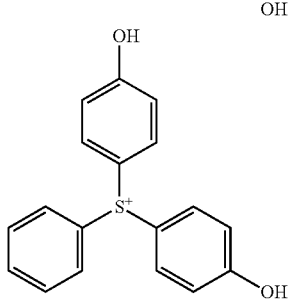
120
-continued
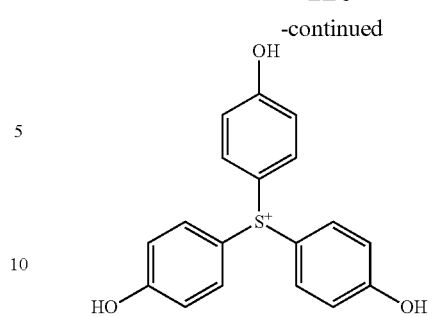
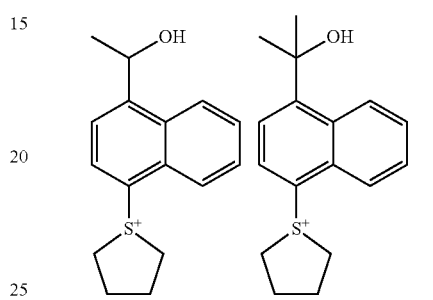
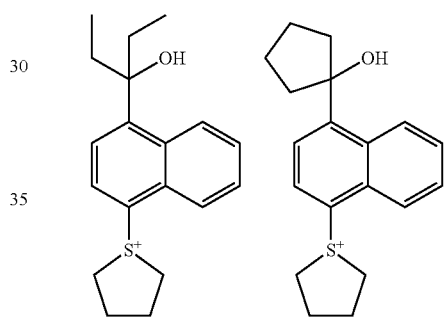
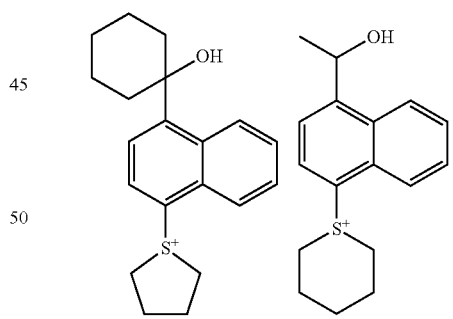
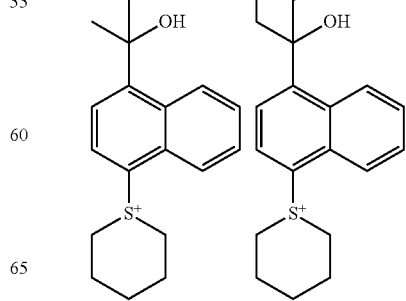

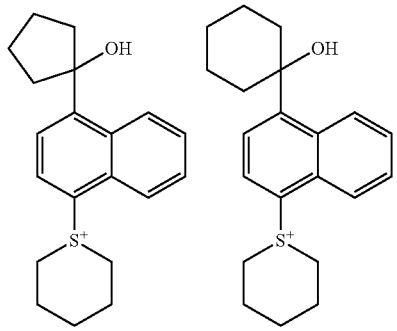

The cation of formula (A1-b) is an iodonium cation. In formula (A1-b), $R^2$ is a $C_1$-$C_{20}$ hydrocarbyl group which may contain a heteroatom. The hydrocarbyl group may be saturated or unsaturated and straight, branched or cyclic. Examples thereof are as exemplified above for $R^1$.

Examples of the iodonium cation having formula (A1-b) are shown below, but not limited thereto.

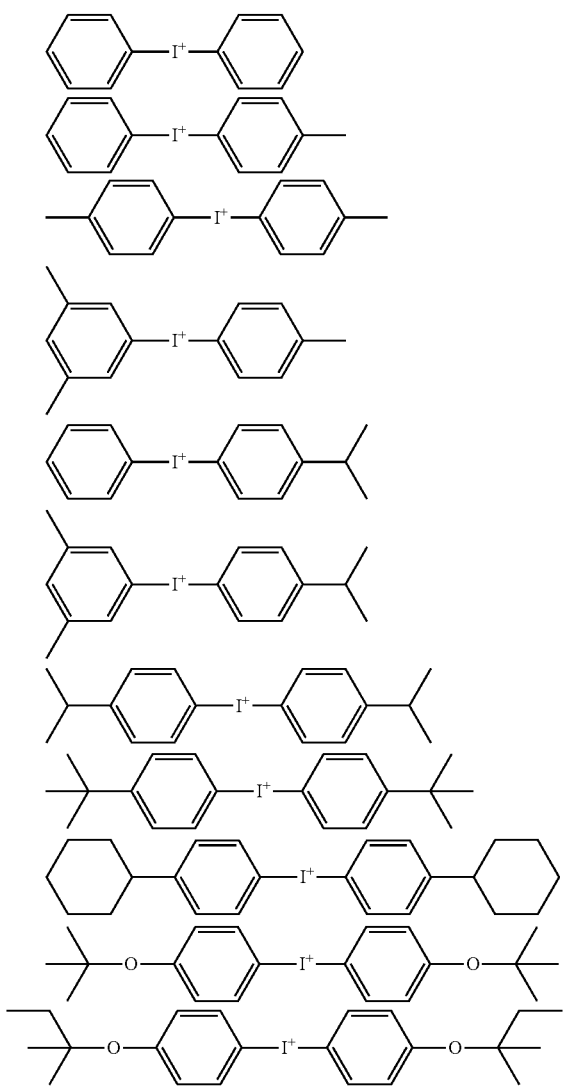

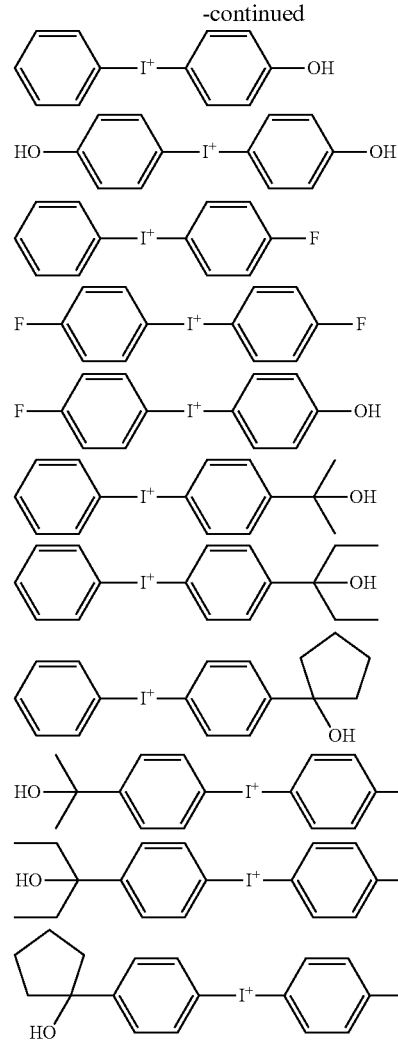

The cation of formula (A1-c) is an ammonium cation. In formula (A1-c), $R^3$ is a $C_1$-$C_{20}$ hydrocarbyl group which may contain a heteroatom. The hydrocarbyl group may be saturated or unsaturated and straight, branched or cyclic. Examples thereof are as exemplified above for $R^1$.

Examples of the ammonium cation having formula (A1-c) we shown below, but not limited thereto.

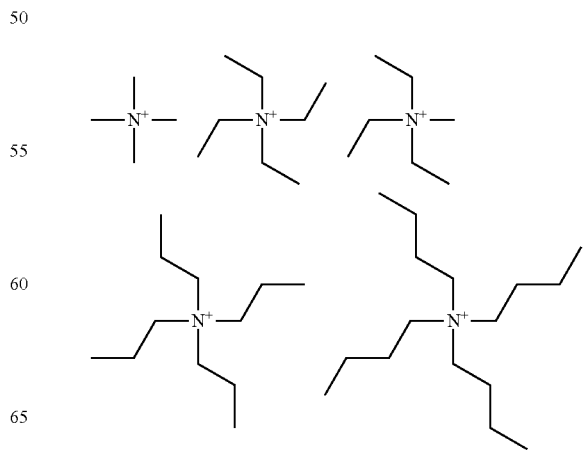

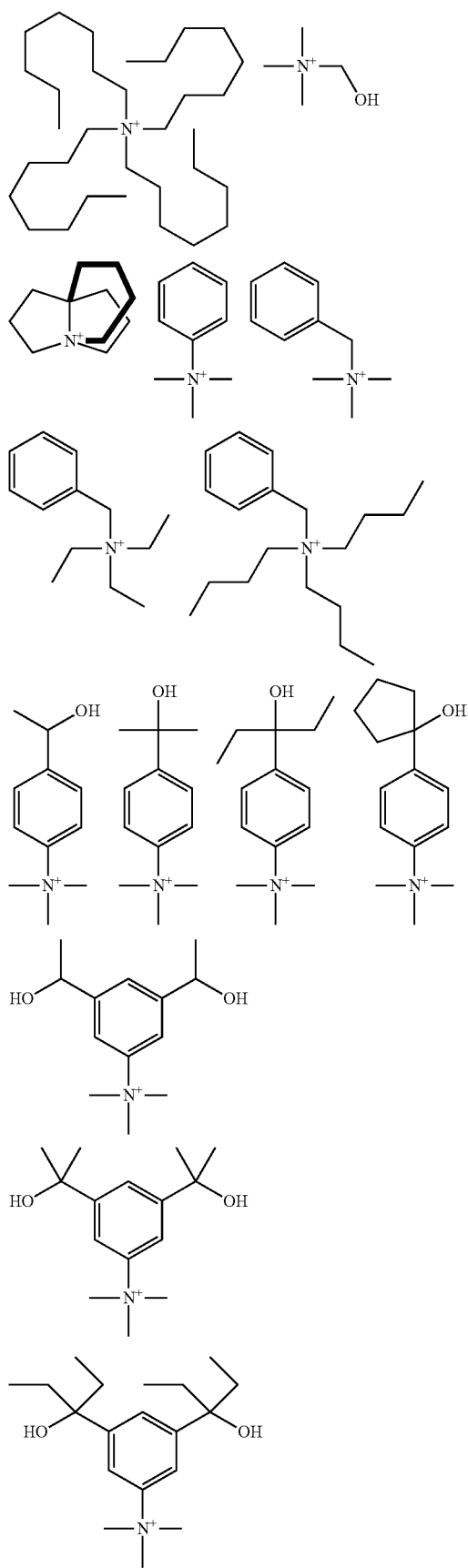
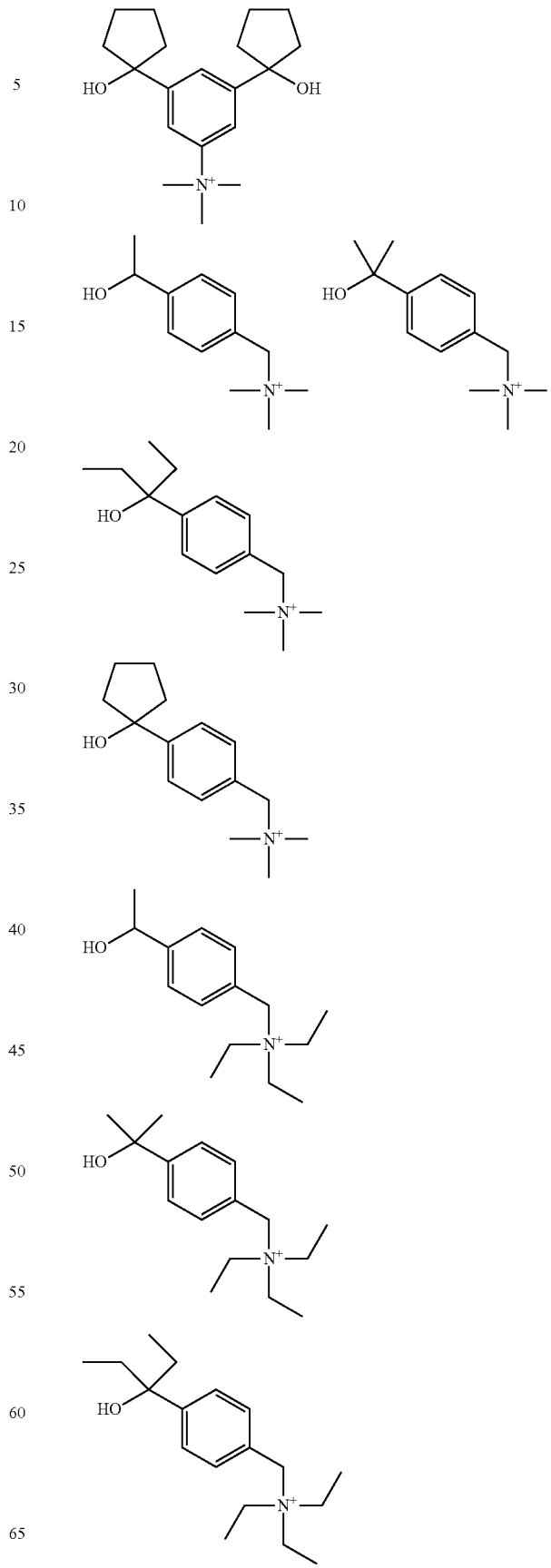

125
-continued
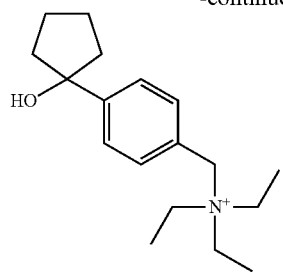
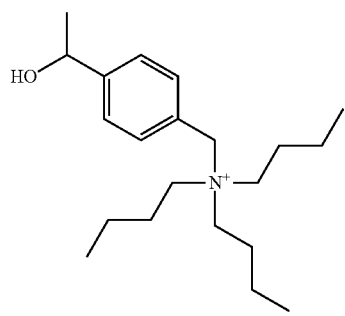
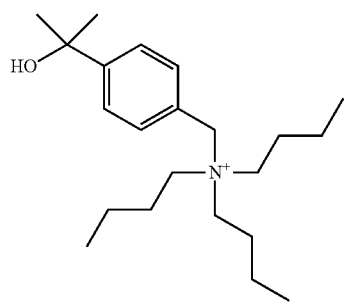
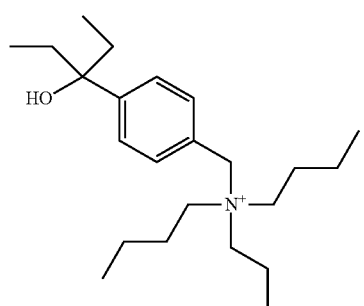
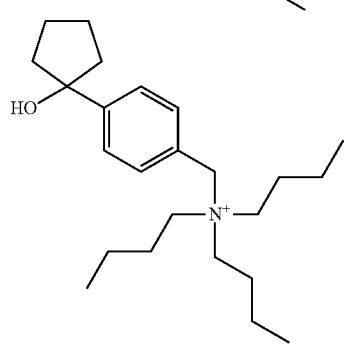
126
-continued
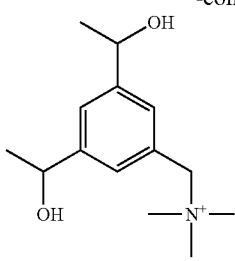
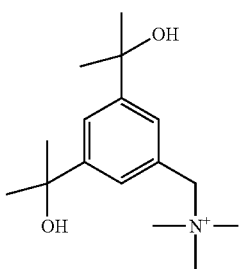
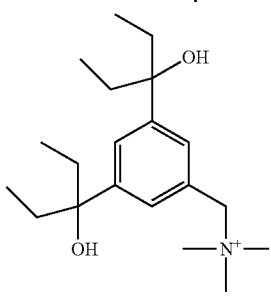
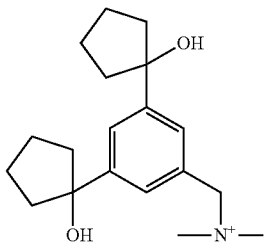
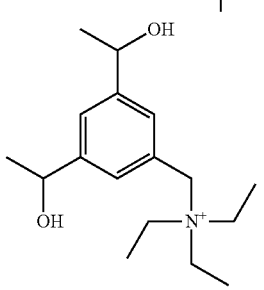
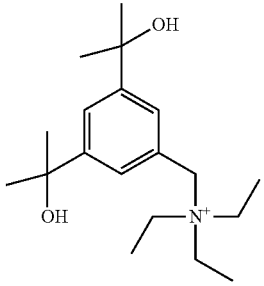

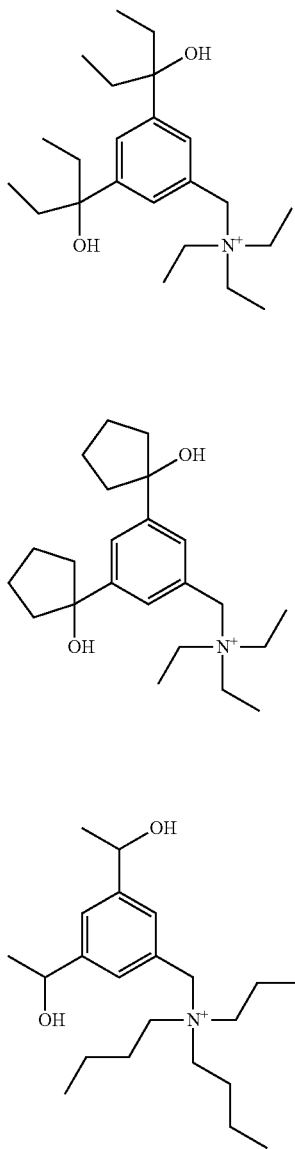
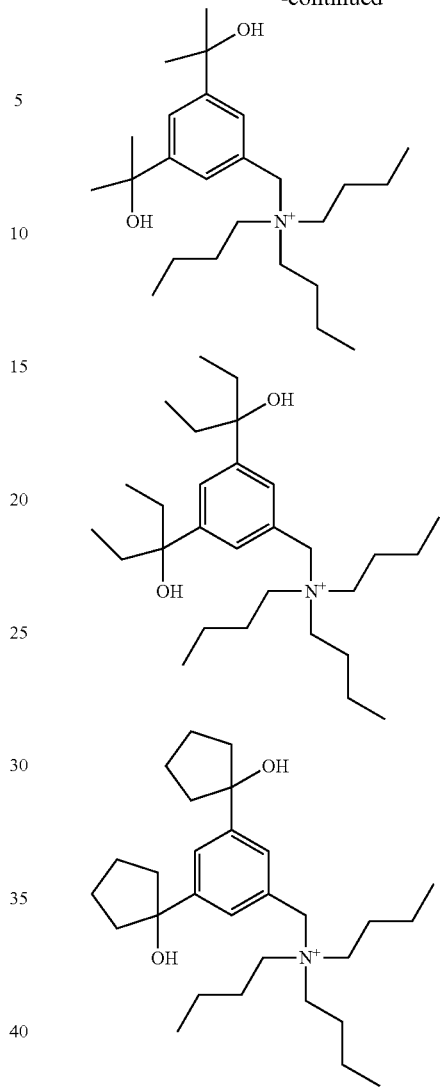
The onium salt of the invention may be prepared, for example, according to the following scheme. Although reference is made to the synthesis of an onium salt having the following formula (A1-1) as a typical example, the synthesis method is not limited thereto.
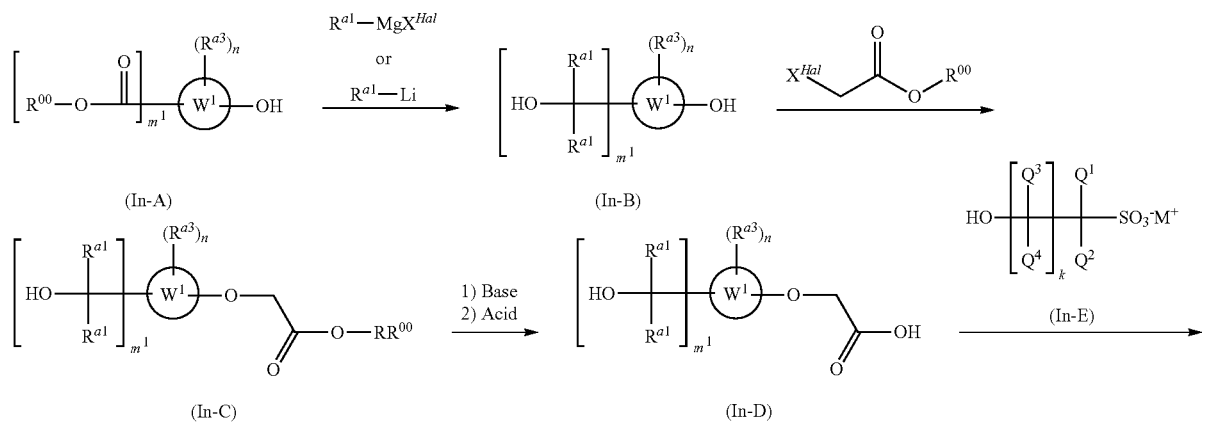

-continued

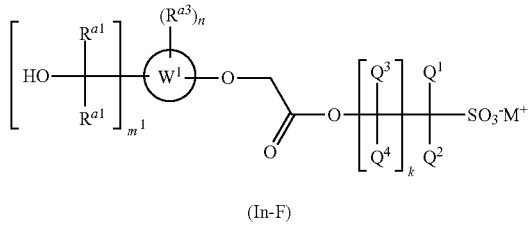

(In-F)

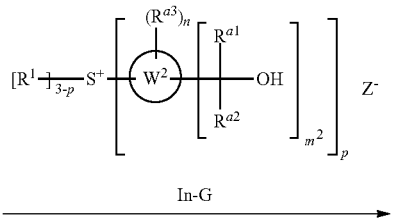

In-G

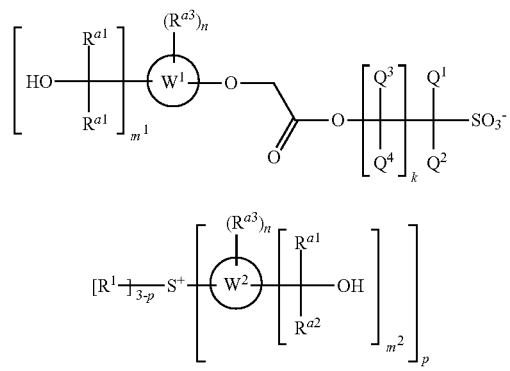

A1-1

Herein, $Q^1$ to $Q^1$, $W^1$, $W^2$, $R^{a1}$ to $R^{a3}$, $R^1$, k, $m^1$, $m^2$, n and p are as defined above. $R^{00}$ is a $C_1$-$C_3$ hydrocarbyl group, $X^{Ha1}$ is a halogen atom other than fluorine, M is a counter cation, and $Z^-$ is a counter anion.

The first step is to react an Intermediate In-A, which is commercially available or may be synthesized by any well-known organic synthesis method, with a Grignard reagent or organolithium reagent to form an Intermediate In-B. The reaction may be conducted by any well-known organic synthesis method. Specifically, the Grignard reagent or organolithium reagent is diluted with a solvent such as tetrahydrofuran (THF) or diethyl ether, to which a solution of Intermediate In-A in a solvent such as THF or diethyl ether is added dropwise. The amount of the Grignard reagent or organolithium reagent used is preferably (2 $m^1$+2) equivalents, with the number of ester bonds in Intermediate In-A and the loss by deactivation with hydroxyl group being taken into account. The reaction temperature is preferably in the range from room temperature to approximately the boiling point of the solvent. The reaction time is determined as appropriate by monitoring the reaction process by gas chromatography (GC) or silica gel thin-layer chromatography (TLC) because it is desirable from the yield aspect to drive the reaction to completion. The reaction time is typically about 30 minutes to about 2 hours. Intermediate In-B may be recovered from the reaction mixture by ordinary aqueous work-up. If necessary, it may be purified by standard techniques like chromatography and recrystallization.

The second step is to react Intermediate In-B with a haloacetate compound to form an Intermediate In-C. The reaction may be conducted by any well-known organic synthesis method. Specifically, Intermediate In-B and a base are dissolved in a polar aprotic solvent such as N,N-dimethylformamide (DMF) or dimethyl sulfoxide (DMSO), to which the haloacetate compound is added dropwise. Examples of the base used herein include inorganic bases such as potassium carbonate and cesium carbonate and organic bases such as triethylamine and N,N-diisopropylethylamine. On use of the haloacetate compound in which the halogen atom is chlorine or bromine, the reaction rate may be accelerated by adding a catalytic amount of sodium iodide or potassium iodide. The reaction temperature is preferably in the range from room temperature to 100° C. The reaction time is determined as appropriate by monitoring the reaction process by GC or TLC because it is desirable from the yield aspect to drive the reaction to completion. The reaction time is typically about 2 to about 12 hours. Intermediate In-C may be recovered from the reaction mixture by ordinary aqueous work-up. If necessary, it may be purified by standard techniques like chromatography and recrystallization.

The 3rd step is hydrolysis of Intermediate In-C to form an Intermediate In-D. The reaction may be conducted by any well-known method. Specifically. Intermediate In-C is dissolved in 1,4-dioxane, to which a base is added dropwise. The base used herein is typically selected from aqueous solutions of inorganic bases such as sodium hydroxide and potassium hydroxide. The reaction temperature is preferably in the range from room temperature to 60° C. The reaction time is determined as appropriate by monitoring the reaction process by TLC because it is desirable from the yield aspect to drive the reaction to completion. The reaction time is typically about 2 to about 12 hours. At the end, the reaction is quenched by adding an acid such as an aqueous solution of hydrochloric acid or nitric acid. Intermediate In-D may be recovered from the reaction mixture by ordinary aqueous work-up. If necessary, it may be purified by standard techniques like chromatography and recrystallization.

The 4th step is to react Intermediate In-D with an Intermediate In-E to form an Intermediate In-F. In the reaction of the carboxyl group of Intermediate In-D with the hydroxyl group of Intermediate In-E to form an ester bond directly, a condensing agent may be used. Examples of the condensing agent used herein include N,N'-dicyclohexylcarbodiimide, N,N'-diisopropylcarbodiimide, 1-[3-(dimethylamino)propyl]-3-ethylcarbodiimide, and 1-ethyl-3-(3-dimethylaminopropyl)carbodiimide hydrochloride. Of these, 1-ethyl-3-(3-dimethylaminopropyl)carbodiimide hydrochloride is preferably used because the urea compound which is formed as a by-product at the end of reaction is easily removed. The reaction is typically carried out by dissolving Intermediate In-D and Intermediate In-E in a halogen base solvent such as methylene chloride and adding a condensing agent to the solution. The reaction rate may be accelerated by adding N,N-dimethyl-4-dimethylaminopyridine as a catalyst. The reaction time is determined as appropriate by monitoring the reaction process by TLC because it is desirable from the yield aspect to drive the reaction to completion. The reaction time is typically about 12 to about 24 hours. At the end of reaction, the urea compound formed as by-product is removed by filtration or water washing, if necessary. Intermediate In-F may be recovered from the reaction solution by ordinary aqueous work-up. If necessary, it may be purified by standard techniques like chromatography and recrystallization.

The 5th step is an ion exchange of Intermediate In-F with an Intermediate In-G to yield an onium salt (A1-1). Intermediate In-G wherein $Z^-$ is chloride ion, bromide ion, iodide ion or methylsulfate anion is preferred for quantitative progress of the exchange reaction. In view of yield, the progress of reaction is preferably monitored by TLC. Onium salt (A1-1) may be recovered from the reaction mixture by ordinary aqueous work-up. If necessary, it may be purified by standard techniques like chromatography and recrystallization. The ion exchange of the 5th step may be readily conducted by any well-known method with reference to JP-A 2007-145797, for example.

The preparation method according to the aforementioned scheme is merely exemplary, and the method for preparing the inventive onium salt is not limited thereto. While the aforementioned scheme refers to the synthesis of an ester bond-containing compound, an onium salt having an ether bond, sulfonate bond, carbonate bond or carbamate bond can be synthesized by the skilled artisan using an organic chemistry method within the range of common knowledge.

Resist Composition

Another embodiment of the invention is a chemically amplified negative resist composition which essentially contains a photoacid generator in the form of the onium salt defined above. Preferably the resist composition contains a base polymer of specific structure as well as the onium salt.

In the resist composition, the photoacid generator in the form of the onium salt is present in an amount of preferably 0.01 to 100 parts by weight, more preferably 0.05 to 50 parts by weight per 100 parts by weight of the base polymer, as viewed from the standpoints of sensitivity and acid diffusion controlling effect.

Base Polymer

The base polymer in the resist composition is a polymer comprising recurring units having the following formula (B1) and recurring units having the following formula (B2), which are also referred to as recurring units (B1) and (B2), respectively.

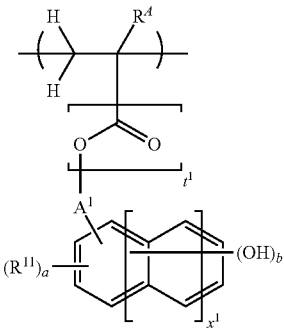

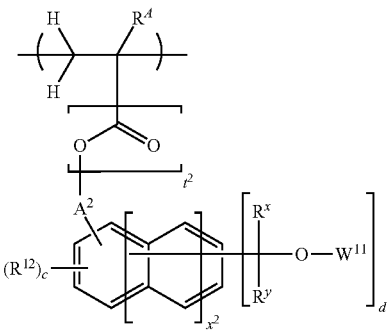

The recurring units (B1) are units for establishing etch resistance and for providing adhesion to substrates and dissolution in alkaline developer. The recurring units (B2) are units for allowing the acid labile group to undergo elimination reaction under the action of acid which is generated from the acid generator upon exposure to high-energy radiation, for thereby inducing alkaline insolubilization and crosslinking reaction among polymer molecules. The recurring units (B2) act to promote the progress of negative reaction to enhance resolution performance.

In formulae (B1) and (B2), $R^A$ is hydrogen, fluorine, methyl or trifluoromethyl.

$R^{11}$ and $R^{12}$ are each independently halogen, an optionally halogenated $C_1$-$C_6$ saturated hydrocarbyl group, optionally halogenated $C_2$-$C_8$ saturated hydrocarbylcarbonyloxy group, or optionally halogenated $C_1$-$C_6$ saturated hydrocarbyloxy group. The saturated hydrocarbyl group and the saturated hydrocarbyl moiety in the saturated hydrocarbylcarbonyloxy group and saturated hydrocarbyloxy group may be straight, branched or cyclic. Examples thereof include alkyl groups such as methyl, ethyl, propyl, isopropyl, butyl, pentyl and hexyl, cycloalkyl groups such as cyclopropyl, cyclobutyl, cyclopentyl and cyclohexyl, and a combination thereof. As long as the carbon count does not exceed the upper limit, the polymer is fully dissolvable in alkaline developer.

In formulae (B1) and (B2), $A^1$ and $A^2$ are each independently a single bond or a $C_1$-$C_{10}$ saturated hydrocarbylene group in which a constituent —$CH_2$— may be replaced by —O—. The saturated hydrocarbylene group may be straight, branched or cyclic and examples thereof include alkanediyl groups such as methylene, ethane-1,1-diyl, ethane-1,2-diyl, propane-1,2-diyl, propane-1,3-diyl, butane-1,4-diyl, pentane-1,5-diyl, and hexane-1,6-diyl; cyclic saturated hydrocarbylene groups such as cyclopropanediyl, cyclobutanediyl, cyclopentanediyl, and cyclohexanediyl: and combinations thereof. For the saturated hydrocarbylene group containing an ether bond, in case of $t^1=1$ in formula (B1), the ether bond may be situated at any position excluding the position between the carbon at α-position and the carbon at β-position relative to the ester oxygen. In case of $t^1=0$, the atom attached to the main chain becomes the ether oxygen atom, and a second ether bond may be situated at any position excluding the position between the carbon at α-position and the carbon at β-position relative to the ether oxygen atom. Since the carbon count of the saturated hydrocarbylene group is 10 or less, the polymer is fully dissolvable in alkaline developer.

In formula (B2), $W^{11}$ is hydrogen, a $C_1$-$C_{10}$ aliphatic hydrocarbyl group, or an optionally substituted aryl group. The aliphatic hydrocarbyl group may be straight, branched or cyclic and examples thereof include alkyl groups such as methyl, ethyl, propyl, isopropyl, and cyclic aliphatic hydrocarbyl groups such as cyclopentyl, cyclohexyl and adamantyl. Typical of the aryl group is phenyl. A constituent —CH$_2$— in the aliphatic hydrocarbyl group may be replaced by —O—, —C(=O)—, —O—C(=O)— or —C(=O)—O—. The constituent —CH$_2$— in the hydrocarbyl group may bond to the oxygen atom in formula (B2). Typical of the group after such replacement is methylcarbonyl.

In formula (B2), $R^x$ and $R^y$ are each independently hydrogen, or a $C_1$-$C_{15}$ saturated hydrocarbyl group which may be substituted with a hydroxyl or saturated hydrocarbyloxy moiety, or an optionally substituted aryl group. Both $R^x$ and $R^y$ are not hydrogen at the same time. $R^x$ and $R^y$ may bond together to form a ring with the carbon atom to which they are attached. The saturated hydrocarbyl group may be straight, branched or cyclic and examples thereof include alkyl groups such as methyl, ethyl, propyl, butyl and structural isomers thereof, and substituted forms of these groups in which some hydrogen is substituted by a hydroxyl moiety or saturated hydrocarbyloxy moiety.

In formulae (B1) and (B2), $t^1$ and $t^2$ are each independently 0 or 1. The subscripts $x^1$ and $x^2$ are each independently an integer of 0 to 2, and the relevant structure represents a benzene skeleton in case of $x^1$ or $x^2=0$, a naphthalene skeleton in case of $x^1$ or $x^2=1$, and an anthracene skeleton in case of $x^1$ or $x^2=2$. The subscript "a" is an integer meeting $0 \leq a \leq 5+2x^1-b$, c is an integer meeting $0 \leq c \leq 5+2x^2-d$, b and d are each independently an integer of 1 to 3. In case of $x^1=0$, preferably "a" is an integer of 0 to 3, and b is an integer of 1 to 3; in case of $x^1=1$ or 2, preferably "a" is an integer of 0 to 4, and b is an integer of 1 to 3. In case of $x^2=0$, preferably c is an integer of 0 to 3, and d is an integer of 1 to 3; in case of $x^2=1$ or 2, preferably c is an integer of 0 to 4, and d is an integer of 1 to 3.

In the embodiment wherein $t^1=0$ and $A^1$ is a single bond, that is, the aromatic ring directly bonds to the polymer main chain, or differently stated, the unit is free of the linker (—CO—O—$A^1$-), the recurring units (B1) are preferably recurring units having the following formula (B1-1), which are also referred to as recurring units (B1-1), hereinafter.

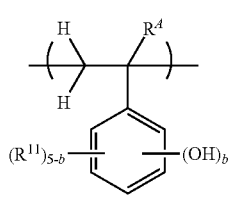

(B1-1)

Herein $R^A$, $R^{11}$ and b are as defined above.

Preferred examples of the recurring unit (B1) include units derived from 3-hydroxystyrene, 4-hydroxystyrene, 5-hydroxy-2-vinylnaphthalene, and 6-hydroxy-2-vinylnaphthalene. Units of the formulae shown below are more preferred.

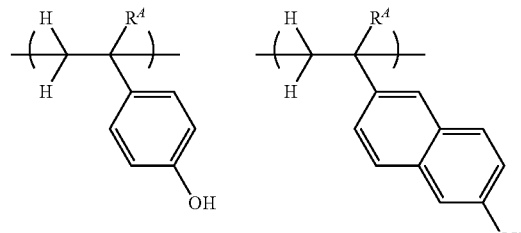

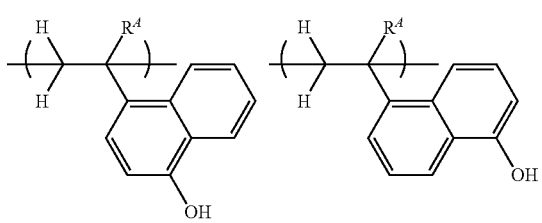

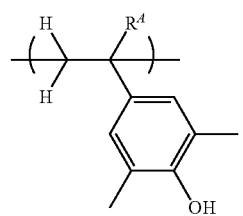

Herein $R^A$ is as defined above.

In the embodiment wherein $t^1=1$, that is, the unit has an ester bond as the linker, preferred examples of the recurring unit (B1) are shown below, but not limited thereto.

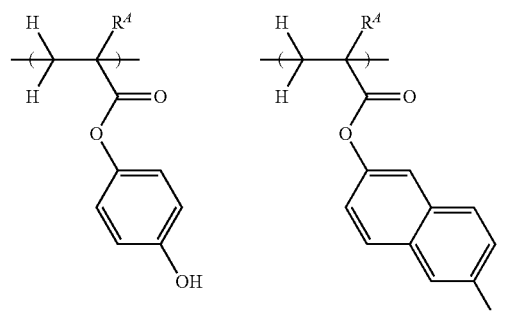

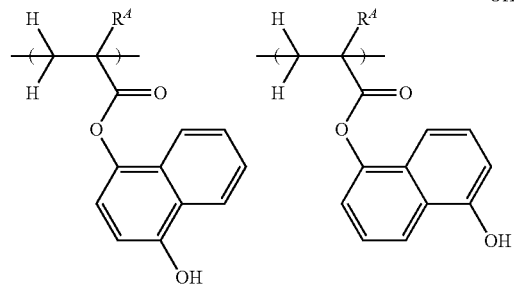

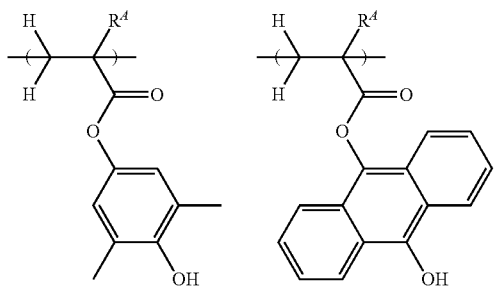
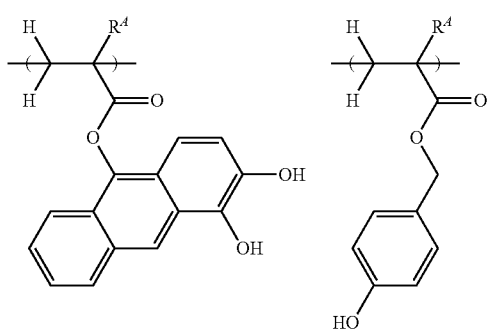
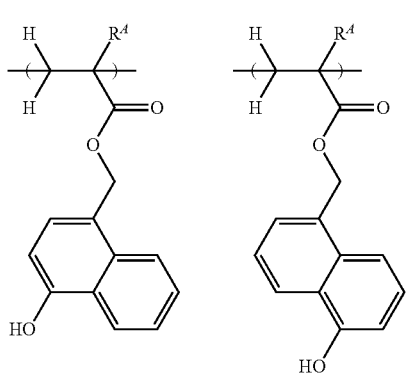
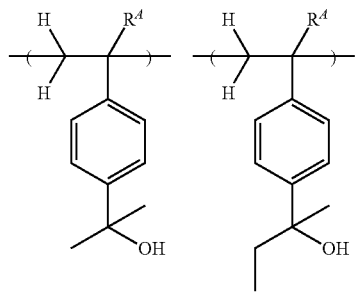
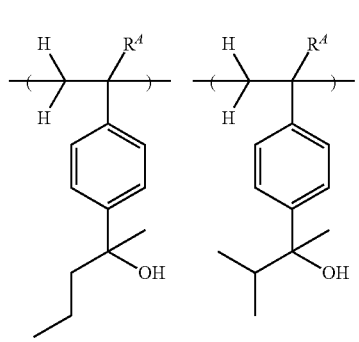
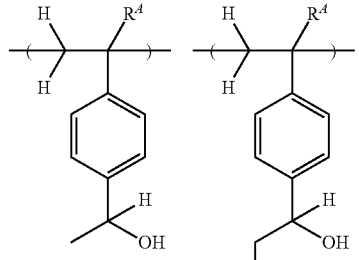
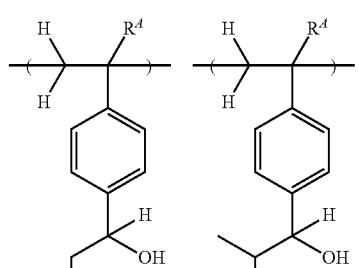
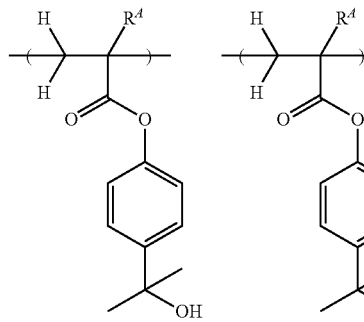
Herein $R^A$ is as defined above.
The recurring units (B2) are preferably recurring units having the following formula (B2-1), which are also referred to as recurring units (B2-1), hereinafter.
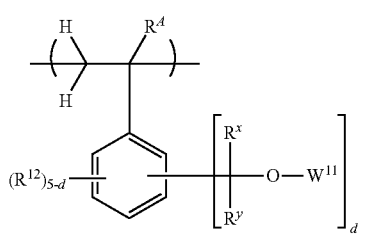
(B2-1)
Herein $R^A$, $R^{12}$, $R^x$, $R^y$, $W^{11}$ and d are as defined above.
Preferred examples of the recurring unit (B2) are shown below, but not limited thereto.

-continued
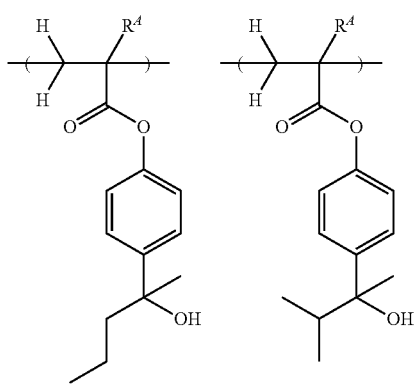
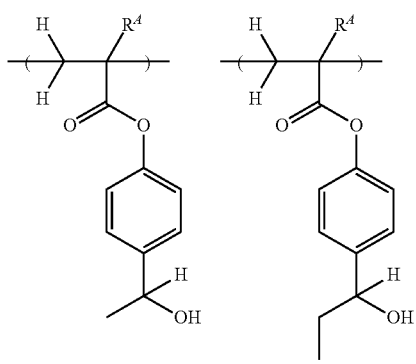
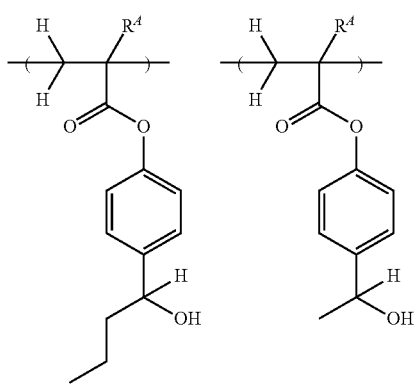
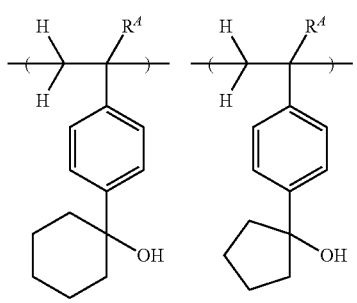
-continued
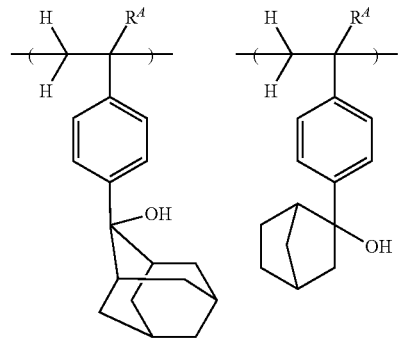
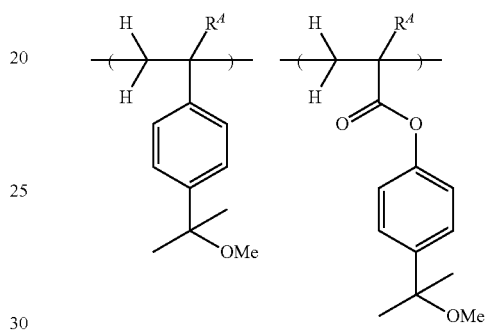
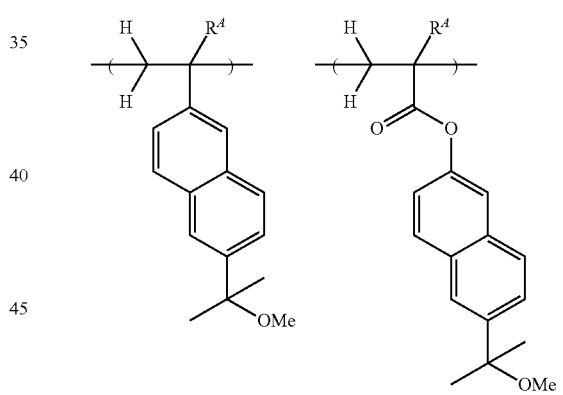
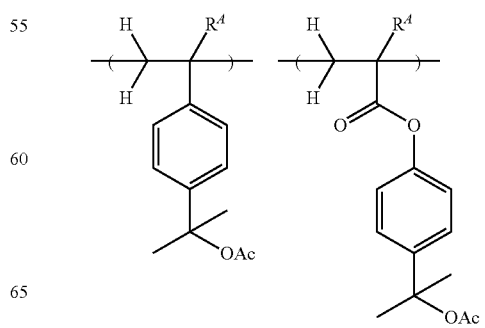

139
-continued
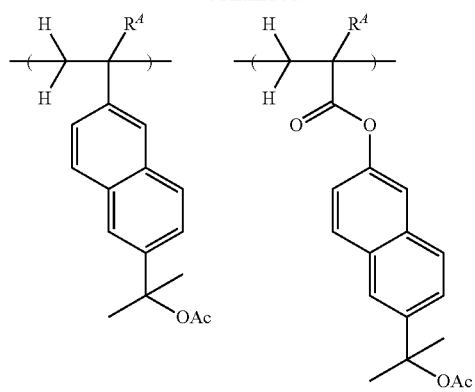
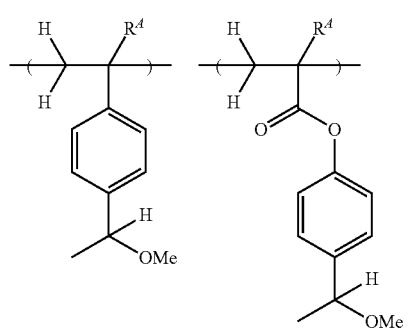
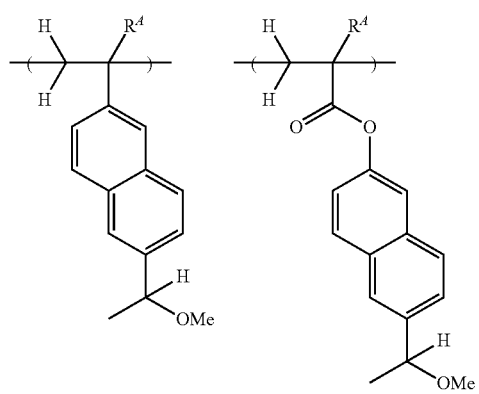
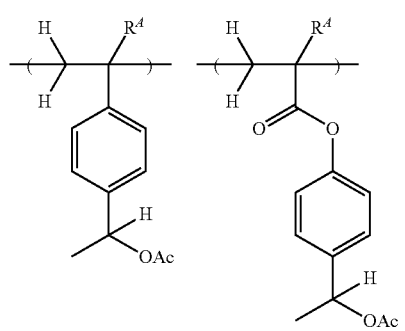
140
-continued
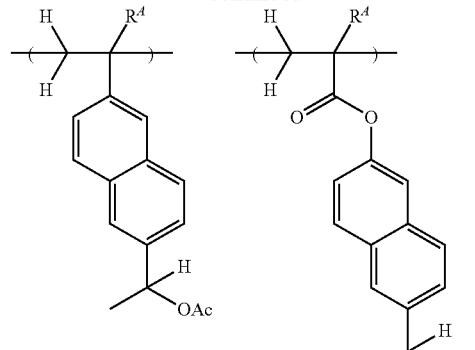
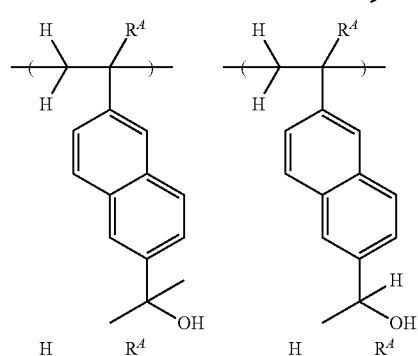
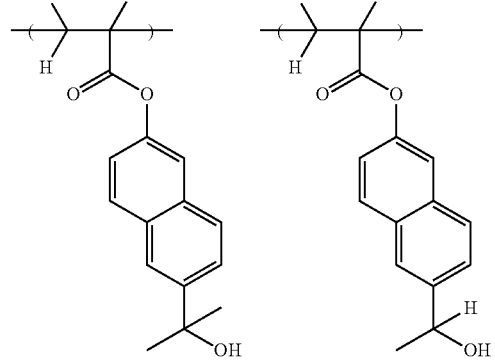
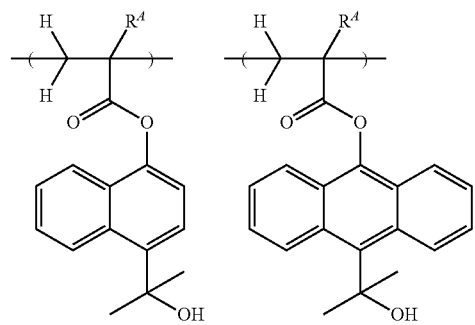
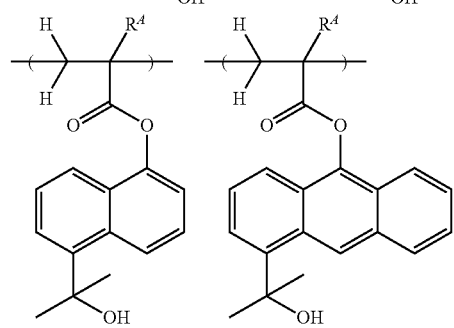

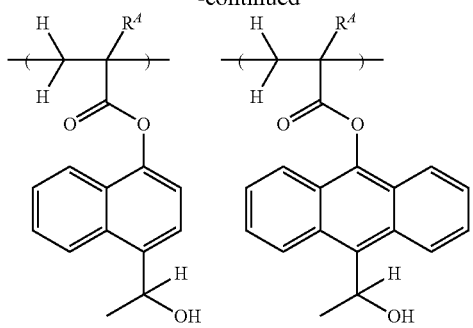
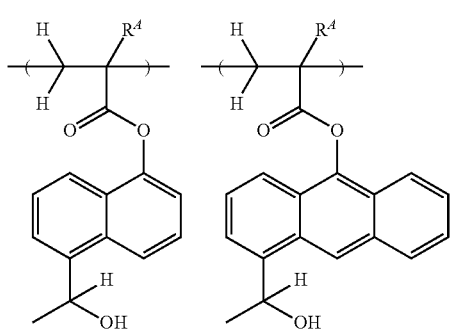
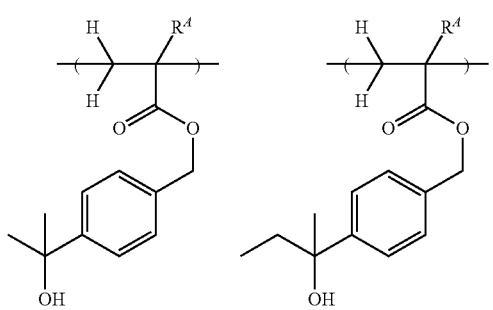
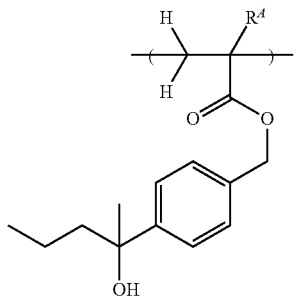
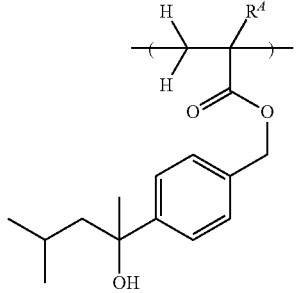
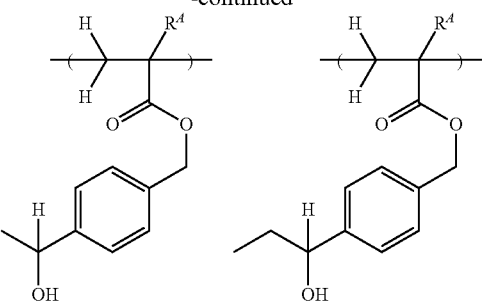
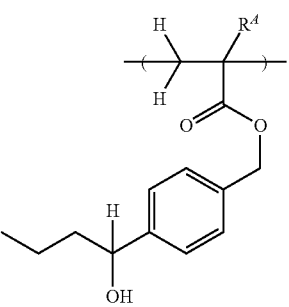
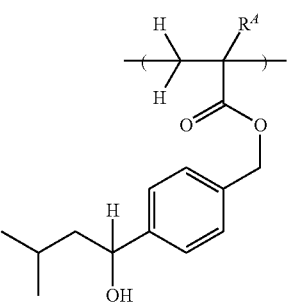
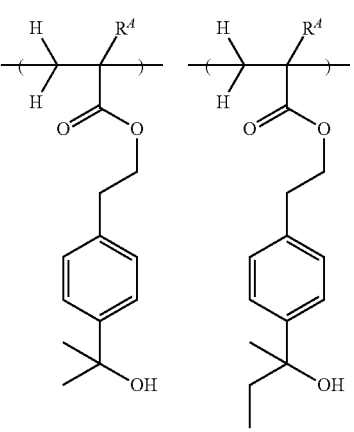

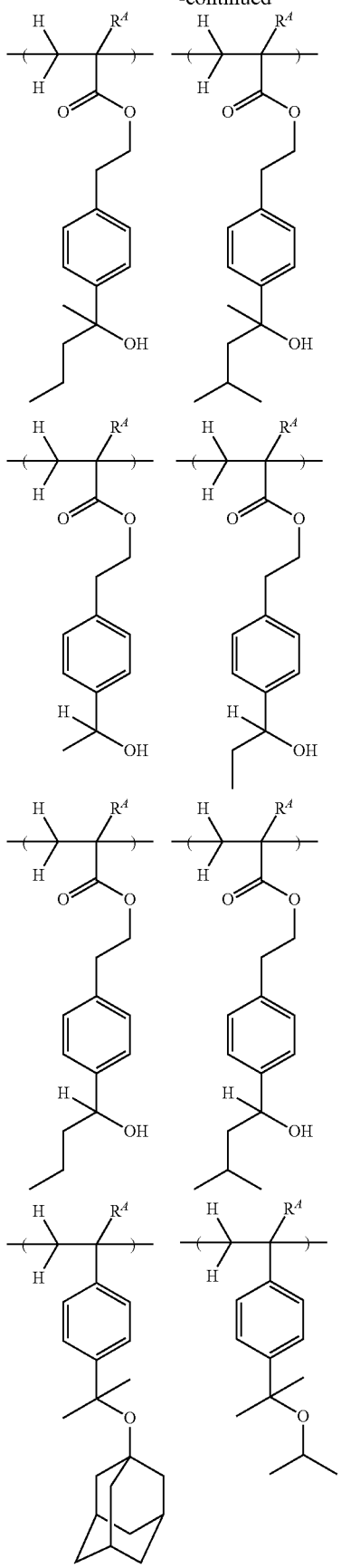

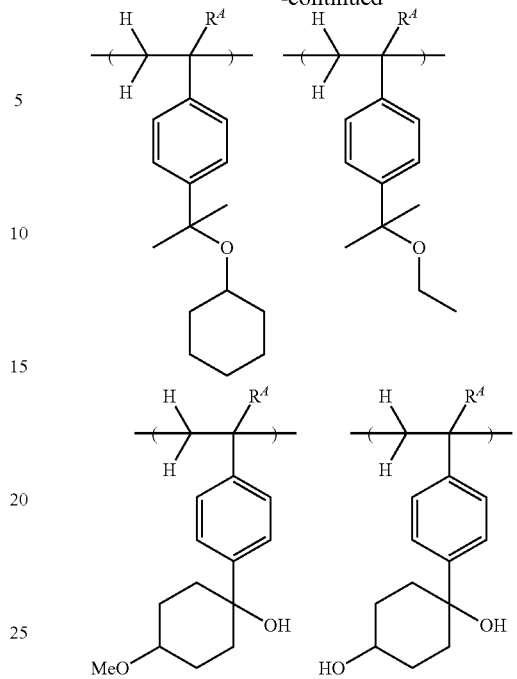

The content of recurring units is determined so as to establish a high contrast between the exposed region (which turns negative) and the unexposed region (which does not turn negative) upon exposure to high-energy radiation for the purpose of obtaining a high resolution. As to the content of recurring units (B1), the lower limit is preferably 30 mol %, more preferably 40 mol %, even more preferably 50 mol %, and the upper limit is preferably 95 mol %, more preferably 90 mol %, even more preferably 80 mol %, based on the overall recurring units of the base polymer.

As to the content of recurring units (B2), the lower limit is preferably 5 mol %, more preferably 10 mol %, even more preferably 20 mol %, and the upper limit is preferably 70 mol %, more preferably 60 mol %, even more preferably 50 mol %, based on the overall recurring units of the base polymer.

Particularly when the base polymer contains recurring units (B1-1) and (B2-1), the recurring units (B1-1) contribute to a further improvement in etch resistance and improvements in adhesion to the substrate and dissolution in alkaline developer whereas the recurring units (B2-1) contribute to a more efficient progress of negative reaction and a further improvement in resolution.

For the purpose of enhancing etch resistance, the base polymer may further comprise recurring units of at least one type selected from recurring units having the formula (B3), recurring units having the formula (B4), and recurring units having the formula (B5). It is noted that these units are also referred to as recurring units (B3), (B4) and (B5), hereinafter.

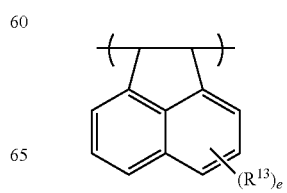

(B3)

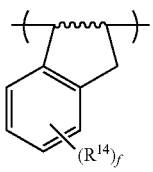

(B4)

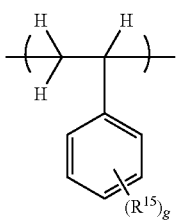

(B5)

In formulae (B3) and (B4), $R^{13}$ and $R^{14}$ are each independently hydroxyl, halogen, acetoxy, an optionally halogenated $C_1$-$C_8$ alkyl group, optionally halogenated $C_1$-$C_8$ saturated hydrocarbyloxy group, optionally halogenated $C_2$-$C_8$ saturated hydrocarbylcarbonyl group, or optionally halogenated $C_2$-$C_8$ saturated hydrocarbylcarbonyloxy group, with the proviso that $R^{13}$ and $R^{14}$ are not acid labile groups.

In formula (B5), $R^{15}$ is halogen, acetoxy, an optionally halogenated $C_1$-$C_8$ alkyl group, optionally halogenated $C_1$-$C_8$ saturated hydrocarbyloxy group, optionally halogenated $C_2$-$C_8$ saturated hydrocarbylcarbonyl group, or optionally halogenated $C_2$-$C_8$ saturated hydrocarbylcarbonyloxy group, with the proviso that $R^{15}$ is not an acid labile group.

In formulae (B3) to (B5), e, f and g are each independently an integer of 0 to 4.

When constituent units of at least one type selected from recurring units (B3) to (B5) are included, not only the aromatic ring inherently possesses etch resistance, but the ring structure incorporated in the main chain also exerts the effect of improving etch resistance and resistance to EB which is irradiated for pattern inspection.

Of the recurring units (B3) to (5), units of one type or a mixture of two or more types may be used. The content of recurring units (B3) to (B5) is determined so as to achieve the effect of improving etch resistance, and its lower limit is preferably 2 mol %, more preferably 5 mol % and its upper limit is preferably 30 mol %, more preferably 20 mol %, based on the overall recurring units of the base polymer.

Other Components

In the chemically amplified negative resist composition, other components such as an organic solvent, quencher, crosslinker, and surfactant may be contained in a suitable combination, if desired. The resist composition thus constricted can form a negative pattern of good profile which is restrained in the dissolution of exposed region in alkaline developer and minimized in top loss, as compared with negative patterns formed from conventional negative resist compositions. The resist film has a high dissolution contrast, high resolution capability, exposure latitude, process adaptability, a good pattern profile after exposure, and minimal proximity bias because of controlled acid diffusion. Because of these advantages, the composition is readily implemented in practice and best suited as a VLSI-forming resist material.

Organic Solvent

The organic solvent used herein is not particularly limited as long as the foregoing and other components are soluble therein. Examples of the organic solvent are described in JP-A 2008-111103, paragraphs [0144]-[0145] (U.S. Pat. No. 7,537,880). Exemplary solvents include ketones such as cyclohexanone, cyclopentanone, methyl-2-n-pentyl ketone and 2-heptanone: alcohols such as 3-methoxybutanol, 3-methyl-3-methoxybutanol, l-methoxy-2-propanol, l-ethoxy-2-propanol, and diacetone alcohol (DAA): ethers such as propylene glycol monomethyl ether (PGME), ethylene glycol monomethylether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

Of the above organic solvents, l-ethoxy-2-propanol, PGMEA, cyclohexanone, γ-butyrolactone, and a mixture thereof are preferred because the onium salt is fully soluble therein.

The organic solvent is preferably added in an amount of 200 to 12,000 parts, and more preferably 400 to 10,000 parts by weight per 100 pats by weight of the base polymer.

Quencher

The quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl group, ether bond, ester bond, lactone ring, cyano group, or sulfonic acid ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of carboxylic acids which are not fluorinated at α-position as described in U.S. Pat. No. 8,795,942 (JP-A 2008-158339) may also be used as the quencher. While an α-fluorinated sulfonic acid, imide acid, and methide acid are necessary to deprotect the acid labile group, an α-non-fluorinated carboxylic acid is released by salt exchange with an α-non-fluorinated onium salt. An α-non-fluorinated carboxylic acid functions as a quencher because it does not induce substantial deprotection reaction.

Examples of the onium salt of α-non-fluorinated carboxylic acid include compounds having the formula (C1).

(C1)

In formula (C1), $R^{101}$ is hydrogen or a $C_1$-$C_{40}$ hydrocarbyl group which may contain a heteroatom, excluding the hydrocarbon group in which the hydrogen atom bonded to the carbon at α-position relative to the carboxyl group is substituted by fluorine or fluoroalkyl.

The hydrocarbyl group may be saturated or unsaturated and straight, branched or cyclic. Examples thereof include alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; alkenyl groups such as vinyl, allyl, propenyl, butenyl and hexenyl; cyclic unsaturated aliphatic hydrocarbyl groups such as cyclohexenyl; aryl groups such as phenyl, naphthyl, alkylphenyl groups (e.g., 2-methylphenyl, 3-methylphenyl, 4-methylphenyl, 4-ethylphenyl, 4-tert-butylphenyl, 4-n-butylphenyl), dialkylphenyl groups (e.g., 2,4-dimethylphenyl and 2,4,6-triisopropylphenyl), alkylnaphthyl groups (e.g., methylnaphthyl and ethylnaphthyl), dialkylnaphthyl groups (e.g., dimethylnaphthyl and diethylnaphthyl); and aralkyl groups such as benzyl, 1-phenylethyl and 2-phenylethyl.

In these groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, thioether bond, ester bond, sulfonic acid ester bond, carbonate bond, lactone ring, sultone ring, carboxylic anhydride, or haloalkyl moiety. Suitable heteroatom-containing hydrocarbyl groups include heteroaryl groups such as thienyl; alkoxyphenyl groups such as 4-hydroxyphenyl, 4-methoxyphenyl, 3-methoxyphenyl, 2-methoxyphenyl, 4-ethoxyphenyl, 4-tert-butoxyphenyl, 3-tert-butoxyphenyl: alkoxynaphthyl groups such as methoxynaphthyl, ethoxynaphthyl, n-propoxynaphthyl and n-butoxynaphthyl; dialkoxynaphthyl groups such as dimethoxynaphthyl and diethoxynaphthyl; and aryloxoalkyl groups, typically 2-aryl-2-oxoethyl groups such as 2-phenyl-2-oxoethyl, 2-(1-naphthyl)-2-oxoethyl and 2-(2-naphthyl)-2-oxoethyl.

In formula (C1), Mq$^+$ is an onium cation. The onium cation is preferably selected from sulfonium, iodonium and ammonium cations, more preferably sulfonium and iodonium cations. Exemplary sulfonium cations are as exemplified above for the sulfonium cation having formula (A1-a) wherein p=0. Exemplary iodonium cations are as exemplified above for the iodonium cation having formula (A1-b) wherein q=0. Exemplary ammonium cations are as exemplified above for the ammonium cation having formula (A1-c) wherein r=0.

A sulfonium salt of iodized benzene ring-containing carboxylic acid having the formula (C2) is also useful as the quencher.

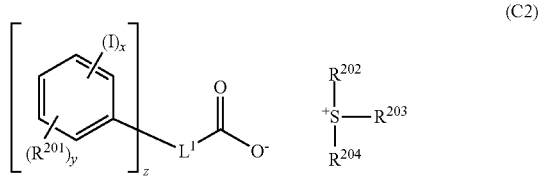

(C2)

In formula (C2), R$^{201}$ is hydroxyl, fluorine, chlorine, bromine, amino, nitro, cyano, or a C$_1$-C$_6$ saturated hydrocarbyl, C$_1$-C$_6$ saturated hydrocarbyloxy, C$_2$-C$_6$ saturated hydrocarbylcarbonyloxy or C$_1$-C$_4$ saturated hydrocarbylsulfonyloxy group, in which some or all hydrogen may be substituted by halogen, or —N(R$^{201A}$)—C(=O)—R$^{201B}$ or —N(R$^{201A}$)—C(=O)—O—R$^{201B}$. R$^{201A}$ is hydrogen or a C$_1$-C$_6$ saturated hydrocarbyl group. R$^{201B}$ is a C$_1$-C$_6$ saturated hydrocarbyl or C$_2$-C$_8$ unsaturated aliphatic hydrocarbyl group.

In formula (C$_2$), x is an integer of 1 to 5, y is an integer of 0 to 3, and z is an integer of 1 to 3. L$^1$ is a single bond, or a C$_1$-C$_{20}$ (z+1)-valent linking group which may contain at least one moiety selected from ether bond, carbonyl moiety, ester bond, amide bond, sultone ring, lactam ring, carbonate moiety, halogen, hydroxyl moiety, and carboxyl moiety. The saturated hydrocarbyl, saturated hydrocarbyloxy, saturated hydrocarbylcarbonyloxy, and saturated hydrocarbylsulfonyloxy groups may be straight, branched or cyclic. Groups R$^{201}$ may be the same or different when y and/or z is 2 or 3.

In formula (C2), R$^{202}$, R$^{203}$ and R$^{204}$ are each independently halogen, or a C$_1$-C$_{20}$ hydrocarbyl group which may contain a heteroatom. The hydrocarbyl group may be saturated or unsaturated and straight, branched or cyclic. Examples thereof include C$_1$-C$_{20}$ alkyl, C$_2$-C$_{20}$ alkenyl, C$_6$-C$_{20}$ aryl, and C$_7$-C$_{20}$ aralkyl groups. In these groups, some or all hydrogen may be substituted by hydroxyl, carboxyl, halogen, oxo, cyano, nitro, sultone, sulfone, or sulfonium salt-containing moiety, or some carbon may be replaced by an ether bond, ester bond, carbonyl moiety, amide bond, carbonate moiety or sulfonic acid ester bond. Also R$^{202}$ and R$^{203}$ may bond together to form a ring with the sulfur atom to which they are attached.

Examples of the compound having formula (C2) include those described in U.S. Pat. No. 10,295,904 (JP-A 2017-219836). These compounds exert a sensitizing effect due to remarkable absorption and an acid diffusion controlling effect.

Weak acid betaine compounds are also useful as the quencher. Non-limiting examples thereof are shown below.

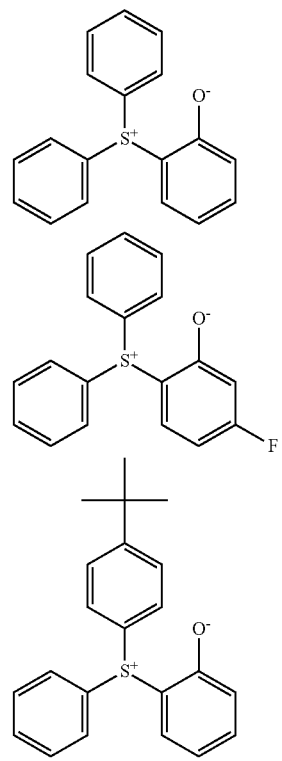

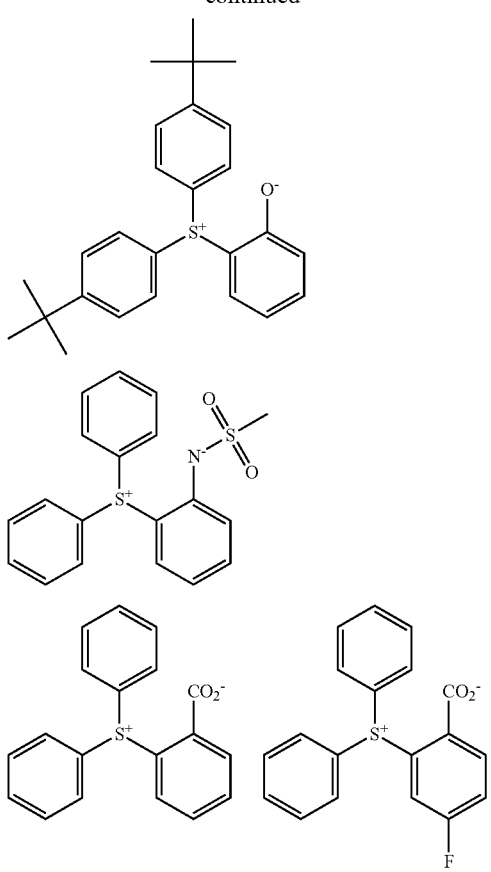

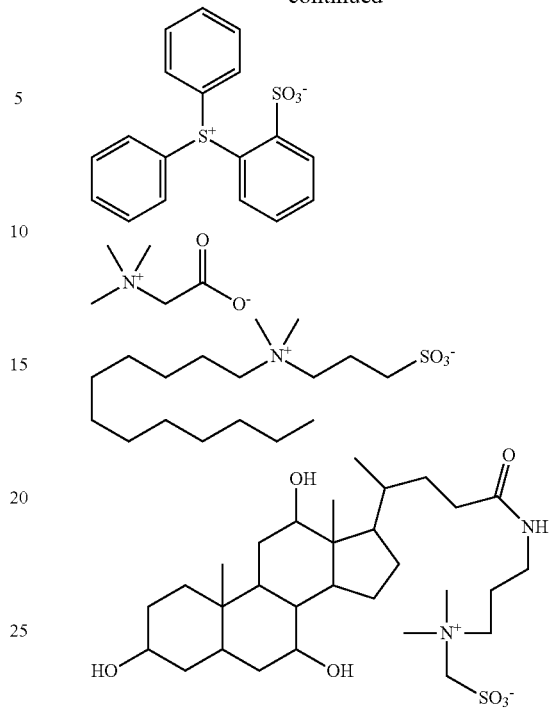

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

When used, the quencher is preferably added in an amount of 0 to 5 parts, more preferably 0 to 4 parts by weight per 100 parts by weight of the base polymer.

Crosslinker

The resist composition may comprise a crosslinker. Suitable crosslinkers include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyloxy group. These compounds may be used as an additive or introduced into a polymer side chain as a pendant. Hydroxy-containing compounds may also be used as the crosslinker.

Examples of the epoxy compound include tris(2,3-epoxypropyl) isocyanurate, trimethylmethane triglycidyl ether, trimethylolpropane triglycidyl ether, and trimethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamme, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyloxy group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

When the resist composition contains a crosslinker, the crosslinker is preferably added in an amount of 2 to 50 parts, more preferably 5 to 30 parts by weight per 100 parts by weight of the base polymer. As long as the amount of crosslinker is in the range, the risk of bridging pattern features to reduce resolution is minimized. The crosslinker may be used alone or in admixture.

Surfactant

The resist composition may contain any conventional surfactants for facilitating to coat the composition to the substrate. Since a number of surfactants are known in the art, for example, PF-636 (Omnova Solutions), FC-4430 (3M), and those described in JP-A 2004-115630, any suitable one may be chosen therefrom. The amount of surfactant added is preferably 0 to 5 parts by weight per 100 parts by weight of the base polymer.

Pattern Forming Process

A further embodiment of the invention is a process for forming a resist pattern comprising the steps of applying the chemically amplified negative resist composition onto a substrate to form a resist film thereon, exposing patternwise the resist film to high-energy radiation, and developing the exposed resist film in an alkaline developer.

The resist composition is first applied onto a substrate on which an integrated circuit is to be formed (e.g., Si, $SiO_2$, SiN, SiON, TiN. WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating. The coating is prebaked on a hot plate at a temperature of preferably 60 to 150° C. for 1 to 20 minutes, more preferably at 80 to 140° C. for 1 to 10 minutes. The resulting resist film is generally 0.03 to 2 µm thick.

The resist film is then exposed to a desired pattern of high-energy radiation such as UV, deep-UV, excimer laser radiation (KrF, ArF, etc.), EUV, x-ray, γ-ray, synchrotron radiation or EB. Exposure using KrF excimer laser, EUV or EB is preferred.

When UV, deep-UV, excimer laser, EUV, x-ray, γ-ray or synchrotron radiation is used as the high-energy radiation, the resist film is exposed thereto through a mask having a desired pattern in a dose of preferably 1 to 200 mJ/cm², more preferably 10 to 100 mJ/cm². When EB is used as the high-energy radiation, the resist film is exposed thereto directly in a dose of preferably 1 to 300 µC/cm², more preferably 10 to 200 µC/cm².

After the exposure, the resist film may be baked (PEB) on a hotplate preferably at 60 to 150° C. for 1 to 20 minutes, more preferably at 80 to 140° C. for 1 to 10 minutes.

After the exposure or PEB, the resist film is developed in a developer in the form of an aqueous alkaline solution for preferably 0.1 to 3 minutes, more preferably 0.5 to 2 minutes by conventional techniques such as dip, puddle and spray techniques. A typical developer is a0.1 to 5 wt %, preferably 2 to 3 wt % aqueous solution of tetramethylammonium hydroxide (TMAH) or another alkali. In this way, the desired pattern is formed on the substrate.

After the resist film is formed, rinsing with deionized water, known as post-soaking, may be carried out to extract the acid generator or the like from the film surface and to wash away particles. The resist film may also be rinsed (post-soaking) for removing any residual water on the film after exposure.

EXAMPLES

Examples of the invention are given below by way of illustration and not by way of limitation. The abbreviation "pbw" is parts by weight. For all polymers, Mw and Mn are determined by GPC versus polystyrene standards using THF solvent. THF is tetrahydrofuran, DMF is dimethylformamide, MIBK is methyl isobutyl ketone, and PGMEA is propylene glycol monomethyl ether acetate. Analysis is made by IR spectroscopy, $^1$H-NMR spectroscopy, and time-of-flight mass spectrometry (TOF-MS) using analytic instruments as shown below.

IR: NICOLET 6700 by Thermo Fisher Scientific Inc.
$^1$H-NMR: ECA-500 by JEOL Ltd.
MALDI TOF-MS: S3000 by JEOL Ltd.

[1] Synthesis of Onium Salts

Example 1-1

Synthesis of PAG-1
(1) Synthesis of Intermediate In-1

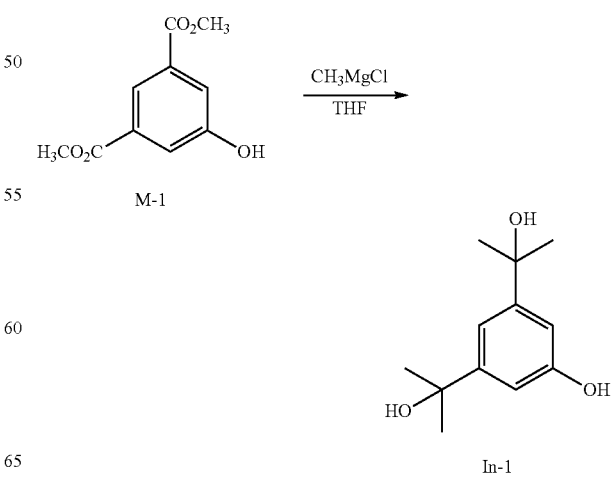

In nitrogen atmosphere, a flask was charged with 145.9 g (6 equivalents relative to M-1) of magnesium, 3,000 g of THF, and chloromethane, from which a Grignard reagent was prepared. A solution of 210 g of M-1 in 500 g of THF was added dropwise to the flask at a temperature of 40-55° C. (internal temperature, hereinafter). At the end of addition, the solution was aged at an internal temperature of 50° C. for 3 hours. After aging, the reaction system was cooled, whereupon an aqueous solution of 600 g of ammonium chloride and 1,800 g of 3.0 wt % hydrochloric acid aqueous solution was added dropwise to quench the reaction. This was followed by extraction with 2,000 mL of ethyl acetate, ordinary aqueous work-up, solvent distillation, and recrystallization from hexane. There was obtained an Intermediate In-1 as white crystals (amount 172.2 g, yield 82%).

(2) Synthesis of Intermediate In-2

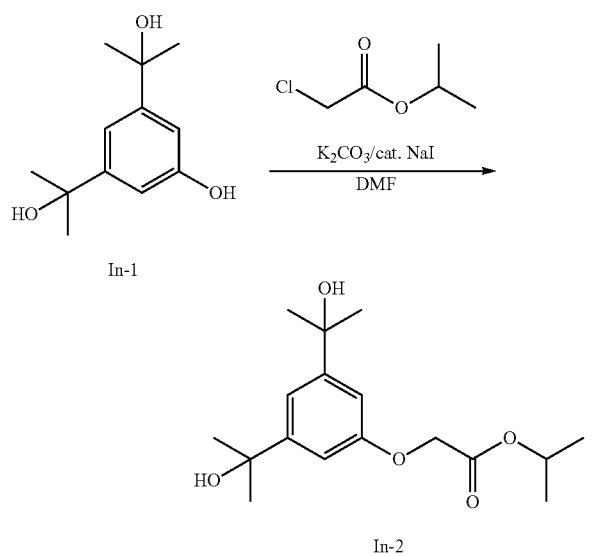

In nitrogen atmosphere, a flask was charged with 105.1 g of Intermediate In-1, 76.0 g of potassium carbonate, 7.5 g of sodium iodide, and 350 g of DMF, which were stirred at an internal temperature of 50° C. for 30 minutes. To the flask, a solution of 82.0 g of isopropyl chloroacetate in 80 g of DMF was added dropwise. At the end of addition, the solution was aged for 18 hours while keeping the internal temperature of 50° C. After aging, the reaction system was cooled, whereupon a solution of 150.4 g of 20 wt % hydrochloric acid aqueous solution and 500 g of water was added dropwise to quench the reaction. Thereafter, 500 mL of ethyl acetate and 250 mL of toluene were added to the solution to extract the end compound, followed by ordinary aqueous work-up, solvent distillation, and recrystallization from hexane. There was obtained an Intermediate In-2 as white crystals (amount 136.1 g. yield 88%).

(3) Synthesis of Intermediate In-3

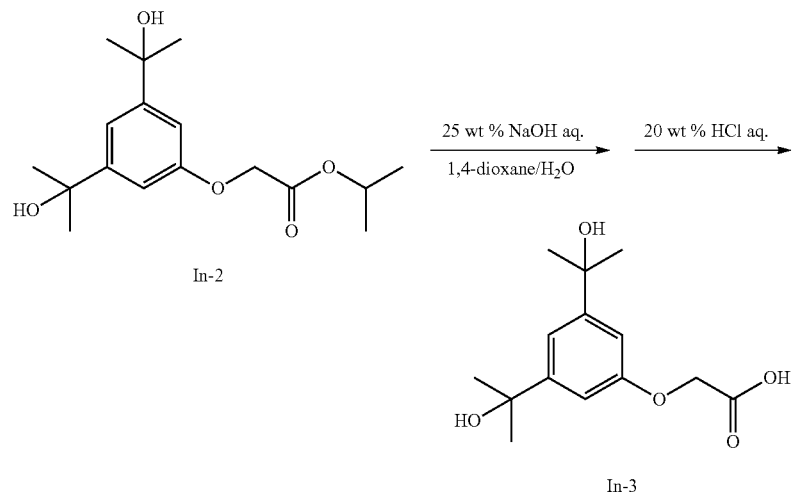

In nitrogen atmosphere, a flask was charged with 136.1 g of Intermediate In-2 and 550 g of 1,4-dioxane and cooled in an ice bath. To the flask, 84.2 g of 25 wt % sodium hydroxide aqueous solution was added dropwise. At the end of addition, the solution was heated at an internal temperature of 40° C. and aged for 12 hours. After aging, the reaction solution was ice cooled, whereupon 100.7 g of 20 wt % hydrochloric acid aqueous solution was added dropwise to quench the reaction. This was followed by extraction with 1,000 mL of ethyl acetate, ordinary aqueous work-up, solvent distillation, and recrystallization from hexane. There was obtained an Intermediate In-3 as white crystals (amount 85.5 g, yield 73%).

(4) Synthesis of Intermediate In-4

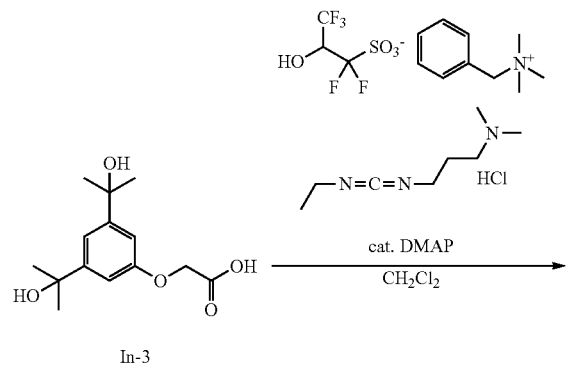

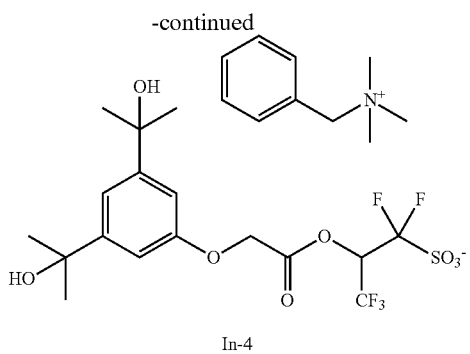

In-4

In nitrogen atmosphere, a flask was charged with 26.8 g of Intermediate In-3, 39.8 g of benzyltrimethylammonium 1,1,3,3,3-pentafluoro-2-hydroxypropane-1-sulfonate, 1.2 g of N,N-dimethyl-4-aminopyridine (DMAP), and 200 g of methylene chloride and cooled in an ice bath. To the flask, 23.0 g of 1-ethyl-3-(3-dimethylaminopropyl)carbodiimide hydrochloride in powder form was added while keeping the internal temperature below 20° C.

At the end of addition, the reaction mixture was heated at room temperature and aged for 12 hours. After aging, water was added to quench the reaction. This was followed by ordinary aqueous work-up, solvent distillation, and azeotropic dehydration with 100 g of MIBK. There was obtained an Intermediate In-4 as oily matter (amount 51.3 g, yield 81%).

(5) Synthesis of PAG-1

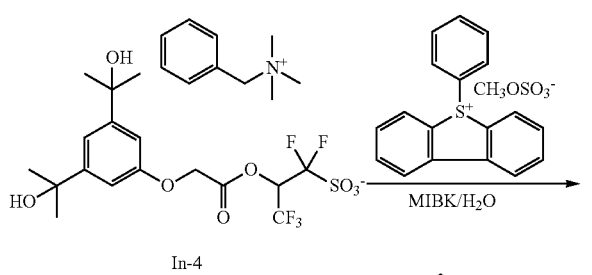

PAG-1

In nitrogen atmosphere, 12.3 g of Intermediate In-4, 7.0 g of 5-phenyldibenzothiophenium methylsulfate, 75 g of MIBK, 25 g of methylene chloride, and 60 g of water were combined and stirred for 30 minutes. The organic layer was taken out, washed with water, and concentrated under reduced pressure. Then diisopropyl ether was added to the concentrate for recrystallization. There was obtained the target compound PAG-1 as white crystals (amount 10.0 g, yield 83%).

PAG-1 was analyzed by IR spectroscopy and TOF-MS, with the data shown below. FIG. 1 is the $^1$H-NMR/DMSO-$d_6$ spectrum of PAG-1.

IR (D-ATR): ν=3453, 3091, 2975, 2935, 1798, 1594, 1476, 1449, 1435, 1372, 1330, 1279, 1263, 1247, 1218, 1172, 1145, 1103, 1068, 998, 962, 936, 923, 859, 833, 782, 758, 733, 707, 680, 644, 613, 575, 552, 524, 500, 489, 422 cm$^{-1}$

MALDI TOF-MS

Positive M$^+$ 261 (corresponding to $C_{18}H_{13}S^+$)

Negative M$^-$ 479 (corresponding to $C_{17}H_{20}F_5O_8S^-$)

Examples 1-2 to 1-14 and Comparative Examples 1-1 to 1-4

Synthesis of PAG-2 to PAG-14 and cPAG-1 to cPAG-4

Onium salts PAG-2 to PAG-14 and cPAG-1 to cPAG-4 as shown below were synthesized by well-known organic synthesis methods.

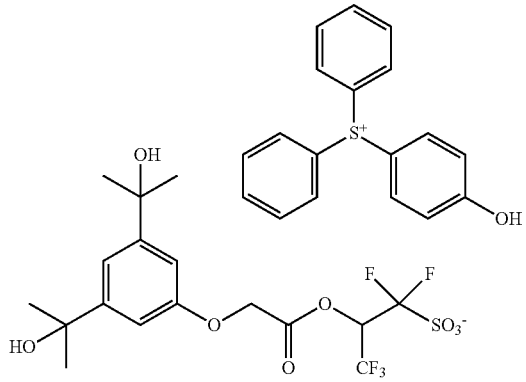

PAG-2

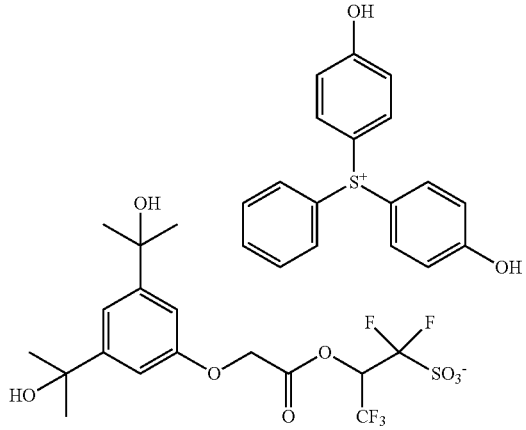

PAG-3

PAG-4
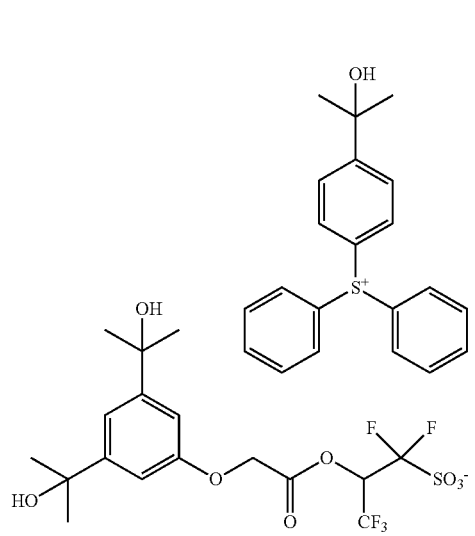
PAG-5
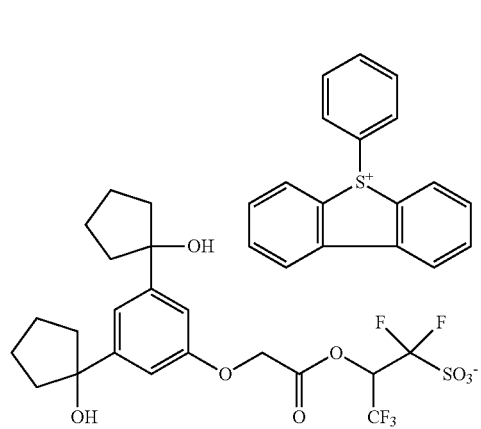
PAG-6
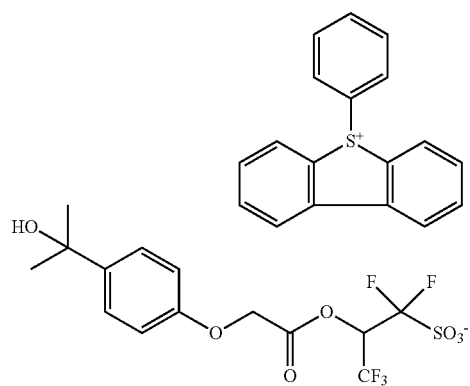
PAG-7
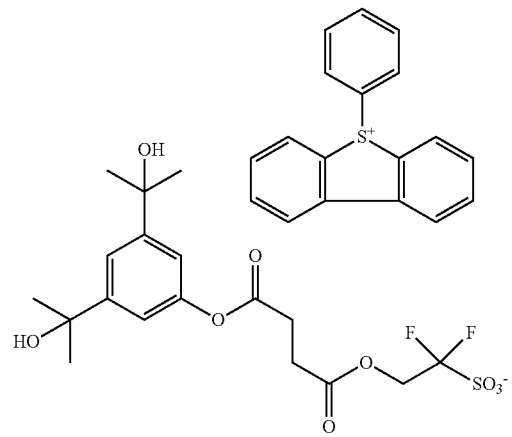
PAG-8
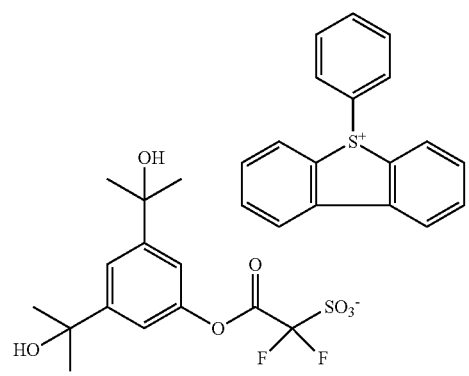
PAG-9
PAG-10
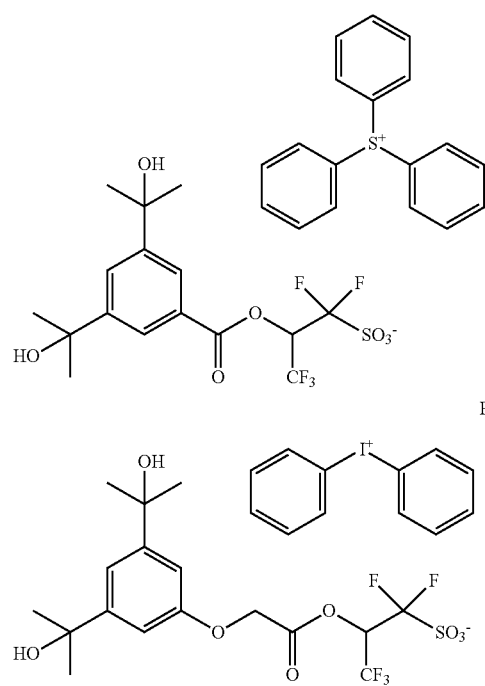

-continued
PAG-11
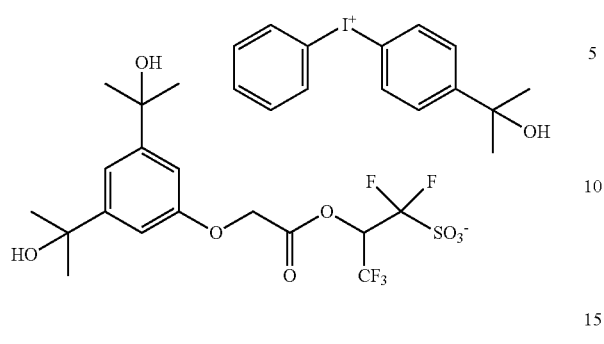
PAG-12
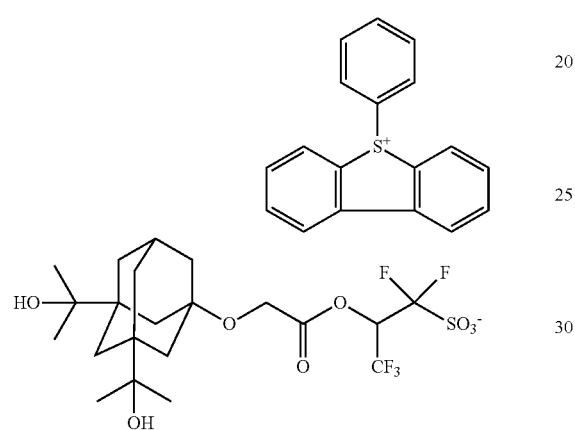
PAG-13
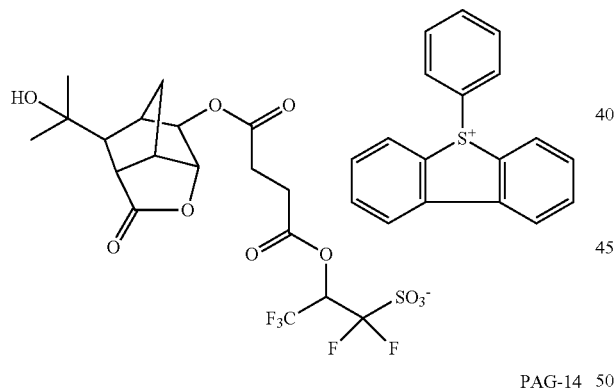
PAG-14
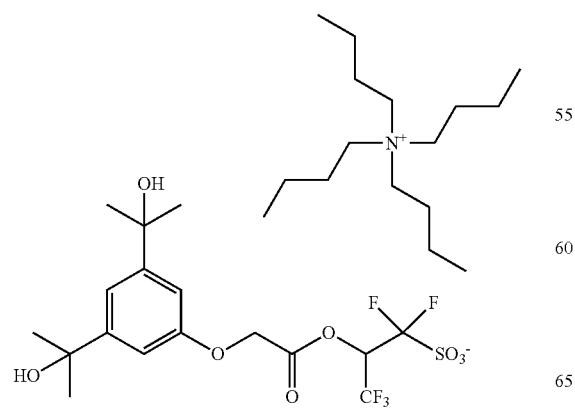
-continued
cPAG-1
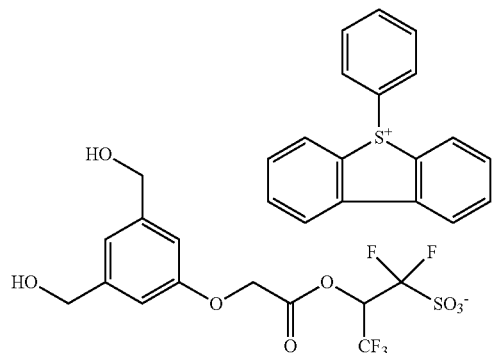
cPAG-2
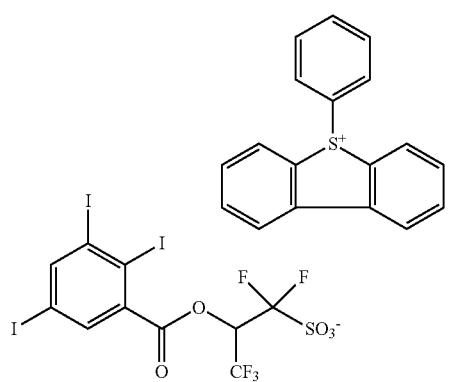
cPAG-3
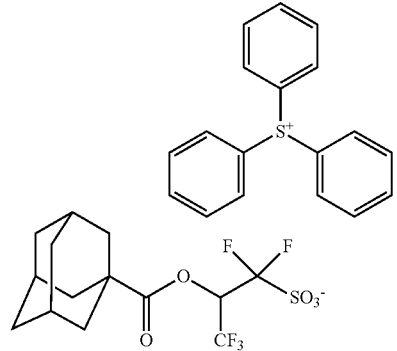
cPAG-4
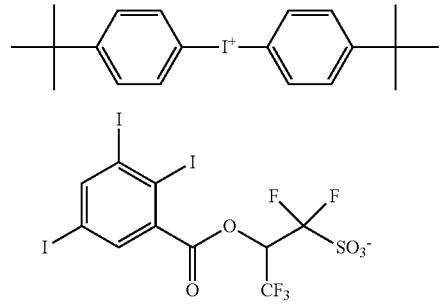

[2] Synthesis of Base Polymers

Synthesis Examples 1 to 24

Synthesis of Polymers P-1 to P-24

In nitrogen atmosphere, suitable monomers were combined, and copolymerization reaction was carried out in a solvent mixture of PGMEA and γ-butyrolactone. The polymerization solution was added dropwise to diisopropyl ether, whereupon the polymer precipitated out. After the solvent was decanted off the polymer was dissolved in acetone. The acetone solution was added dropwise to diisopropyl ether, after which the precipitated to polymer was filtered. The polymer was dissolved in acetone again. The acetone solution was added dropwise to water. The precipitate was collected by filtration and dried at 40° C. for 40 hours, obtaining the polymer as white solid. The polymer was analyzed for composition by $^1$H- and $^{13}$C-NMR and for Mw and Mw/Mn by GPC (polystyrene standards, THF solvent).

For Polymers P-1 to P-24, Table 1 tabulates the recurring units and proportions (mol %) thereof.

TABLE 1

| Polymer | Unit 1 | Proportion (mol %) | Unit 2 | Proportion (mol %) | Unit 3 | Proportion (mol %) | Unit 4 | Proportion (mol %) | Mw | Mw/Mn |
|---|---|---|---|---|---|---|---|---|---|---|
| P-1 | B1-1 | 60 | B2-1 | 40 | — | — | — | — | 4,200 | 1.62 |
| P-2 | B1-1 | 50 | B2-1 | 50 | — | — | — | — | 3,900 | 1.65 |
| P-3 | B1-1 | 65 | B2-2 | 35 | — | — | — | — | 4,100 | 1.66 |
| P-4 | B1-1 | 50 | B2-3 | 50 | — | — | — | — | 5,500 | 1.60 |
| P-5 | B1-1 | 40 | B2-4 | 50 | B3-1 | 10 | — | — | 4,300 | 1.59 |
| P-6 | B1-1 | 40 | B2-5 | 50 | B3-1 | 10 | — | — | 4,400 | 1.65 |
| P-7 | B1-2 | 75 | B2-1 | 25 | — | — | — | — | 4,000 | 1.68 |
| P-8 | B1-2 | 50 | B2-1 | 50 | — | — | — | — | 4,700 | 1.67 |
| P-9 | B1-2 | 55 | B2-2 | 45 | — | — | — | — | 4,400 | 1.67 |
| P-10 | B1-3 | 65 | B2-1 | 35 | — | — | — | — | 4,300 | 1.59 |
| P-11 | B1-3 | 75 | B2-1 | 25 | — | — | — | — | 5,000 | 1.61 |
| P-12 | B1-3 | 75 | B2-3 | 25 | — | — | — | — | 4,200 | 1.66 |
| P-13 | B1-3 | 60 | B2-4 | 35 | B3-1 | 5 | — | — | 5,200 | 1.70 |
| P-14 | B1-3 | 60 | B2-1 | 35 | B3-1 | 5 | — | — | 5,500 | 1.56 |
| P-15 | B1-3 | 60 | B2-1 | 35 | B4-1 | 5 | — | — | 4,300 | 1.55 |
| P-16 | B1-1 | 35 | B1-3 | 35 | B2-1 | 30 | — | — | 3,900 | 1.61 |
| P-17 | B1-1 | 30 | B1-3 | 40 | B2-1 | 25 | B3-1 | 5 | 4,600 | 1.58 |
| P-18 | B1-4 | 70 | B2-1 | 30 | — | — | — | — | 4,900 | 1.68 |
| P-19 | B1-1 | 50 | B1-4 | 20 | B2-1 | 30 | — | — | 5,000 | 1.64 |
| P-20 | B1-1 | 40 | B1-4 | 20 | B2-1 | 30 | B4-1 | 10 | 4,500 | 1.63 |
| P-21 | B1-5 | 60 | B2-1 | 40 | — | — | — | — | 4,300 | 1.67 |
| P-22 | B1-3 | 60 | B2-6 | 40 | — | — | — | — | 4,600 | 1.71 |
| P-23 | B1-5 | 60 | B2-6 | 40 | — | — | — | — | 5,100 | 1.70 |
| P-24 | B1-5 | 55 | B2-6 | 30 | B2-7 | 15 | — | — | 4,800 | 1.66 |

The structure of each recurring unit is shown below.

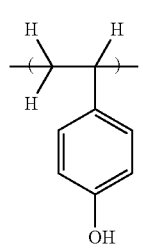

B1-1

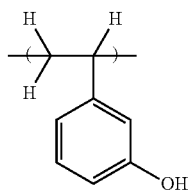

B1-2

-continued

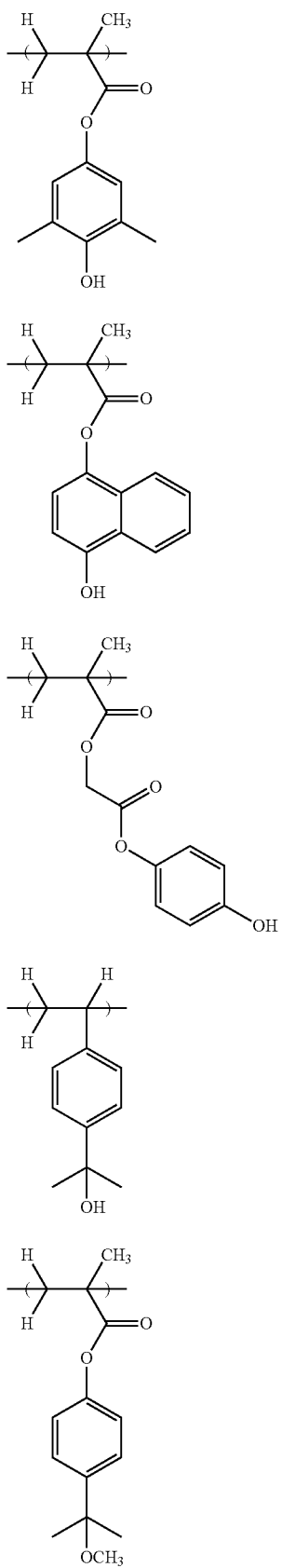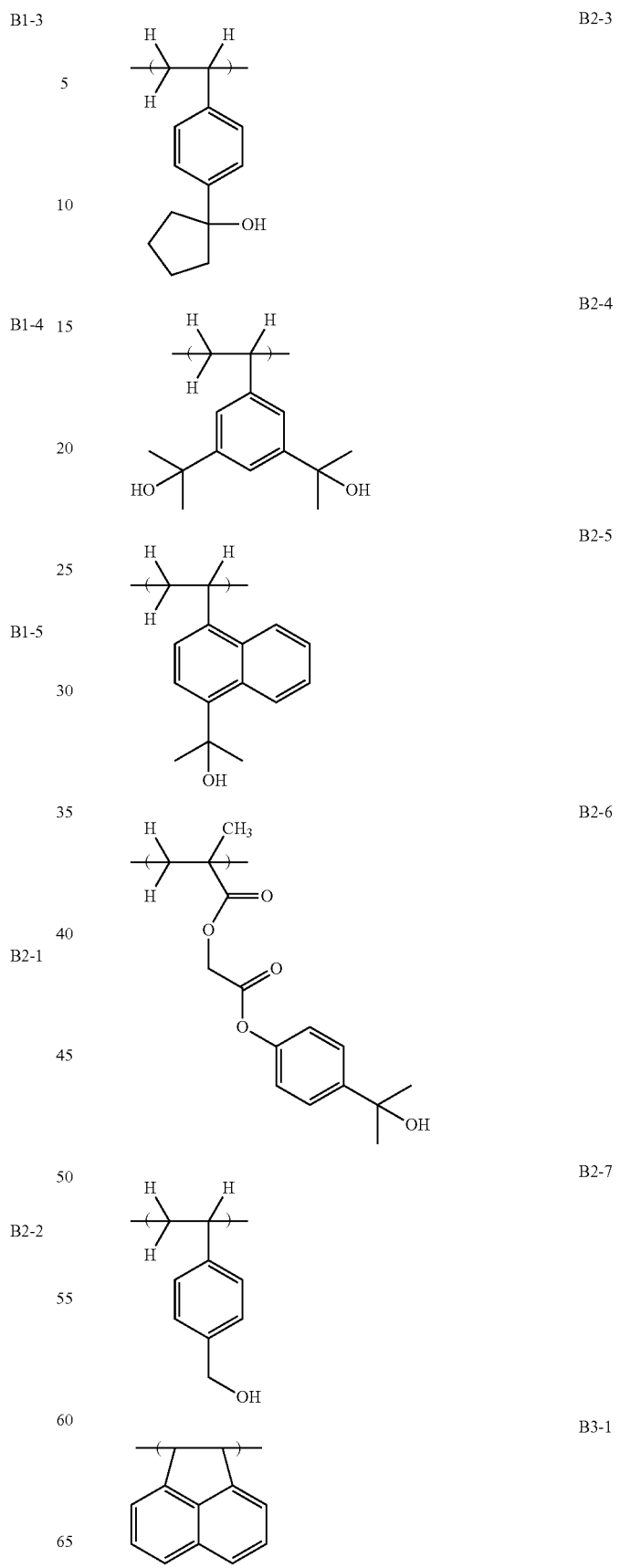

-continued

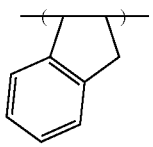

B4-1

[3] Preparation of Negative Resist Composition

Examples 2-1 to 2-36 and Comparative Examples 2-1 to 2-7

A negative resist composition was prepared by dissolving selected components in an organic solvent in accordance with the formulation shown in Tables 2 to 5, and filtering the solution through a UPE filter and/or nylon filter with a pore size of 0.02 μm.

TABLE 2

| | Resist Composition | Base polymer (pbw) | Acid generator (pbw) | Quencher (pbw) | Crosslinker (pbw) | Surfactant (pbw) | Organic Solvent (pbw) | |
|---|---|---|---|---|---|---|---|---|
| Example 2-1 | R-1 | P-1 (100) | PAG-1 (30) | Q-1 (5) | — | PF-636 (0.08) | PGMEA (4,400) | GBL (1,100) |
| 2-2 | R-2 | P-1 (100) | PAG-2 (30) | Q-1 (5) | — | PF-636 (0.08) | PGMEA (4,400) | GBL (1,100) |
| 2-3 | R-3 | P-2 (100) | PAG-3 (30) | Q-1 (5) | — | PF-636 (0.08) | PGMEA (4,400) | GBL (1,100) |
| 2-4 | R-4 | P-3 (100) | PAG-4 (30) | Q-1 (5) | — | PF-636 (0.08) | PGMEA (4,400) | GBL (1,100) |
| 2-5 | R-5 | P-4 (100) | PAG-5 (30) | Q-1 (5) | — | PF-636 (0.08) | PGMEA (4,400) | GBL (1,100) |
| 2-6 | R-6 | P-5 (100) | PAG-6 (30) | Q-1 (5) | — | PF-636 (0.08) | PGMEA (4,400) | GBL (1,100) |
| 2-7 | R-7 | P-6 (100) | PAG-6 (30) | Q-1 (5) | — | PF-636 (0.08) | PGMEA (4,400) | GBL (1,100) |
| 2-8 | R-8 | P-7 (100) | PAG-7 (30) | Q-2 (5) | — | PF-636 (0.08) | PGMEA (4,400) | GBL (1,100) |
| 2-9 | R-9 | P-21 (100) | PAG-7 (30) | Q-2 (5) | — | PF-636 (0.08) | PGMEA (4,400) | GBL (1,100) |
| 2-10 | R-10 | P-22 (100) | PAG-7 (30) | Q-2 (5) | — | PF-636 (0.08) | PGMEA (4,400) | GBL (1,100) |

TABLE 3

| | Resist composition | Base polymer (pbw) | Acid generator (pbw) | Quencher (pbw) | Crosslinker (pbw) | Surfactant (pbw) | Organic solvent (pbw) | |
|---|---|---|---|---|---|---|---|---|
| Example 2-11 | R-11 | P-7 (100) | PAG-1 (30) | Q-1 (6) | — | PF-636 (0.08) | PGMEA (4,400) | DAA (1,100) |
| 2-12 | R-12 | P-7 (100) | PAG-2 (30) | Q-1 (6) | — | PF-636 (0.08) | PGMEA (4,400) | DAA (1,100) |
| 2-13 | R-13 | P-8 (100) | PAG-3 (30) | Q-1 (6) | — | PF-636 (0.08) | PGMEA (4,400) | DAA (1,100) |
| 2-14 | R-14 | P-9 (100) | PAG-8 (30) | Q-1 (6) | — | PF-636 (0.08) | PGMEA (4,400) | DAA (1,100) |
| 2-15 | R-15 | P-9 (100) | PAG-8 (30) | Q-1 (6) | TMGU (4) | PF-636 (0.08) | PGMEA (4,400) | DAA (1,100) |
| 2-16 | R-16 | P-10 (100) | PAG-9 (30) | Q-1 (6) | — | PF-636 (0.08) | PGMEA (4,400) | DAA (1,100) |
| 2-17 | R-17 | P-11 (100) | PAG-10 (30) | Q-1 (6) | — | PF-636 (0.08) | PGMEA (4,400) | DAA (1,100) |
| 2-18 | R-18 | P-12 (100) | PAG-10 (30) | Q-1 (6) | — | PF-636 (0.08) | PGMEA (4,400) | DAA (1,100) |
| 2-19 | R-19 | P-13 (100) | PAG-11 (30) | Q-1 (6) | — | PF-636 (0.08) | PGMEA (4,400) | DAA (1,100) |
| 2-20 | R-20 | P-14 (100) | PAG-12 (30) | Q-2 (6) | — | PF-636 (0.08) | PGMEA (4,400) | DAA (1,100) |
| 2-21 | R-21 | P-14 (100) | PAG-12 (30) | Q-2 (6) | TMGU (4) | PF-636 (0.08) | PGMEA (4,400) | DAA (1,100) |
| 2-22 | R-22 | P-15 (100) | PAG-13 (30) | Q-2 (6) | — | PF-636 (0.08) | PGMEA (4,400) | DAA (1,100) |
| 2-23 | R-23 | P-16 (100) | PAG-13 (30) | Q-2 (6) | — | PF-636 (0.08) | PGMEA (4,400) | DAA (1,100) |
| 2-24 | R-24 | P-17 (100) | PAG-13 (30) | Q-2 (6) | — | PF-636 (0.08) | PGMEA (4,400) | DAA (1,100) |
| 2-25 | R-25 | P-18 (100) | PAG-1 (15) PAG-14 (15) | Q-2 (6) | — | PF-636 (0.08) | PGMEA (4,400) | DAA (1,100) |
| 2-26 | R-26 | P-18 (100) | PAG-2 (15) PAG-14 (15) | Q-2 (6) | — | PF-636 (0.08) | PGMEA (4,400) | DAA (1,100) |
| 2-27 | R-27 | P-19 (100) | PAG-3 (15) PAG-14 (15) | Q-2 (6) | — | PF-636 (0.08) | PGMEA (4,400) | DAA (1,100) |
| 2-28 | R-28 | P-20 (100) | PAG-4 (15) PAG-14 (15) | Q-1 (6) | — | PF-636 (0.08) | PGMEA (4,400) | DAA (1,100) |

TABLE 3-continued

|  | Resist composition | Base polymer (pbw) | Acid generator (pbw) | Quencher (pbw) | Crosslinker (pbw) | Surfactant (pbw) | Organic solvent (pbw) | |
|---|---|---|---|---|---|---|---|---|
| 2-29 | R-29 | P-23 (100) | PAG-4 (15) PAG-14 (15) | Q-1 (6) | — | PF-636 (0.08) | PGMEA (4,400) | DAA (1,100) |
| 2-30 | R-30 | P-24 (100) | PAG-4 (15) PAG-14 (15) | Q-1 (6) | — | PF-636 (0.08) | PGMEA (4,400) | DAA (1,100) |

TABLE 4

|  |  | Resist composition | Base polymer (pbw) | Acid generator (pbw) | Quencher (pbw) | Crosslinker (pbw) | Surfactant (pbw) | Organic solvent (pbw) | |
|---|---|---|---|---|---|---|---|---|---|
| Example | 2-31 | R-31 | P-2 (100) | PAG-1 (30) | Q-1 (6) | — | PF-636 (0.08) | PGMEA (4,400) | DAA (1,100) |
|  | 2-32 | R-32 | P-2 (100) | PAG-2 (30) | Q-1 (6) | — | PP-636 (0.08) | PGMEA (4,400) | DAA (1,100) |
|  | 2-33 | R-33 | P-2 (100) | PAG-4 (30) | Q-1 (6) | — | PF-636 (0.08) | PGMEA (4,400) | DAA (1,100) |
|  | 2-34 | R-34 | P-2 (100) | PAG-5 (30) | Q-1 (6) | — | PF-636 (0.08) | PGMEA (4,400) | DAA (1,100) |
|  | 2-35 | R-35 | P-2 (100) | PAG-10 (30) | Q-1 (6) | — | PF-636 (0.08) | PG-MEA (4,400) | DAA (1,100) |
|  | 2-36 | R-36 | P-2 (100) | PAG-12 (30) | Q-1 (6) | — | PF-636 (0.08) | PGMEA (4,400) | DAA (1,100) |

TABLE 5

|  |  | Resist composition | Base polymer (pbw) | Acid generator (pbw) | Quencher (pbw) | Crosslinker (pbw) | Surfactant (pbw) | Organic solvent (pbw) | |
|---|---|---|---|---|---|---|---|---|---|
| Comparative Example | 2-1 | cR-1 | P-1 (100) | cPAG-1 (30) | Q-1 (5) | — | PF-636 (0.08) | PGMEA (4,400) | GBL (1,100) |
|  | 2-2 | cR-2 | P-1 (100) | cPAG-2 (30) | Q-2 (5) | — | PF-636 (0.08) | PGMEA (4,400) | GBL (1,100) |
|  | 2-3 | cR-3 | P-7 (100) | cPAG-3 (30) | Q-1 (6) | — | PF-636 (0.08) | PGMEA (4,400) | DAA (1,100) |
|  | 2-4 | cR-4 | P-18 (100) | cPAG-4 (15) | Q-2 (6) | — | PF-636 (0.08) | PGMEA (4,400) | DAA (1,100) |
|  | 2-5 | cR-5 | P-2 (100) | cPAG-1 (30) | Q-1 (6) | — | PF-636 (0.08) | PGMEA (4,400) | DAA (1,100) |
|  | 2-6 | cR-6 | P-2 (100) | cPAG-2 (30) | Q-1 (6) | — | PF-636 (0.08) | PGMEA (4,400) | DAA (1,100) |
|  | 2-7 | cR-7 | P-2 (100) | cPAG-3 (30) | Q-1 (6) | — | PF-636 (0.08) | PGMEA (4,400) | DAA (1,100) |

The organic solvents, quenchers Q-1 and Q-2, crosslinker and surfactant in Tables 2 to 5 are identified below.

Solvents
propylene glycol monomethyl ether acetate (PGMEA)
γ-butyrolactone (GBL)
diacetone alcohol (DAA)

Quenchers Q-1 and Q-2

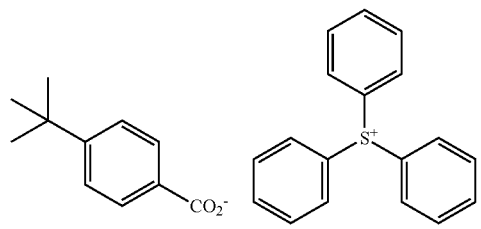

Q-1

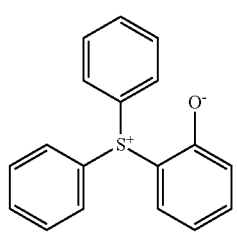

Q-2

Crosslinker: tetramethoxymethyl glycoluril (TMGU)
Surfactant: PolyFox PF-636 (Omnova Solutions, Inc.)

[4] EB Lithography Test

Examples 3-1 to 3-10 and Comparative Examples 3-1 to 3-2

An antireflective coating solution (DUV-42, Nissan Chemical Corp.) was coated on a silicon substrate and baked at 200° C. for 60 seconds to form an ARC of 61 nm thick. Each of the resist compositions (R-1 to R-10, cR-1, cR-2) was spin coated on the ARC and prebaked on a hotplate at 100° C. for 60 seconds to form a resist film of 45 nm thick. Using an EB lithography system ELS-F125 (Elionix Co., Ltd., accelerating voltage 125 kV), the resist film was exposed to a dot pattern of EB having a size of 26 in and a pitch of 52 nm (on-wafer) while changing the dose from 50 µC/cm² at a step of 1 µC/cm². The resist film was baked (PEB) at the temperature shown in Table 6 for 60 seconds and then puddle developed in a 2.38 wt % TMAH aqueous solution for 30 seconds. The resist film was rinsed with deionized water and spin dried, yielding a negative resist pattern or dot pattern. The dot pattern was observed under CD-SEM S9380 (Hitachi High Technologies Corp.) whereupon sensitivity, exposure latitude (EL), and CDU were evaluated by the following methods. The results are shown in Table 6.

Evaluation of Sensitivity

The optimum dose Eop (µC/cm²) which provided a dot pattern with a size of 26 nm and a pitch of 52 am was determined as an index of sensitivity. A smaller dose value indicates a higher sensitivity.

Evaluation of EL

The exposure dose which provided a dot pattern with a size of 26 mm±10% (i.e., 23 nm to 29 nm) was determined. EL (%) is calculated from the exposure doses according to the following equation:

$$EL\ (\%) = (|E1-E2|/Eop) \times 100$$

wherein E1 is an optimum exposure dose which provides a dot pattern with a size of 23 nm and a pitch of 52 nm, E2 is an optimum exposure dose which provides a dot pattern with a size of 29 nm and a pitch of 52 nm, and Eop is an optimum exposure dose which provides a dot pattern with a size of 26 nm and a pitch of 52 nm. A larger value indicates better EL.

Evaluation of CDU

For the dot pattern printed by exposure at the optimum dose Eop, the size was measured at 10 areas subject to an identical dose of shot (9 dots per area), from which a 3-old value (3σ) of standard deviation (σ) was determined and reported as CDU. A smaller value of 3σ indicates a dot pattern having improved CDU.

TABLE 6

|  |  | Resist composition | PEB temp. (° C.) | Sensitivity (µC/cm²) | EL (%) | CDU (nm) |
|---|---|---|---|---|---|---|
| Example | 3-1 | R-1 | 100 | 156 | 14.2 | 3.5 |
|  | 3-2 | R-2 | 100 | 145 | 15.5 | 3.7 |
|  | 3-3 | R-3 | 100 | 142 | 16 | 3.6 |
|  | 3-4 | R-4 | 100 | 137 | 15.7 | 3.9 |
|  | 3-5 | R-5 | 100 | 124 | 17.3 | 3.8 |
|  | 3-6 | R-6 | 100 | 146 | 12.8 | 3.8 |
|  | 3-7 | R-7 | 100 | 142 | 13 | 3.4 |
|  | 3-8 | R-8 | 100 | 136 | 14.9 | 3.4 |
|  | 3-9 | R-9 | 100 | 130 | 12.4 | 3.8 |
|  | 3-10 | R-10 | 100 | 125 | 11.9 | 3.9 |
| Comparative Example | 3-1 | cR-1 | 100 | 191 | 9.1 | 4.4 |
|  | 3-2 | cR-2 | 100 | 220 | 8.3 | 4.5 |

[5] EUV Lithography Test

Examples 4-1 to 4-20 and Comparative Examples 4-1 to 4-2

Each of the resist compositions (R-11 to R-30, cR-3, cR-4) was spin coated on a silicon substrate having a 20-nm coating of silicon-containing spin-on hard mask SHB-A940 (Shin-Etsu Chemical Co., Ltd., Si content 43 wt %) and prebaked on a hotplate at 105° C. for 60 seconds to form a resist film of 50 nm thick. Using an EUV scanner NXE3300 (ASML, NA 0.33, a 0.9/0.5, quadrupole illumination), the resist film was exposed to EUV. The resist film was baked (PEB) on a hotplate at the temperature shown in Table 7 for 60 seconds and developed in a 2.38 wt % TMAH aqueous solution for 30 seconds. The unexposed region was dissolved in the developer, yielding a negative resist pattern in the form of a LS pattern having a space width of 23 nm and a pitch of 46 m. The LS pattern was observed under CD-SEM (CG-5000 by Hitachi High Technologies Corp.). The resist pattern was evaluated as follows, with the results shown in Table 7.

Evaluation of Sensitivity

The optimum dose Eop (mJ/cm²) which provided a LS pattern with a space width of 23 nm and a pitch of 46 nm was determined as an index of sensitivity.

Evaluation of LWR

A LS pattern was formed by exposure in the optimum dose Eop. The space width was measured at longitudinally spaced apart 10 points, from which a 3-old value (3c) of standard deviation (a) was determined and reported as LWR. A smaller value of 3a indicates a pattern having a lower roughness and more uniform space width.

Evaluation of Profile

The profile of patterns printed at the optimum dose Eop was compared. A resist film providing a pattern of rectangular profile and perpendicular sidewall is evaluated good. A resist film providing a pattern of tapered profile with remarkably inclined sidewall or top-rounded profile due to top loss is evaluated NG.

TABLE 7

|  |  | Resist composition | PEB temp. (° C.) | Sensitivity (mJ/cm²) | LWR (nm) | Pattern profile |
|---|---|---|---|---|---|---|
| Example | 4-1 | R-11 | 100 | 24 | 4.4 | good |
|  | 4-2 | R-12 | 100 | 22 | 4.1 | good |
|  | 4-3 | R-13 | 100 | 21 | 3.7 | good |
|  | 4-4 | R-14 | 100 | 26 | 4.2 | good |
|  | 4-5 | R-15 | 100 | 26 | 4.0 | good |
|  | 4-6 | R-16 | 100 | 24 | 4.1 | good |
|  | 4-7 | R-17 | 100 | 10 | 3.7 | good |
|  | 4-8 | R-18 | 100 | 19 | 3.5 | good |
|  | 4-9 | R-19 | 100 | 18 | 3.4 | good |
|  | 4-10 | R-20 | 100 | 25 | 4.5 | good |
|  | 4-11 | R-21 | 100 | 24 | 4.0 | good |
|  | 4-12 | R-22 | 100 | 26 | 4.3 | good |
|  | 4-13 | R-23 | 100 | 25 | 4.2 | good |
|  | 4-14 | R-24 | 100 | 28 | 4.1 | good |
|  | 4-15 | R-25 | 100 | 25 | 3.9 | good |
|  | 4-16 | R-26 | 100 | 23 | 3.8 | good |
|  | 4-17 | R-27 | 100 | 24 | 3.9 | good |
|  | 4-18 | R-28 | 100 | 23 | 3.6 | good |
|  | 4-19 | R-29 | 100 | 21 | 4.3 | good |
|  | 4-20 | R-30 | 100 | 21 | 4.4 | good |
| Comparative Example | 4-1 | cR-3 | 100 | 30 | 5.1 | NG |
|  | 4-2 | cR-4 | 110 | 32 | 5.2 | NG |

[6] Evaluation of Remaining Film in Exposed Region

Examples 5-1 to 5-6 and Comparative Examples 5-1 to 5-3

Each of the resist compositions (R-31 to R-36, cR-5 to cR-7) was spin coated on a silicon substrate having a 20-nm coating of silicon-containing spin-on hard mask SHB-A940 (Shin-Etsu Chemical Co., Ltd., Si content 43 wt %) and prebaked on a hotplate at 105° C. for 60 seconds to form a resist film of 50 nm thick. By means of KrF excimer laser scanner S206D (Nikon Corp., NA=0.82, conventional illumination), the resist film was exposed in a varying dose. The resist film was baked (PEB) on a hotplate at the temperature shown in Table 8 for 60 seconds and developed in a 2.38 wt % TMAH aqueous solution for 30 seconds.

Figure 2:
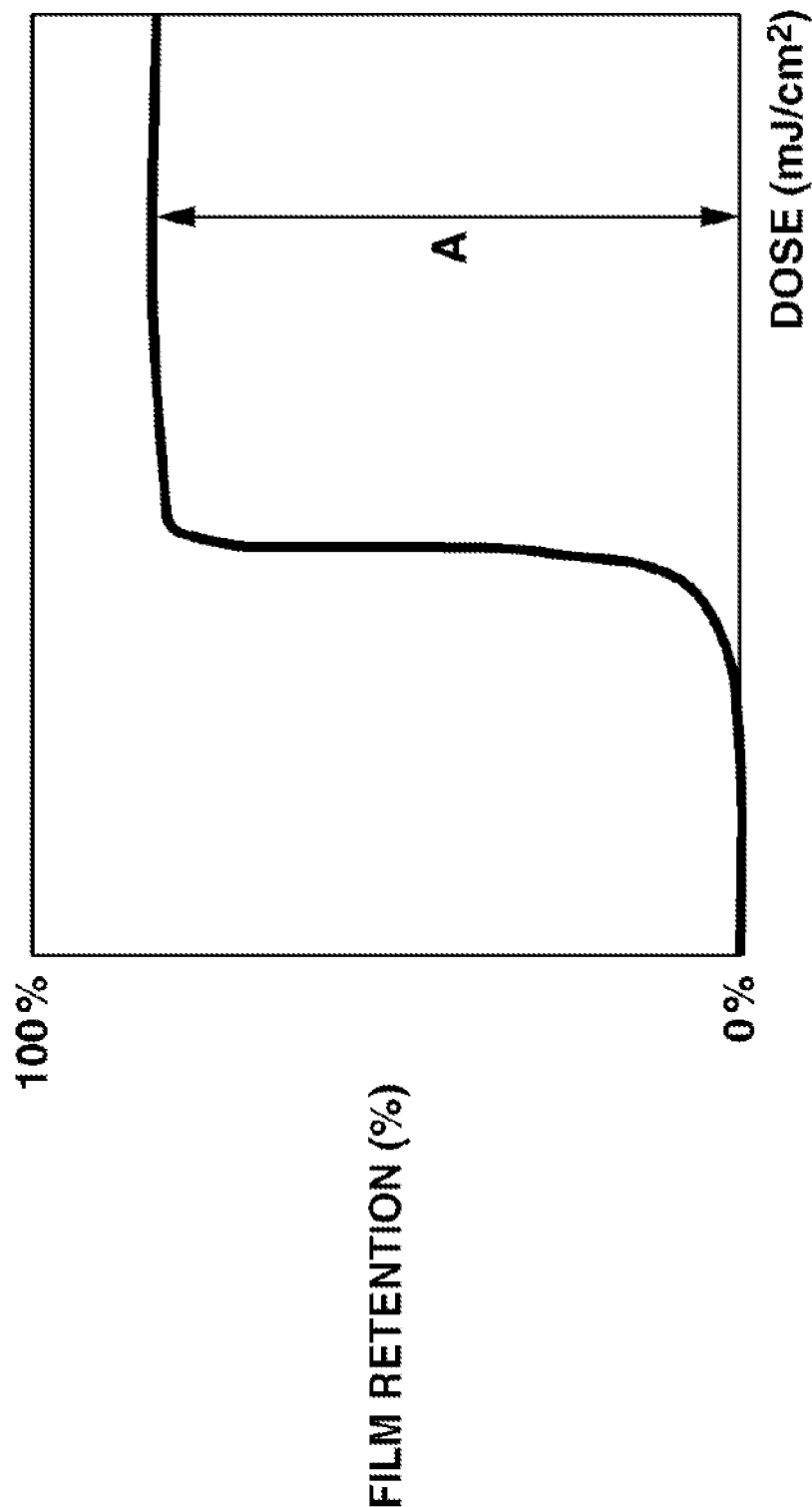
FIG. 2 is a graph showing a percent film retention as a function of exposure dose.

The thickness of the resist film in areas of different doses was measured by an ellipsometric film thickness measurement system RE-3100 (Screen Semiconductor Solutions Co., Ltd.). The thickness of film in each dose area divided by the thickness of film as coated is computed and reported as a film retention (%). FIG. 2 is a graph which is drawn by plotting the dose on the abscissa and the film retention on the ordinate. As is evident from FIG. 2, the chemically amplified negative resist composition to be developed in an alkaline developer shows the tendency that the resist film retention ramps with an increasing dose. The film retention is eventually saturated. The film retention as saturated (the value of arrow A in FIG. 2) is shown as "saturation film retention" in Table 8. A large value of saturation film retention indicates that the dissolution of exposed region in alkaline developer is suppressed.

Film retention (%)=[thickness (nm) of film in each dose area]/[thickness (=50 nm) of film as coated]×100

TABLE 8

| | Resist composition | PEB temperature (° C.) | Saturation film retention (%) |
|---|---|---|---|
| Example 5-1 | R-31 | 100 | 91 |
| 5-2 | R-32 | 100 | 92 |
| 5-3 | R-33 | 100 | 94 |
| 5-4 | R-34 | 100 | 95 |
| 5-5 | R-35 | 100 | 93 |
| 5-6 | R-36 | 100 | 95 |
| Comparative 5-1 | cR-5 | 100 | 78 |
| Example 5-2 | cR-6 | 100 | 84 |
| 5-3 | cR-7 | 100 | 73 |

As is evident from Tables 6 and 7, the chemically amplified negative resist composition is excellent in sensitivity, LWR, CDU and pattern profile when processed by the EB lithography and EUV lithography. As is evident from Table 8, the chemically amplified negative resist composition shows improved saturation film retention, i.e., controlled dissolution of exposed region in alkaline developer, when processed by the KrF lithography.

Japanese Patent Application No. 2020-097345 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An onium salt containing an anion having the formula (A1) and a cation selected from the formulae (A1-A) to (A1-c):

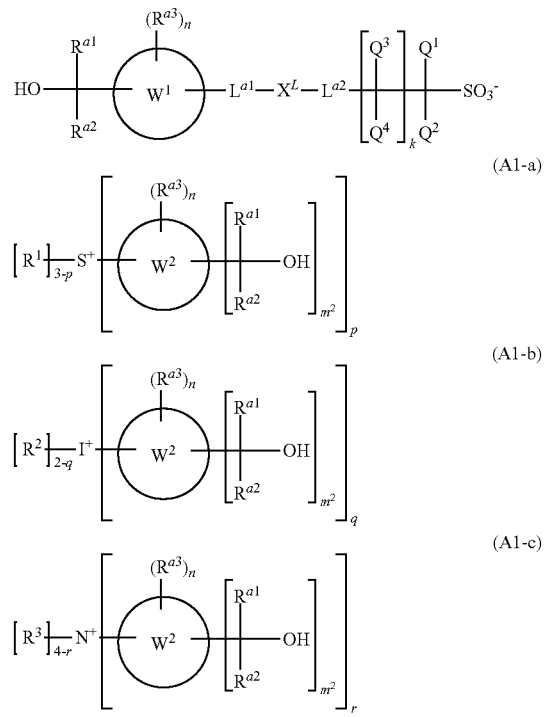

wherein $R^{a1}$ and $R^{a2}$ are each independently hydrogen or a $C_1$-$C_{10}$ hydrocarbyl group in which some or all hydrogen atoms may be substituted by halogen and a constituent —$CH_2$— may be replaced by —O— or —C(=O)—, both $R^{a1}$ and $R^{a2}$ are not hydrogen at the same time, $R^{a1}$ and $R^{a2}$ may bond together to form an aliphatic ring with the carbon atom to which they are attached, the broken line designates a valence bond, k is an integer of 0 to 4, $m^1$ is an integer of 1 to 4, $m^2$ is each independently an integer of 0 to 4, n is each independently an integer of 0 to 10, p is an integer of 0 to 3, q is an integer of 0 to 2, r is an integer of 0 to 4, $R^{a3}$ is each independently a $C_1$-$C_{20}$ hydrocarbyl group which may contain a heteroatom, when n is 2 or more, $R^{a3}$ may be the same or different and two or more $R^{a3}$ may bond together to form a ring with the atom on $W^2$ to which they are attached, $W^1$ is a $C_3$-$C_{20}$ (n+2)-valent group having a mono- or polycyclic structure, $W^2$ is each independently a $C_3$-$C_{20}$ ($m^2$+n+1)-valent group having a mono- or polycyclic structure, in which a constituent —$CH_2$— may be replaced by —O—, —S— or —C(=O)—, $Q^1$ and $Q^2$ are each independently fluorine or a $C_1$-$C_6$ fluorinated saturated hydrocarbyl group, $Q^3$ and $Q^4$ are each independently hydrogen, fluorine or a $C_1$-$C_6$ fluorinated saturated hydrocarbyl group, $L^{a1}$ and $L^{a2}$ are each independently a single bond, ether bond, ester bond, sulfonate bond, carbonate bond or carbamate bond, $X^L$ is a single bond or a $C_1$-$C_{40}$ hydrocarbylene group which may contain a heteroatom, $R^1$, $R^2$ and $R^3$ are each independently a $C_1$-$C_{20}$ hydrocarbyl group which may contain a heteroatom, any two of two $R^1$ and $W^2$ may bond together to form a ring with the sulfur atom in the formula, any two of three $R^3$ and $W^2$ may bond together to form a ring with the nitrogen atom in the formula.

2. The onium salt of claim 1 wherein the anion having formula (A1) has the formula (A2):

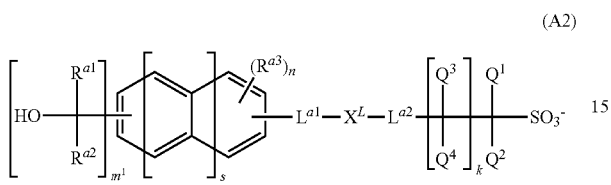

(A2)

wherein $Q^1$ to $Q^4$, $L^{a1}$, $L^{a2}$, $X^L$, $R^{a1}$ to $R^{a3}$, k, $m^1$ and n are as defined above, s is an integer of 0 to 2.

3. The onium salt of claim 2 wherein the anion having formula (A2) is represented by the formula (A3):

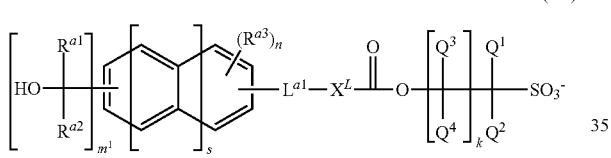

(A3)

wherein $Q^1$ to $Q^4$, $L^{a1}$, $X^L$, $R^{a1}$ to $R^{a3}$, k, $m^1$, n and s are as defined above.

4. The onium salt of claim 3 wherein the anion having formula (A3) is represented by the formula (A4):

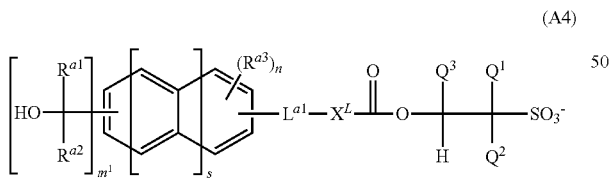

(A4)

wherein $Q^1$ to $Q^3$, $L^{a1}$, $X^L$, $R^{a1}$ to $R^{a3}$, $m^1$, n and s are as defined above.

5. A photoacid generator comprising the onium salt of claim 1.

6. A chemically amplified negative resist composition, comprising:
the photoacid generator of claim 5; and
a base polymer comprising recurring units having the formula (B1) and recurring units having the formula (B2):

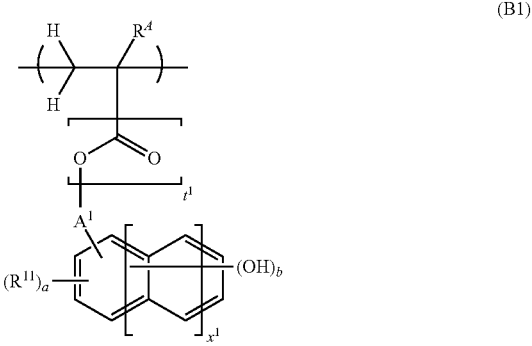

(B1)

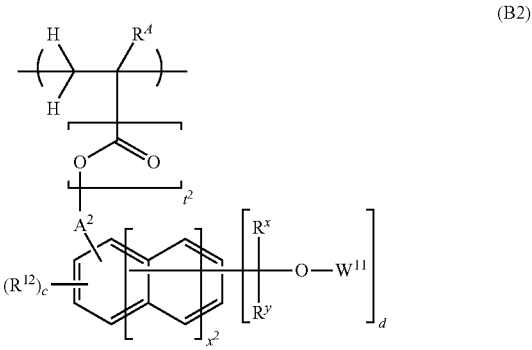

(B2)

wherein $R^A$ is hydrogen, fluorine, methyl or trifluoromethyl, $R^{11}$ and $R^{12}$ are each independently halogen, an optionally halogenated $C_1$-$C_6$ saturated hydrocarbyl group, optionally halogenated $C_2$-$C_8$ saturated hydrocarbyl-carbonyloxy group, or optionally halogenated $C_1$-$C_6$ saturated hydrocarbyloxy group, $A^1$ and $A^2$ are each independently a single bond or a $C_1$-$C_{10}$ saturated hydrocarbylene group in which a constituent —$CH_2$— may be replaced by —O—, $W^{11}$ is hydrogen, a $C_1$-$C_{10}$ aliphatic hydrocarbyl group, or an optionally substituted aryl group, a constituent —$CH_2$— in the aliphatic hydrocarbyl group may be replaced by —O—, —C(=O)—, —O—C(=O)— or —C(=O)—O—, $R^x$ and $R^y$ are each independently hydrogen, or a $C_1$-$C_{15}$ saturated hydrocarbyl group which may be substituted with a hydroxyl or saturated hydrocarbyloxy moiety, or an optionally substituted aryl group, both $R^x$ and $R^y$ are not hydrogen at the same time, $R^x$ and $R^y$ may bond together to form a ring with the carbon atom to which they are attached, $t^1$ and $t^2$ are each independently 0 or 1, $x^1$ and $x^2$ are each independently an integer of 0 to 2, a is an integer meeting $0 \le a \le 5+2x^1-b$, c is an integer meeting $0 \le c \le 5+2x^2-d$, b and d are each independently an integer of 1 to 3.

7. The chemically amplified negative resist composition of claim 6, wherein the recurring units of formula (B1) have the formula (B1-1) and the recurring units of formula (B2) have the formula (B2-1):

(B1-1)

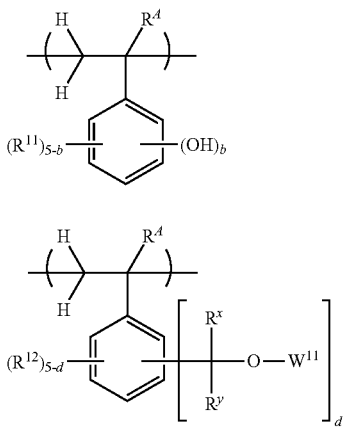

(B2-1)

wherein $R^A$, $R^{11}$, $R^{12}$, $R^x$, $R^y$, $W^{11}$, b and d are as defined above.

8. The chemically amplified negative resist composition of claim 6, wherein the base polymer further comprises recurring units of at least one type selected from recurring units having the formula (B3), recurring units having the formula (B4), and recurring units having the formula (B5):

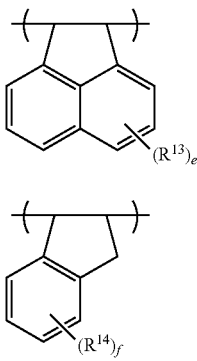

(B3)

(B4)

(B5)

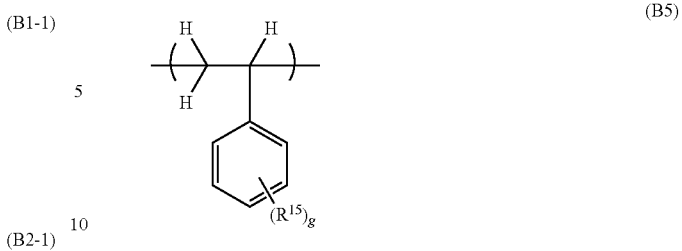

wherein $R^{13}$ and $R^{14}$ are each independently hydroxyl, halogen, acetoxy, an optionally halogenated $C_1$-$C_8$ alkyl group, optionally halogenated $C_1$-$C_8$ saturated hydrocarbyloxy group, optionally halogenated $C_2$-$C_8$ saturated hydrocarbylcarbonyl group, or optionally halogenated $C_2$-$C_8$ saturated hydrocarbylcarbonyloxy group, with the proviso that $R^{13}$ and $R^{14}$ are not acid labile groups, $R^{15}$ is halogen, acetoxy, an optionally halogenated $C_1$-$C_8$ alkyl group, optionally halogenated $C_1$-$C_8$ saturated hydrocarbyloxy group, optionally halogenated $C_2$-$C_8$ saturated hydrocarbylcarbonyl group, or optionally halogenated $C_2$-$C_8$ saturated hydrocarbylcarbonyloxy group, with the proviso that $R^{15}$ is not an acid labile group, e, f and g are each independently an integer of 0 to 4.

9. The chemically amplified negative resist composition of claim 6, further comprising an organic solvent.

10. The chemically amplified negative resist composition of claim 6, further comprising a quencher.

11. The chemically amplified negative resist composition of claim 6, further comprising a crosslinker.

12. A process for forming a resist pattern comprising the steps of applying the chemically amplified negative resist composition of claim 6 onto a substrate to form a resist film thereon, exposing patternwise the resist film to high-energy radiation, and developing the exposed resist film in an alkaline developer.

13. The process of claim 12 wherein the high-energy radiation is EB or EUV of wavelength 3 to 15 nm.

14. The onium salt of claim 1 wherein $L^{a1}$ and $L^{a2}$ are each independently an ether bond, ester bond, sulfonate bond, or carbamate bond, and $X^L$ is a $C_1$-$C_{40}$ hydrocarbylene group which may contain a heteroatom.

15. The onium salt of claim 1 wherein $L^{a1}$ and $X^L$ is a single bond, and $L^{a2}$ is an ether bond or ester bond.

* * * * *